(12) United States Patent
Mohsen et al.

(10) Patent No.: US 11,813,258 B2
(45) Date of Patent: Nov. 14, 2023

(54) THERAPY FOR MITOCHONDRIAL FATTY ACID BETA-OXIDATION AND TRANSPORT DISORDERS

(71) Applicant: University of Pittsburgh—Of the Commonwealth System of Higher Education, Pittsburgh, PA (US)

(72) Inventors: Al-Walid A. Mohsen, Gibsonia, PA (US); Gerard Vockley, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 43 days.

(21) Appl. No.: 17/344,084

(22) Filed: Jun. 10, 2021

(65) Prior Publication Data

US 2021/0308128 A1   Oct. 7, 2021

Related U.S. Application Data

(62) Division of application No. 16/345,757, filed as application No. PCT/US2017/061712 on Nov. 15, 2017, now Pat. No. 11,077,105.

(60) Provisional application No. 62/422,124, filed on Nov. 15, 2016.

(51) Int. Cl.
| | |
|---|---|
| *A61K 31/496* | (2006.01) |
| *A61P 3/08* | (2006.01) |
| *A61K 31/426* | (2006.01) |
| *A61K 45/06* | (2006.01) |
| *A61K 31/495* | (2006.01) |
| *A61K 38/45* | (2006.01) |

(52) U.S. Cl.
CPC .......... *A61K 31/496* (2013.01); *A61K 31/426* (2013.01); *A61K 31/495* (2013.01); *A61K 45/06* (2013.01); *A61P 3/08* (2018.01); *A61K 38/45* (2013.01)

(58) Field of Classification Search
CPC .. A61K 31/496; A61K 31/426; A61K 31/495; A61K 45/06; A61K 38/45; A61P 3/08
USPC .................................................... 514/254.01
See application file for complete search history.

(56) References Cited

U.S. PATENT DOCUMENTS

| | | |
|---|---|---|
| 5,283,246 A | 2/1994 | Regnier et al. |
| 9,416,364 B2 | 8/2016 | Gonzalez et al. |
| 10,035,819 B2 | 7/2018 | Evans et al. |
| 2012/0094293 A1 | 4/2012 | Spiegelman et al. |
| 2015/0216824 A1 | 8/2015 | Mohamed et al. |
| 2016/0023991 A1 | 1/2016 | Evans et al. |
| 2016/0354366 A1 | 12/2016 | Yu |
| 2017/0226154 A1 | 8/2017 | Evans et al. |
| 2017/0304255 A1 | 10/2017 | Baiga et al. |
| 2017/0305894 A1 | 10/2017 | Baiga et al. |

FOREIGN PATENT DOCUMENTS

| | | |
|---|---|---|
| WO | 0177336 A2 | 10/2001 |
| WO | 2012109176 A2 | 8/2012 |
| WO | 2016057322 A1 | 4/2016 |
| WO | 2016173486 A1 | 11/2016 |
| WO | 2017218963 A1 | 12/2017 |

OTHER PUBLICATIONS

Akers, "Parenteral Preparations", The Science and Practice of Pharmacy, 2006, pp. 802-836, 21st Edition, Lippincott Williams & Wilkins, Philadelphia.
Aliefendioğlu et al., "A newborn with VLCAD deficiency Clinical, biochemical, and histopathological findings", European Journal of Pediatrics, 2007, pp. 1077-1080, vol. 166.
Ancerewicz et al., "Structure-Property Relationships of Trimetazidine Derivatives and Model Compounds as Potential Antioxidants", Free Radical Biology & Medicine, 1998, pp. 113-120, vol. 25, No. 1.
Andresen et al., "Clear Correlation of Genotype with Disease Phenotype in Very-Long-Chain Acyl-CoA Dehydrogenase Deficiency", American Journal of Human Genetics, 1999, pp. 479-494, vol. 64.
Arnold et al., "A Delphi clinical practice protocol for the management of very long chain acyl-CoA dehydrogenase deficiency", Molecular Genetics and Metabolism, 2009, pp. 85-90, vol. 96.
Boneh et al., "VLCAD deficiency: Pitfalls in newborn screening and confirmation of diagnosis by mutation analysis", Molecular Genetics and Metabolism, 2006, pp. 166-170, vol. 88.
Crowley, "Solutions, Emulsions, Suspensions, and Extracts", The Science and Practice of Pharmacy, 2006, pp. 745-775, 21st Edition, Lippincott Williams & Wilkins, Philadelphia.
Goetzman et al., "Expression and characterization of mutations in human very long-chain acyl-CoA dehydrogenase using a prokaryotic system", Molecular Genetics and Metabolism, 2007, pp. 138-147, vol. 91.
Goetzman et al., "Long-chain Acyl-CoA Dehydrogenase Deficiency as a Cause of Pulmonary Surfactant Dysfunction", The Journal of Biological Chemistry, 2014, pp. 10668-10679, vol. 289, No. 15.
Gregersen et al., "Mitochondrial fatty acid oxidation defects—remaining challenges", Journal of Inherited Metabolism Disorders, 2008, pp. 643-657, vol. 31.

(Continued)

*Primary Examiner* — Kristin A Vajda
(74) *Attorney, Agent, or Firm* — The Webb Law Firm

(57) ABSTRACT

Methods of treating mitochondrial fatty acid β-oxidation and/or transport disorders arising from mutant proteins in the mitochondrial fatty acid β-oxidation and transport metabolic pathways in patients are provided. The methods modulate the mitochondrial fatty acid β-oxidation pathway at the last step so that the product of the mutant protein accumulates and stabilizes the mutant protein and/or the substrate(s)/product(s) of the down stream reactions accumulate and possibly bind to allosteric sites on the mutant protein to stabilize it. Trimetazidine pharmacodynamics function as such in the β-oxidation pathway. Further, a synergistic effect is observed where trimetazidine and PPARδ agonist combination enhanced enzyme activity and presence significantly more than either alone.

15 Claims, 19 Drawing Sheets

Specification includes a Sequence Listing.

(56) References Cited

OTHER PUBLICATIONS

Kálai et al., "Structure-activity studies on the protection of Trimetazidine derivatives modified with nitroxides and their precursors from myocardial ischemia-reperfusion injury", Bioorganic & Medicinal Chemistry, 2006, pp. 5510-5516, vol. 14.

Kamijo et al., "Mitochondrial Trifunctional Protein Deficiency—Catalytic Heterogeneity of the Mutant Enzyme in Two Patients", The Journal of Clinical Investigation, 1994, pp. 1740-1747, vol. 93.

Kantor et al., "The Antianginal Drug Trimetazidine Shifts Cardiac Energy Metabolism from Fatty Acid Oxidation to Glucose Oxidation by Inhibiting Mitochondrial Long-Chain 3-Ketoacyl Coenzyme A Thiolase", Circulation Research, 2000, pp. 580-588, vol. 86.

Kutala et al., "Attenuation of Myochardial Ischemia-Reperfusion Injury by Trimetazidine Derivatives Functionalized with Antioxidant Properties", The Journal of Pharmacology and Experimental Therapeutics, 2006, pp. 921-928, vol. 317, No. 3.

Laforêt et al., "Diagnostic assessment and long-term follow-up of 13 patients with Very Long-Chain Acyl-Coenzyme A dehydrogenase (VLCAD) deficiency", Neuromuscular Disorders, 2009, pp. 324-329, vol. 19.

Lehman et al., "An Acyl-Coenzyme A Dehydrogenase Assay Utilizing the Ferricenium Ion", Analytical Biochemistry, 1990, pp. 280-284, vol. 186.

Mathur et al., "Molecular Heterogeneity in Very-Long-Chain Acyl-CoA Dehydrogenase Deficiency Causing Pediatric Cardiomyopathy and Sudden Death", Circulation, 1999, pp. 1337-1343, vol. 99.

Nasser et al., "Thermal unfolding of medium-chain acyl-CoA dehydrogenase and iso(3)valeryl-CoA dehydrogenase: study of the effect of genetic defects on enzyme stability", Biochimica et Biophysica Acta, 2004, pp. 22-32, vol. 1690.

O'Connor et al., "Powders", The Science and Practice of Pharmacy, 2006, pp. 702-719, 21st Edition, Lippincott Williams & Wilkins, Philadelphia.

Pena et al., "Outcomes and genotype-phenotype correlations in 52 individuals with VLCAD deficiency diagnosed by NBS and enrolled in the IBEM-IS database", Molecular Genetics and Metabolism, 2016, pp. 272-281, vol. 118.

Pons et al., "Clinical and Molecular Heterogeneity in Very-Long-Chain Acyl-Coenzyme A Dehydrogenase Deficiency", Pediatric Neurology, 2000, pp. 98-105, vol. 22, No. 2.

Reilly et al., "PPAR delta as a therapeutic target in metabolic disease", FEBS Letters, 2008, pp. 26-31, vol. 582, No. 1.

Rudnic et al., "Oral Solid Dosage Forms", The Science and Practice of Pharmacy, 2006, pp. 889-928, 21st Edition, Lippincott Williams & Wilkins, Philadelphia.

Spiekerkoetter et al., "Molecular and Phenotypic Heterogeneity in Mitochondrial Trifunctional Protein Deficiency Due to β-Subunit Mutations", Human Mutation, 2003, pp. 598-607, vol. 21.

Spiekerkoetter et al., "The early-onset phenotype of mitochondrial trifunctional protein deficiency: A lethal disorder with multiple tissue involvement", Journal of Inherited Metabolic Disease, 2004, pp. 294-296, vol. 27.

Spiekerkoetter et al., "Management and outcome in 75 individuals with long-chain fatty acid oxidation defects: results from a workshop", Journal of Inherited Metabolic Disease, 2009, pp. 488-497, vol. 32.

Stanley et al., "Metabolic therapy in the treatment of ischaemic heart disease: the pharmacology of trimetazidine", Fundamental & Clinical Pharmacology, 2003, pp. 133-145, vol. 17.

Tang, "Metabolic Approach in Heart Failure: Rethinking How We Translate From Theory to Clinical Practice", Journal of the American College of Cardiology, 2006, pp. 999-1000, vol. 48, No. 5.

Turco, "Intravenous Admixtures", The Science and Practice of Pharmacy, 2006, pp. 837-849, 21st Edition, Lippincott Williams & Wilkins, Philadelphia.

Vockley et al., "Mammalian Branched-Chain Acyl-CoA Dehydrogenases: Molecular Cloning and Characterization of Recombinant Enzymes", Methods in Enzymology, 2000, pp. 241-258, vol. 324.

Watanabe et al., "Molecular Basis of Very Long Chain Acyl-CoA Dehydrogenase Deficiency in Three Israeli Patients: Identification of a Complex Mutant Allele With P65L and K247Q Mutations, the Former Being an Exonic Mutation Causing Exon 3 Skipping", Human Mutation, 2000, pp. 430-438, vol. 15.

Zhang et al., "Clinical features and mutations in seven Chinese patients with very long chain acyl-CoA dehydrogenase deficiency", World Journal of Pediatrics, 2014, pp. 119-125, vol. 10, No. 2.

Mohsen et al., "Ligand-Induced Conformational Changes of Thymidylate Synthase Detected by Limited Proteolysis", Biochemistry, 1995, pp. 1669-1677, vol. 34, No. 5.

VLCAD Protein (e.g., UniProtKB - P49748, SEQ ID NO: 1)

```
         10         20         30         40         50
MQAARMAASL GRQLLRLGGG SSRLTALLGQ PRPGPARRPY AGGAAQLALD
         60         70         80         90        100
KSDSHPSDAL TRKKPAKAES KSFAVGMFKG QLTTDQVFPY PSVLNEEQTQ
        110        120        130        140        150
FLKELVEPVS RFFEEVNDPA KNDALEMVEE TTWQGLKELG AFGLQVPSEL
        160        170        180        190        200
GGVGLCNTQY ARLVEIVGMH DLGVGITLGA HQSIGFKGIL LFGTKAQKEK
        210        220        230        240        250
YLPKLASGET VAAFCLTEPS SGSDAASIRT SAVPSPCGKY YTLNGSKLWI
        260        270        280        290        300
SNGGLADIFT VFAKTPVTDP ATGAVKEKIT AFVVERGFGG ITHGPPEKKM
        310        320        330        340        350
GIKASNTAEV FFDGVRVPSE NVLGEVGSGF KVAMHILNNG RFGMAAALAG
        360        370        380        390        400
TMRGIIAKAV DHATNRTQFG EKIHNFGLIQ EKLARMVMLQ YVTESMAYMV
        410        420        430        440        450
SANMDQGATD FQIEAAISKI FGSEAAWKVT DECIQIMGGM GFMKEPGVER
        460        470        480        490        500
VLRDLRIFRI FEGTNDILRL FVALQGCMDK GKELSGLGSA LKNPFGNAGL
        510        520        530        540        550
LLGEAGKQLR RRAGLGSGLS LSGLVHPELS RSGELAVRAL EQFATVVEAK
        560        570        580        590        600
LIKHKKGIVN EQFLLQRLAD GAIDLYAMVV VLSRASRSLS EGHPTAQHEK
        610        620        630        640        650
MLCDTWCIEA AARIREGMAA LQSDPWQQEL YRNFKSISKA LVERGGVVTS

NPLGF
```

*Fig. 2A*

LCAD (UniProtKB - P28330; SEQ ID NO: 2)

```
          10         20         30         40         50
   MAARLLRGSL RVLGGHRAPR QLPAARCSHS GGEERLETPS AKKLTDIGIR
          60         70         80         90        100
   RIFSPEHDIF RKSVRKFFQE EVIPHHSEWE KAGEVSREVW EKAGKQGLLG
         110        120        130        140        150
   VNIAEHLGGI GGDLYSAAIV WEEQAYSNCS GPGFSIHSGI VMSYITNHGS
         160        170        180        190        200
   EEQIKHFIPQ MTAGKCIGAI AMTEPGAGSD LQGIKTNAKK DGSDWILNGS
         210        220        230        240        250
   KVFISNGSLS DVVIVVAVTN HEAPSPAHGI SLFLVENGMK GFIKGRKLHK
         260        270        280        290        300
   MGLKAQDTAE LFFEDIRLPA SALLGEENKG FYYIMKELPQ ERLLIADVAI
         310        320        330        340        350
   SASEFMFEET RNYVKQRKAF GKTVAHLQTV QHKLAELKTH ICVTRAFVDN
         360        370        380        390        400
   CLQLHEAKRL DSATACMAKY WASELQNSVA YDCVQLHGGW GYMWEYPIAK
         410        420        430
   AYVDARVQPI YGGTNEIMKE LIAREIVFDK
```

*Fig. 2B*

MCAD (UniProtKB - P11310, SEQ ID NO: 3)

```
          10         20         30         40         50
   MAAGFGRCCR VLRSISRFHW RSQHTKANRQ REPGLGFSFE FTEQQKEFQA
          60         70         80         90        100
   TARKFAREEI IPVAAEYDKT GEYPVPLIRR AWELGLMNTH IPENCGGLGL
         110        120        130        140        150
   GTFDACLISE ELAYGCTGVQ TAIEGNSLGQ MPIIIAGNDQ QKKKYLGRMT
         160        170        180        190        200
   EEPLMCAYCV TEPGAGSDVA GIKTKAEKKG DEYIINGQKM WITNGGKANW
         210        220        230        240        250
   YFLLARSDPD PKAPANKAFT GFIVEADTPG IQIGRKELNM GQRCSDTRGI
         260        270        280        290        300
   VFEDVKVPKE NVLIGDGAGF KVAMGAFDKT RPVVAAGAVG LAQRALDEAT
         310        320        330        340        350
   KYALERKTFG KLLVEHQAIS FMLAEMAMKV ELARMSYQRA AWEVDSGRRN
         360        370        380        390        400
   TYYASIAKAF AGDIANQLAT DAVQILGGNG FNTEYPVEKL MRDAKIYQIY
         410        420
   EGTSQIQRLI VAREHIDKYK N
```

*Fig. 2C*

SCAD (UniProtKB - P16219, SEQ ID NO: 4)

```
            10         20         30         40         50
    MAAALLARAS GPARRALCPR AWRQLHTIYQ SVELPETHQM LLQTCRDFAE
            60         70         80         90        100
    KELFPIAAQV DKEHLFPAAQ VKKMGGLGLL AMDVPEELGG AGLDYLAYAI
           110        120        130        140        150
    AMEEISRGCA STGVIMSVNN SLYLGPILKF GSKEQKQAWV TPFTSGDKIG
           160        170        180        190        200
    CFALSEPGNG SDAGAASTTA RAEGDSWVLN GTKAWITNAW EASAAVVFAS
           210        220        230        240        250
    TDRALQNKGI SAFLVPMPTP GLTLGKKEDK LGIRGSSTAN LIFEDCRIPK
           260        270        280        290        300
    DSILGEPGMG FKIAMQTLDM GRIGIASQAL GIAQTALDCA VNYAENRMAF
           310        320        330        340        350
    GAPLTKLQVI QFKLADMALA LESARLLTWR AAMLKDNKKP FIKEAAMAKL
           360        370        380        390        400
    AASEAATAIS HQAIQILGGM GYVTEMPAER HYRDARITEI YEGTSEIQRL
           410
    VIAGHLLRSY RS
```

Fig. 2D

HADHA (UniProtKB - P40939; SEQ ID NO: 5)

```
            10         20         30         40         50
    MVACRAIGIL SRFSAFRILR SRGYICRNFT GSSALLTRTH INYGVKGDVA
            60         70         80         90        100
    VVRINSPNSK VNTLSKELHS EFSEVMNEIW ASDQIRSAVL ISSKPGCFIA
           110        120        130        140        150
    GADINMLAAC KTLQEVTQLS QEAQRIVEKL EKSTKPIVAA INGSCLGGGL
           160        170        180        190        200
    EVAISCQYRI ATKDRKTVLG TPEVLLGALP GAGGTQRLPK MVGVPAALDM
           210        220        230        240        250
    MLTGRSIRAD RAKKMGLVDQ LVEPLGPGLK PPEERTIEYL EEVAITFAKG
           260        270        280        290        300
    LADKKISPKR DKGLVEKLTA YAMTIPFVRQ QVYKKVEEKV RKQTKGLYPA
           310        320        330        340        350
    PLKIIDVVKT GIEQGSDAGY LCESQKFGEL VMTKESKALM GLYHGQVLCK
           360        370        380        390        400
    KNKFGAPQKD VKHLAILGAG LMGAGIAQVS VDKGLKTILK DATLTALDRG
           410        420        430        440        450
    QQQVFKGLND KVKKKALTSF ERDSIFSNLT GQLDYQGFEK ADMVIEAVFE
           460        470        480        490        500
    DLSLKHRVLK EVEAVIPDHC IFASNTSALP ISEIAAVSKR PEKVIGMHYF
           510        520        530        540        550
    SPVDKMQLLE IITTEKTSKD TSASAVAVGL KQGKVIIVVK DGPGFYTTRC
           560        570        580        590        600
    LAPMMSEVIR ILQEGVDPKK LDSLTTSFGF PVGAATLVDE VGVDVAKHVA
           610        620        630        640        650
    EDLGKVFGER FGGGNPELLT QMVSKGFLGR KSGKGFYIYQ EGVKRKDLNS
           660        670        680        690        700
    DMDSILASLK LPPKSEVSSD EDIQFRLVTR FVNEAVMCLQ EGILATPAEG
           710        720        730        740        750
    DIGAVFGLGF PPCLGGPFRF VDLYGAQKIV DRLKKYEAAY GKQFTPCQLL
           760
    ADHANSPNKK FYQ
```

*Fig. 2E*

```
HADHB (UniProtKB - P55084; SEQ ID NO: 6)

10         20         30         40         50
MTILTYPFKN LPTASKWALR FSIRPLSCSS QLRAAPAVQT KTKKTLAKPN
         60         70         80         90        100
IRNVVVVDGV RTPFLLSGTS YKDLMPHDLA RAALTGLLHR TSVPKEVVDY
        110        120        130        140        150
IIFGTVIQEV KTSNVAREAA LGAGFSDKTP AHTVTMACIS ANQAMTTGVG
        160        170        180        190        200
LIASGQCDVI VAGGVELMSD VPIRHSRKMR KLMLDLNKAK SMGQRLSLIS
        210        220        230        240        250
KFRFNFLAPE LPAVSEFSTS ETMGHSADRL AAAFAVSRLE QDEYALRSHS
        260        270        280        290        300
LAKKAQDEGL LSDVVPFKVP GKDTVTKDNG IRPSSLEQMA KLKPAFIKPY
        310        320        330        340        350
GTVTAANSSF LTDGASAMLI MAEEKALAMG YKPKAYLRDF MYVSQDPKDQ
        360        370        380        390        400
LLLGPTYATP KVLEKAGLTM NDIDAFEFHE AFSGQILANF KAMDSDWFAE
        410        420        430        440        450
NYMGRKTKVG LPPLEKFNNW GGSLSLGHPF GATGCRLVMA AANRLRKEGG
        460        470
QYGLVAACAA GGQGHAMIVE AYPK
```

*Fig. 2F*

THERAPY FOR MITOCHONDRIAL FATTY ACID BETA-OXIDATION AND TRANSPORT DISORDERS

CROSS-REFERENCE TO RELATED APPLICATION

This application is a divisional application of U.S. patent application Ser. No. 16/345,757, filed Apr. 29, 2019, which is the United States national phase of International Application No. PCT/US2017/061712 filed Nov. 15, 2017, and claims priority to U.S. Provisional Patent Application No. 62/422,124 filed Nov. 15, 2016, the disclosure of each of which is hereby incorporated in its entirety by reference.

STATEMENT REGARDING FEDERAL FUNDING

This invention was made with government support under Grant Nos. DK078775 and HD056004 awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 1902403_ST25.txt. The size of the text file is 27,663 bytes, and the text file was created on Apr. 26, 2019.

BACKGROUND

Field of the Invention

Provided herein are methods and compositions for treatment of metabolic disorders, specifically to disorders relating to the β-oxidation pathway and/or fatty acid mitochondrial transport.

Description of Related Art

Many genetic disorders, especially inborn errors of metabolism, are caused by the deficiency in the activity of one particular enzyme causing a biochemical pathway block. A biochemical pathway block causes the accumulation of the enzyme's substrate and the concomitant buildup of alternative metabolites that can be lethal or cause brain damage, within hours in some cases, and deficiency of an enzyme's pathway end product can also be life threatening. Genetic disorders that result from missense mutations resulting in the replacement of an amino acid residue with another causing reduction, or loss, of enzyme function can often render the mutated proteins structurally defective leading to their mis-folding and/or instability of folded mutants. In most cases, mutant enzymes that reach the tertiary and/or quaternary folded/assembled state may have partial activity, but they are usually thermolabile and vulnerable to proteolysis, making fever, strenuous exercise, or other stress factors life threatening decompensation triggers.

Often protein thermostability and vulnerability to proteolysis improve significantly by ligand binding. Ligands that improve protein stability include the protein or enzyme's own substrate, a substrate analog, or its reaction product(s). Other stabilizing ligands also include compositions that bind to allosteric sites, or small chaperone molecules that provide stability through mostly unknown mechanisms. Because the accumulation of an enzyme's substrate is large and often overwhelming, causing accumulation of toxic metabolites, management protocols of some diseases of inborn error of metabolism include omitting sources of substrates or pro-substrates of the deficient enzyme from the diet, if possible.

The acyl-coenzyme A (acyl-CoA) dehydrogenase (ACAD) family of enzymes are structurally and biochemically similar flavoenzymes consisting of 9 known members. Five of the ACADs; very long chain acyl-CoA dehydrogenase (VLCAD), acyl-CoA dehydrogenase 9 (ACAD9), long chain acyl-CoA dehydrogenase (LCAD), medium chain acyl-CoA dehydrogenase (MCAD), and short chain acyl-CoA dehydrogenase (SCAD), catalyze the first step of the spiral pathway with overlapping substrate chain length specificity, where each round shortens the carbon chain length by a 2-carbon unit in the form of acetyl-CoA as the pathway's main product (FIG. 1). Acetyl-CoA enters the tricarboxylic acid cycle for energy generation. The other four ACAD family members; isovaleryl-CoA dehydrogenase (IVD), isobutyryl-CoA dehydrogenase (IBD), short/branched chain (SBCAD), and glutaryl-CoA dehydrogenase (GD), function in the amino acid catabolism pathways.

Very long-chain acyl-CoA dehydrogenase deficiency (VLCADD) is an autosomal recessive metabolic genetic disorder of fatty acid metabolism. Its estimated frequency is at 1:30,000 to 1:100,000 births. Children with early-onset VLCADD present with symptoms within days or weeks after birth. These infants also show signs of hypoglycemia, irritability and lethargy. From ages two or three months to about two years, infants with this form of the disorder will be at risk for hypertrophic cardiomyopathy, abnormal heart rhythms and cardiorespiratory failure. Cardiomyopathy is rare in infancy, but may be life threatening when present. Later-onset VLCADD may present with recurrent episodes of lethargy and/or coma associated with hypoketotic hypoglycemia, during infancy, and hepatomegaly during childhood.

During later childhood and early adulthood, VLCADD patient hypoglycemia becomes less common and patients instead experience periodic attacks of muscle pain and rhabdomyolysis. Affected individuals may begin to experience recurrent metabolic acidosis, sudden respiratory arrest and even cardiac arrest. These symptoms may be associated with cardiomyopathy, lethargy, and coma. Without immediate treatment, such acute episodes may lead to potentially life-threatening complications. Individuals with VLCADD may have fat deposits and hepatomegaly, hypotonia, and/or evidence of cardiomyopathy. There may be hypertrophic or dilated cardiomyopathy. Significant increase in ROS in patients with VLCADD has also been found (unpublished data). Cardiomyopathy may lead to weakening in the force of heart contractions, decreased efficiency in the circulation of blood through the lungs and the rest of the body, and various associated symptoms that may depend upon the nature and severity of the condition, patient age, and other factors.

Medium acyl-CoA dehydrogenase (MCAD) catalyzes the α,β-dehydrogenation of $C_6$- to $C_{10}$-CoA ester substrates. MCAD deficiency is another fatty acid β-oxidation defect that rivals PKU in being the highest incidence among all metabolic genetic disorders. MCAD K304E is the most common (>90%) among all MCAD variants identified and is a thermally labile protein. Deficiency in the trifunctional protein (TFP) components' activities is another life threatening hereditary metabolic disorders caused by mutations in the HADHA or HADHB genes.

TFP is a hetero-octamer composed of four α- and four β-subunits, which the product from the VLCAD reaction, trans-2-enoyl-CoA, targets for the next three steps in the cycle. TFP catalyzes these three remaining steps of the β-oxidation cycle, with the a subunit (encoded by the HADHA gene) performing two functions, namely the hydration of trans-2-enoyl-CoA and the dehydrogenation of 3-hydroxyacyl CoA, and the β-subunit (encoded by the HADHB gene) performing the long-chain 3-ketoacyl-CoA thiolase (LCKAT) function. Defects in LCHAD and LCKAD, or TFP function, caused by mutations in the HADHA or HADHB genes, are life threatening hereditary metabolic disorders, with serious morbidity and mortality.

Current interventions for conditions caused by a mutation in an enzyme of the β-oxidation pathway and/or fatty acid mitochondrial transport are extremely limited, and effective therapeutic interventions for such conditions are needed.

SUMMARY

Provided herein is a method of treating a disorder caused by a mutation in any of the enzymes and/or proteins of the β-oxidation pathway and/or fatty acid mitochondrial transport in a patient in need thereof, comprising administering to the patient an effective amount of an inhibitor of activity of an enzyme of the β-oxidation pathway downstream in the β-oxidation pathway of the enzyme having the mutation, thereby increasing activity of the enzyme of the β-oxidation pathway of fatty acid mitochondrial transport having the mutation, wherein the product of the enzyme having the mutation stabilizes that unstable enzyme, or one or more substrates or products of the downstream enzyme binds allosterically to the mutant enzyme and stabilize that unstable enzyme.

Also provided herein is a method of increasing activity of a protein and/or enzyme of the β-oxidation pathway and/or fatty acid mitochondrial transporter protein/enzyme, the protein and/or enzyme having a mutation resulting in loss of its activity or stability, in a patient in need thereof, comprising administering to the patient an effective amount of an inhibitor of activity of an enzyme of the β-oxidation pathway downstream in the β-oxidation pathway of the enzyme having the mutation, thereby increasing activity of the upstream enzyme of the β-oxidation pathway and/or a fatty acid mitochondrial transporter protein/enzyme having a mutation, wherein the product of the enzyme having the mutation binds back and stabilizes that protein/enzyme.

BRIEF DESCRIPTION OF THE DRAWINGS

The following drawings are for the purpose of illustration and description only and are not intended as a definition of the limit of the invention.

FIGS. 2A-2F provide exemplary and non-limiting amino acid sequences for enzyme members of the human β-oxidation pathway, including: VLCAD (FIG. 2A), LCAD (FIG. 2B); MCAD (FIG. 2C); SCAD (FIG. 2D); TFP-α subunit (HADHA) (FIG. 2E); and TFP-β subunit (FIG. 2F).

DETAILED DESCRIPTION

Figure 1:
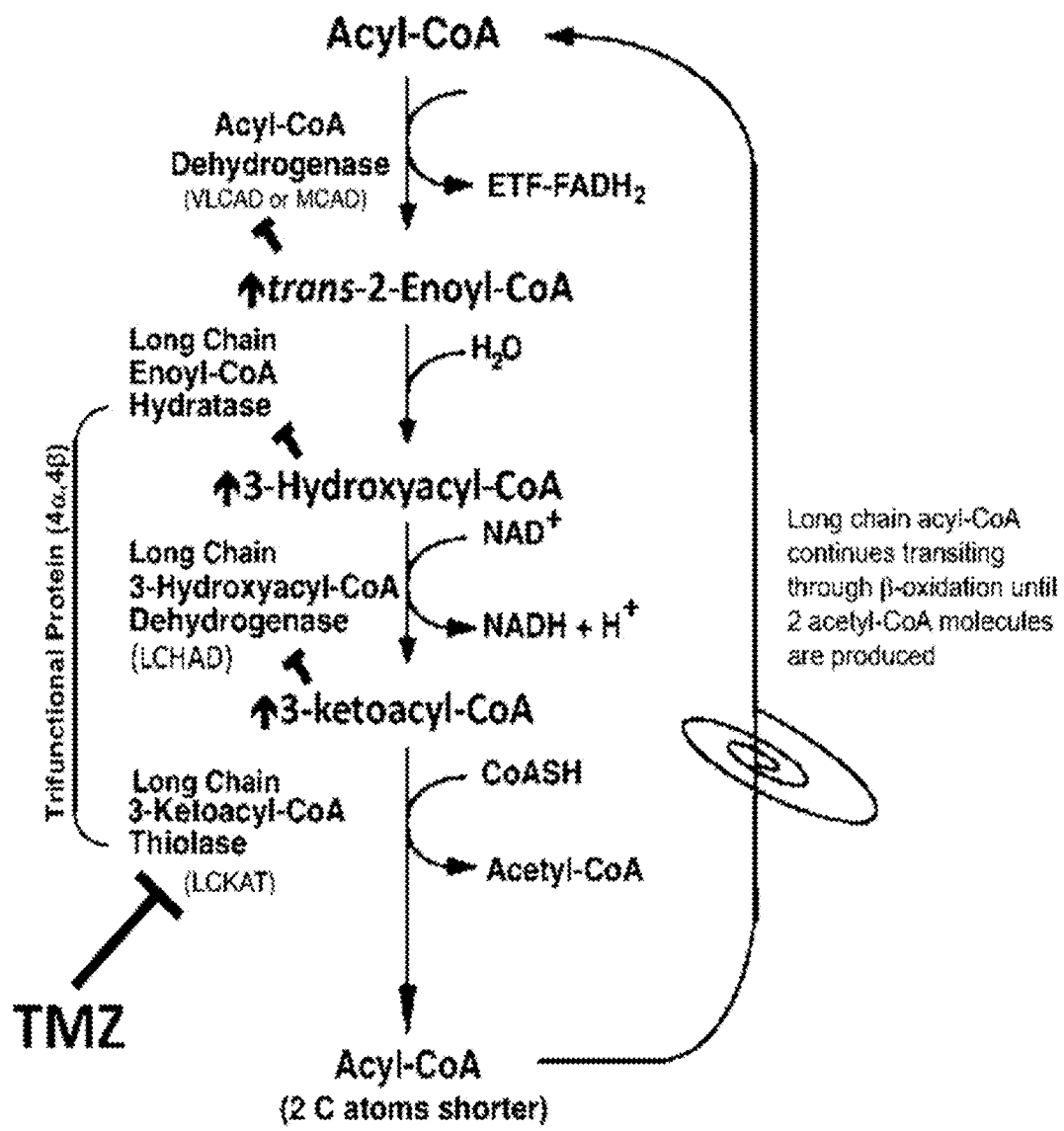
FIG. 1. The β-oxidation pathway. Five known enzymes catalyze the first step of the pathway with overlapping substrate chain length specificity. The rest of the pathway reactions are carried out by the Trifunctional Protein complex, TFP, which consists of four α and four β subunits carrying out three different functions.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

As used herein, the terms "comprising," "comprise" or "comprised," and variations thereof, in reference to elements of an item, composition, apparatus, method, process, system, claim etc. are intended to be open-ended, meaning that the item, composition, apparatus, method, process, system, claim etc. includes those elements and other elements can be included and still fall within the scope/definition of the described item, composition, apparatus, method, process, system, claim etc. As used herein, "a" or "an" means one or more. As used herein "another" may mean at least a second or more.

As used herein, the terms "patient" or "subject" refer to members of the animal kingdom, including, but not limited to human beings.

As used herein, "alkyl" refers to straight, branched chain, or cyclic hydrocarbon (hydrocarbyl) groups including, for example, from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" refer to divalent alkyl and divalent substituted alkyl, respectively, including, without limitation, ethylene (—$CH_2$—$CH_2$—). "Optionally substituted alkylene" refers to alkylene or substituted alkylene.

"Aryl," alone or in combination refers to an aromatic monocyclic or bicyclic ring system such as phenyl or naphthyl. "Aryl" also includes aromatic ring systems that are optionally fused with a cycloalkyl ring. A "substituted aryl" is an aryl that is independently substituted with one or more substituents attached at any available atom to produce a stable compound, wherein the substituents are as described herein. "Optionally substituted aryl" refers to aryl or substituted aryl. "Arylene" denotes divalent aryl, and "substituted arylene" refers to divalent substituted aryl. "Optionally substituted arylene" refers to arylene or substituted arylene.

"Heteroatom" refers to N, O, P and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with N, O, P or S.

"Substituted" or "substitution" refer to replacement of a hydrogen atom of a molecule or another atom or group with one or more different groups, such as halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, nitro, sulfato. Examples of substitutions are isosteric substitutions as described herein.

"Cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or hetroaryl ring. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein. "Cycloalkylene" refers to divalent cycloalkyl. The term "optionally substituted cycloalkylene" refers to cycloalkylene that is substituted, e.g., with 1, 2 or 3 substituents, attached at any available atom to produce a stable compound, wherein the substituents are as described herein.

A "disorder caused by a mutation in an enzyme of the β-oxidation pathway and/or fatty acid mitochondrial transport," is a condition, disease, defect, disorder, typically a congenital disorder or birth defect, that results from lowered activity of an enzyme of the β-oxidation pathway, such as an ACAD (VLCAD, LCAD, MCAD, or SCAD), the TFP, carnitine palmitoyltransferase I (CPT I), carnitine-acycarnitine translocase, and/or carnitine palmitoyltransferase II (CPT II). In aspects, the mutation is a missense mutation. The mutation results in an unstable or labile protein that is stabilized in the presence of and/or by a product(s)/substrate(s) of the enzyme. The stabilizing effect induced by binding of the product(s)/substrate(s) to the enzyme results in overall increase in enzyme activity, that is, the phenotypic effect of the enzyme, in a cell, e.g. of a patient. An enzyme substrate is the molecule upon, which the enzyme acts producing a product, which in the chemical sense can be a substrate since the reaction can run in reverse in some cases. The mutation typically is a missense mutation, such as arise from single nucleotide substitutions that changes the amino acid residue to one that disrupt the structural contribution of the normal residue to enzyme structure and/or function. The change can be a 3-nucleotide (or multiples of 3 to keep the protein code inframe) insertion or deletion, and the methods described herein are considered effective so long as activity of the mutant enzyme increases upon binding of the substrate in the enzyme assay described.

Provided herein are methods of stabilizing members of the β-oxidation pathway having mutations that are stabilized by ligand binding. In particular, provided herein are methods for treating a disorder caused by a mutation, for example and without limitation a missense mutation, in any of the enzymes/proteins of the β-oxidation pathway and/or fatty acid mitochondrial transport in a patient in need thereof.

Screening for small chaperone molecules that bind enzymes at sites away from their catalytic sites to stabilize structurally compromised mutants has been a major rational for drug development, stabilizing molecules, such as the enzyme's own reaction product or substrates/products of the downstream pathway steps that are already in situ would provide such stabilizing effect only if they are present at proper concentrations to bind to the defective enzyme/protein.

The above rational is the basis of the concept presented where enzymes that catalyze the pathway's downstream reactions to the defective mutant are targeted for inhibitory drug development with the aim of accumulating their substrate(s)/product(s) that may in turn bind to the pathway's upstream unstable variant enzyme (or subunit in a multi-enzyme complex). The downstream substrate(s)/product(s) may bind at the enzyme variant active site, or possibly allosteric site(s), to confer enough stability for improved function, thus alleviating the genetic disorder phenotype.

The protective effect conferred by ligand binding against proteolytic digestion has been a known phenomenon (Mohsen et al., 1995). The protective effect conferred by ligand binding against protein thermal unfolding has been demonstrated Nasser, I., et al. (2004). Thermal unfolding of medium-chain acyl-CoA dehydrogenase and iso(3)valeryl-CoA dehydrogenase: study of the effect of genetic defects on enzyme stability. *Biochim Biophys Acta* 1690, 22-32), effective methods of accomplishing that feat are not. For ACADs, in vitro thermal stability data with purified wild type recombinant human MCAD have shown that $C_8$-CoA binding induces 5-11° C. protection against thermal unfolding with the protection of the substrate analog 2-aza-$C_8$-CoA also occurring, but not as impressive (Nasser et al., 2004). Similarly, the effect of $C_5$-CoA binding on IVD, was in the 4-5° C. range. In the case of the two most common MCAD and IVD patient mutants, MCAD K304E and IVD A282V, the corresponding substrate/product provided thermally similar to the corresponding wild type. CoA persulfide, a substrate analog that binds tightly to certain ACADs, and confers protection to IVD against trypsin digestion. All members of the ACAD family of enzymes, TFP subunits, and mitochondrial transport proteins, can be safely presumed to behave similarly in the presence of their corresponding substrate/product. By stabilizing the mutant enzymes, diseases or conditions in patients resulting from deficiency of the mutant enzyme can be effectively treated. Thus, ACAD deficiencies and deficiencies in enzyme members of the β-oxidation pathway can be effectively treated by blocking, at least temporarily, LCKAT activity in a patient. When further combined with an activator of the β-oxidation pathway, such as a Peroxisome Proliferator-Activated Receptor delta (PPARδ) agonist, a β-oxidation pathway in a patient in which at least one enzyme member of the pathway is mutated, e.g., with a missense mutation, further enhanced activity of the mutant enzyme is observed.

FIGS. 2A-2F provide exemplary amino acid sequences for enzyme members of the human β-oxidation pathway, including: VLCAD (example, FIG. 2A) and its isoenzymes, LCAD (FIG. 2B); MCAD (FIG. 2C); SCAD (FIG. 2D); TFP-α subunit (HADHA) (FIG. 2E); and TFP-β subunit (FIG. 2F). Missense mutations of those amino acid sequences are published. Exemplary missense mutations include more than 65 of VLCAD (See Table 1, Uniprot Accession No. D43682, Uniprot Accession No. P49748, and Pena et al., 2016), MCAD mutants including the well known K304E mutant (K329E, precursor numbering, shown in SEQ ID NO: 3) (Gregersen et al., 2008); E510Q of HADHA (or E474Q in reference to the mature HADHA protein).

TABLE 1

| Publication | Nucleotide Mutation | Residue position (Precursor numbering) (VLCAD Accession: P49748; see FIG. 2A) | Residue change (Reported) |
|---|---|---|---|
| Andresen et al., 1999 | 128G > A | | G3D |
| Watanabe, et al., 2000 | 194C > T | P65 | P65L |
| Zhang et al., 2014 | 215C > T | S72 | S72F |
| (Unpublished) | 439C > T | P147 | P147S |
| Andresen et al., 1999 | 473C > A | T118 | T118N |
| Andresen et al., 1999 | 476A > G | Q119 | Q119R |
| Laforet et al., 2009 | 455G > A | G152D | |
| Boneh et al., 2006 | 481G > A | A161T | A121T |
| (Vockley, Unpublished) | 482C > T | A161V | |
| Andresen et al., 1999 | 520G > A | V134 | V134M |
| Andresen et al., 1999 | 553G > A | G145 | G145S |
| (Vockley, Unpublished) | 622G > A | G208R | G168R |
| Mathur et al., 1999 | 637G > C | A213 | A173P |
| (Mohsen, Unpublished) | 520G > A | V174M | |
| Andresen et al., 1999 | 652G > A | E218 | E178K |
| Laforet et al., 2009 | 535G > T | | G179W |
| Andresen et al., 1999 | 728T > G | L243 | L203R |
| Mathur et al., 1999 | A739G | K247 | K207E |
| Andresen et al., 1999 | 740A > C | K247 | K207T |
| Zhang et al., 2014 | c.637G > A | A213 | A213T |
| Boneh et al., 2006 | 753-2A > C | | |
| Andresen et al., 1999; Goetzman et al., 2007 | 779C > T | T260 | T220M |
| Zhang et al., 2014 | 664G > C | G222 | G222R |
| (Vockley, Unpublished) | 689C > T | T230I | T230I |
| Watanabe et al., 2000 | 739A > C transversion | | (K247Q) |

TABLE 1-continued

| Publication | Nucleotide Mutation | Residue position (Precursor numbering) (VLCAD Accession: P49748; see FIG. 2A) | Residue change (Reported) |
|---|---|---|---|
| Laforet et al., 2009; Andresen et al., 1996A, 1999 | 842C > A | | A281D |
| (Vockley, Unpublished) | 848T > C | V283A | |
| (Vockley, Unpublished) | 865G > A | G289R | G289R |
| Andresen et al., 1999 | 869G > A | | G250D |
| Andresen et al., 1999 | 881G > A | | G254E |
| Andresen et al., 1999 | 897G > T | | K259N |
| (Vockley, Unpublished) | 898A > G | M300V | M300V |
| Andresen et al., 1999 | 950T > C 956C > A | | V277A |
| Andresen et al., 1999 | 1054A > G | | M312V |
| Andresen et al., 1999 | 1096C > T | | R326C |
| Antunes et al., 2013 | 1097G > A | R366 | R326H |
| Boneh et al., 2006; Andersen et al., 1999 | 1117A > T | I373 | I333F |
| (Unpublished) | 1001T > G | M334R | M334R |
| (Unpublished) | 1066A > G | I356V | I356V |
| (Unpublished) | 1076C > T | A359V | A359V |
| Boneh et al., 2006 | 1153C > T | R385 | R345W |
| Andresen et al., 1999 | 1213G > C | | D365H |
| (Unpublished) | 1146G > C | K382N | K382N |
| Zhang et al., 2014 | 1310T > C | M437 G439D | M437T |
| Boneh et al., 2006; Manthur et al., 1999; Andersem et al., 1999 | 1322G > A | G441 | G401D |
| Andresen et al., 1999 | 1358G > A | | R413Q |
| Andresen et al., 1999 | 1360G > A | | D414N |
| Mathur et al., 1999 | 1372T > C | | F418L |
| | 1258A > C | I420L | |
| Andresen et al., 1999 | 1388G > A | | G423E |
| Andresen et al., 1999; Goetzman et al., 2007 | 1405C > T | | R429W |
| Andresen et al., 1999 | 1406G > A | | R429Q |
| Pons et al., 2000 | 1430G > A | | C437Y |
| Zhang et al., 2014; Boneh et al., 2006; Andersen et al., 1999 | 1349G > A | R450 | R450H |
| Andresen et al., 1999; Goetzman et al., 2007 | 1505T > C | | L462P |
| Zhang et al., 2014 | 1396G > T | D466 | D466Y |
| Laforet et al., 2009 | 1613G > C | | R538P |
| Mathur et al., 1999 | 1600G > A | | E454K |
| Aliefendioğlu et al., 2007; Andresen et al., 1999 | 1367G > A | | R456H |
| Pons et al, 2000; Andresen et al., 1999 | 1375C > T | R459W | R459W |
| Laforet et al., 2009 | 1376G > A | | R459Q |
| (Unpublished) | 1532G > A | R511Q | R511Q |
| (Vockley, Unpublished) | 1619T > C | L540P | |
| Andresen et al., 1999 | 1804C > A | | L562I |
| Mathur et al., 1999 | 1844G > A | | R575Q |
| (Mohsen, Unpublished) | 1825G > A | E609K | |
| Mathur et al., 1999 | 1844G > A | R615Q | R615Q |
| (Unpublished) | 1837C > G | R613G | R613G |

VLCAD is a homodimeric flavoenzyme and is the enzyme that catalyzes the first step in the fatty acid β-oxidation spiral where the long chain acyl-CoA substrate is converted to the trans-2-enoyl-CoA product. Specifically, VLCAD catalyzes the α,β-dehydrogenation of $C_{14}$-$C_{22}$-CoA ester substrates. VLCAD deficiency is an inborn error of metabolism caused by one homozygous mutation, or two (different one in each allele, example FB833, V174M and E609K used in this study) heterozygous, of a high number of mutations that has been identified and essentially cause life threatening decrease in mitochondrial long chain fatty acid β-oxidation in severe cases. Among the mutations identified in the VLCAD gene, more than 65 have been missense mutations that cause different degrees of instabilities, with VLCAD A283V mutant being more common than others (See Table 1 and Pena et al., 2016). Since VLCAD is the entry enzyme into the pathway, complete deficiency of VLCAD essentially shuts down most of the long chain fatty acid mitochondrial-oxidation, an essential energy source and provider of the medium chain acyl-CoAs that continue to complete the conversion of the fatty acid to the acetyl-CoA end product. VLCAD is most active when $C_{16}$-CoA is used as the substrate, which is converted to trans-2-enoyl-CoA, which is released upon the transfer of electrons to the second substrate, the electron transfer flavoprotein (ETF). The trans-2-enoyl-CoA product can still bind to the oxidized VLCAD inhibiting the reaction and so must be cleared by the next step in the pathway, which is catalyzed by the long chain enoyl-CoA hydratase. This latter enzyme, however, is part of the Trifunctional Protein (TFP) complex, which consists of 4 α-subunits and 4 β-subunits. The TFP also includes 3-hydroxyacyl-CoA dehydrogenase and the long chain 3-ketoacyl-CoA thiolase. Since substrate channeling to the various active sites within the complex is expected, inhibiting any of the activities of the complex components is likely to negatively affect the other two.

Trimetazidine (TMZ, 1-(2,3,4-trimethoxybenzyl)piperazine, PubChem CID: 21109; molar mass 266.336 g/mol):

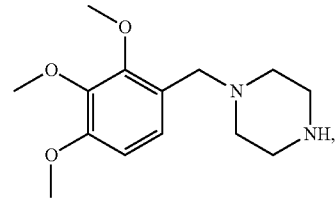 [SMILES: COc1ccc(CN2CCNCC2)c(OC)c1OC]

is an inhibitor of the downstream "last" reaction in the β-oxidation cycle catalyzed by LCKAT. Here, TMZ is used to bind to/inhibit LCKAT activity leading to the stabilization of LCKAT itself, and the upstream β-oxidation cycle components including, LCAHD, VLCAD, and MCAD, and it is expected to stabilize other members of the TFP complex(es) and mitochondrial fatty acid transport proteins, and so can be used to treat deficiencies of the mitochondrial β-oxidation cycle and also deficiencies in mitochondrial membrane fatty acid transport proteins, e.g., Carnitine palmitoyltransferase I (CPT I) and Carnitine palmitoyltransferase 2 (CPT II). TMZ is approved by the FDA in the USA and elsewhere for use in angina pectoris due to ischemia of the heart muscle. Its generic version is manufactured globally and is available in 90 countries. Compared to conventional therapy, TMZ is reported to have shown significant improvements in non-ischemic and ischemic cardiomyopathy. The mechanism of the TMZ effect results from the shift of cardiac energy fulfillment from fatty acid oxidation to glucose oxidation. Since ~80% of cardiac cells rely on fatty acid as a source of energy, by shifting reliance of cardiac cells for energy from fatty acids to glucose, oxygen demand is decreased.

TMZ derivatives having the ability to inhibit LCKAT activity also may be used to inhibit LCKAT activity, e.g. in a cell or a patient, thereby having the same effect as TMZ in causing accumulation of a substrate of an upstream mutated enzyme, thereby stabilizing the enzyme. TMZ and derivatives thereof are disclosed in U.S. Pat. No. 5,283,246, incorporated herein by reference. Non-limiting examples of other potentially useful compounds with the TMZ scaffold that may offer advantage(s) over TMZ include TMZ-NH (4-(2,2,5,5-tetramethylpyrrolinyl-3)-1-(2,3,4-trimethoxybenzyl)piperazine) and TMZ-φNH (4-(2,2,5,5-tetramethyl-4-phenylpyrrolinyl-3-)-1-(2,3,4-trimethoxybenzyl) piperazine, see below), as they have shown anti-ROS activity and other improved parameters in ischemic heart disease parameters that are pertinent to the application herein. TMZ derivatives include 4-substituted piperazine TMZ derivatives (structure 1),

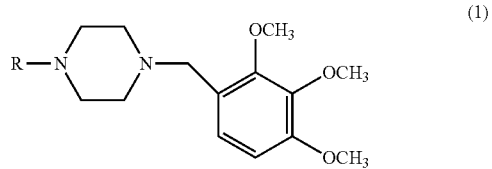

(1)

where R is, for example, a 5 to 7 member hydrocarbon or heterocyclic group substituted with from 1 to 3 N, O, and/or S hetero-atoms, and in one example is saturated, and in another is unsaturated or aromatic, and in a further example comprises from 1 to 3 N atoms, for example a pyrrolinyl group or a substituted pyrollinyl group, substituted with a $C_1$-$C_6$ hydrocarbon, such as a phenyl or a $C_1$-$C_6$ alkyl group, such as 2,2,5,5-tetramethylpyrrolinyl group (TMZ-NH):

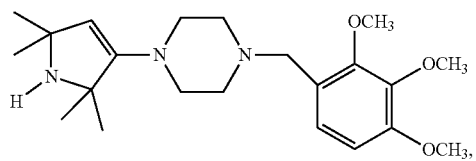 [SMILES: COc1ccc(CN2CCN(C3=CC(C)(C)NC3(C)C)CC2)c(OC)c1OC]

or 2,2,5,5-tetramethyl-4-phenylpyrrolinyl group, (TMZ-φNH):

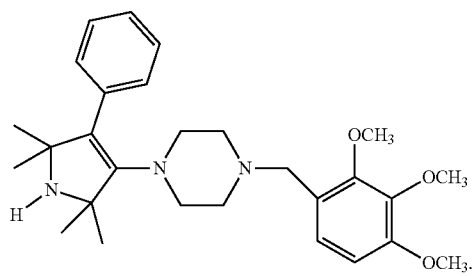 [SMILES: COc1ccc(CN2CCN(C3=C(c4ccccc4)C(C)(C)NC3(C)C)CC2)c(OC)c1OC]

Exemplary TMZ derivatives are described in Kutala, V. K., et al. (2006) (Attenuation of myocardial ischemia-reperfusion injury by trimetazidine derivatives functionalized with antioxidant properties. *J Pharmacol Exper Therapeut* 317 (3):921-928); Ancerewicz, J., et al. (1998) (Structure-property relationships of trimetazidine derivatives and model compounds as potential antioxidants. *Free Rad. Biol Med* 25(1):113-120); and Kálai, T., et al. (2006) (Structure-activity studies on the protection of Trimetazidine derivatives modified with nitroxides and their precursors from myocardial ischemia-reperfusion injury. *Bioorg Medicinal Chem* 14:5510-5516). TMZ derivatives include isosteres of TMZ, in which one or more group of structure 1, above, is substituted with a similar group, resulting in a bioisostere molecule with the same overall therapeutic effect, e.g., inhibition of LCKAT, but potentially with attenuated toxicity, activity and/or pharmacokinetics. Non-limiting, and exemplary isosteric substitutions include, as groups: H, deuterium, and F; Me, $NH_2$, OH, F, and Cl; Cl, $PH_2$, SH, and CN; Br, isopropyl, and $CF_3$; I, tert-butyl, and $CF_3$; $CH_2$, NH, O, and S; $CO_2R$, CONHR, COSR, and $COCH_2R$; —CH=, —N=, and —S—; C and Si; phenyl, pyridyl, thiophene, and 4-fluorophenyl; —OH, —F, and -OMe; and —O— and —$CF_2$—. Additional isosteric substitutions are known and can result in a compound with similar activity to TMZ.

Provided herein according to one aspect of the invention is a method of treating a disorder caused by a mutation, e.g., a missense mutation, in an enzyme of the β-oxidation pathway or fatty acid transport into mitochondria, in a patient in need thereof, comprising inhibiting activity of an enzyme of the β-oxidation pathway downstream in the β-oxidation pathway to the enzyme having the missense mutation, thereby increasing activity of the an enzyme of the β-oxidation pathway or fatty acid transport into mitochondria having the missense mutation. In one aspect, the activity of an enzyme of the β-oxidation pathway is inhibited by TMZ, a derivative thereof, a pharmaceutically acceptable salt thereof, or a pharmaceutically-acceptable ester thereof. In another aspect, the enzyme of the β-oxidation pathway downstream in the β-oxidation pathway to the enzyme having the missense mutation is the TFP subunit LCKAT (encoded by HADHB).

For therapeutic use, salts of the compounds are those wherein the counter-ion is pharmaceutically acceptable (pharmaceutically-acceptable salts). However, salts of acids and bases which are non-pharmaceutically acceptable may also find use, for example, in the preparation or purification of a pharmaceutically acceptable compound.

Pharmaceutically acceptable salts as mentioned herein are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely the salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. The term "addition salt" as used hereinabove also comprises the solvates which the compounds described herein are able to form. Such solvates are for example hydrates, alcoholates, and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen.

Pharmaceutically acceptable counterions, such as, without limitation, chloro, bromo, iodo, trifluoroacetate, and acetate can be introduced using ion exchange resins.

"Pharmaceutically acceptable esters" includes those derived from compounds described herein that are modified to include a carboxyl group. An in vivo hydrolysable ester is an ester, which is hydrolyzed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety may include from 1 to 18 carbon atoms, such as from 1 to 6 carbon atoms, or from 1 to 4 carbon atoms. Any cycloalkyl moiety present in such esters advantageously contains from 3 to 6 carbon atoms. Any aryl moiety present in such esters advantageously comprises a phenyl group that is optionally substituted. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted. Additional pharmaceutically acceptable esters include aliphatic L-amino acid esters such as leucyl, isoleucyl and valyl.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art.

Protected derivatives of the disclosed compounds also are contemplated. Many suitable protecting groups for use with the disclosed compounds are broadly-known in the art. In general, protecting groups are removed under conditions which will not affect the remaining portion of the molecule. These methods are well known in the art and include acid hydrolysis, hydrogenolysis and the like. One method involves the removal of an ester, such as cleavage of a phosphonate ester using Lewis acidic conditions, such as in TMS-Br mediated ester cleavage to yield the free phosphonate. A second method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with any of the large number of broadly-available publications. When an amine is deprotected, the resulting salt can readily be neutralized to yield the free amine. Similarly, when an acid moiety, such as a phosphonic acid moiety is unveiled, the compound may be isolated as the acid compound or as a salt thereof.

According to one aspect, amine side chains are protected using protective groups, for example and without limitation by acylation. Protecting groups are known in the art and include, without limitation: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), 1-(4,4-dimethyl-2,6-dioxacyclohexylidene)ethyl (Dde), diathiasuccinoyl (Dts), benzothiazole-2-sulfonyl (Bts), dimethoxytrityl (DMT) and monomethoxytrityl (MMT) groups. A protecting group also includes acyl groups, such as acetyl groups, for example, as described.

Unless indicated otherwise, for instance in a structure, all compounds and/or structures described herein comprise all possible stereoisomers, individually or mixtures thereof. The compound and/or structure may be an enantiopure preparation consisting essentially of an (−) or (+) enantiomer of the compound, or may be a mixture of enantiomers in either equal (racemic) or unequal proportions.

The compounds typically are administered in an amount and dosage regimen to treat a condition or symptom of a condition in a patient caused by a missense mutation in an enzyme of the β-oxidation pathway. The compounds may be administered in any manner that is effective to treat, mitigate or prevent a condition or symptom of a condition in a patient caused by a missense mutation in an enzyme of the β-oxidation pathway. Examples of delivery routes include, without limitation: topical, for example, epicutaneous, inhalational, enema, ocular, otic and intranasal delivery; enteral, for example, orally, by gastric feeding tube, or rectally; and parenteral, such as, intravenous, intraarterial, intramuscular, intracardiac, subcutaneous, intraosseous, intradermal, intrathecal, intraperitoneal, transdermal, iontophoretic, transmucosal, epidural and intravitreal, with oral, intravenous, intramuscular and transdermal approaches being preferred in many instances.

As indicated above, and in the examples, a useful dosage of the inhibitor of the activity of an enzyme of the β-oxidation pathway ranges from, for example 10 μg to 10 mg/Kg body weight/day, and in one aspect ranges from 0.05 mg to 0.5 mg/Kg body weight/day. Different drug products will have different specific activities and therefore dosage is optimized for any particular drug product. Of note, the exemplary dosage range for TMZ ranges from 0.05 mg to 0.5 mg/Kg body weight/day, which is lower that a typical dosage of that compound for treatment of ischemic heart disease. An "effective amount" of the compound or composition described herein is an amount effective in a dosage regimen (amount of the compound and timing and mode of delivery), to achieve a desired end-point, such as maintaining concentrations at a site of treatment within a range effective to achieve an outcome. Suitable outcomes include overcoming a metabolic block in a patient caused by a missense mutation in an enzyme of the β-oxidation pathway, or improvement of one or more symptoms of a condition caused by a missense mutation in an enzyme of the β-oxidation pathway, for example as described herein. In aspects, the compositions can be given to a patient in a pulsed fashion in which an amount of the compound is provided that is effective to cause a partial or complete block in the β-oxidation pathway, followed by a time period in which the amount of the compound is reduced such that the block, e.g. of the 3-ketoacyl-CoA thiolase of the TFP, is released, permitting the β-oxidation pathway to proceed to its end (where 3-ketoacyl-CoA is converted to acyl-CoA by the 3-ketoacyl-CoA thiolase activity of the TFP). The amount of the compound administered to a patient, and the timing of the block, and release of the block, can be adjusted to an individual patient and/or to the specific mutation present in a patient.

The compounds may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms include: intravenous, intramuscular, or intraperitoneal solutions, oral tablets or liquids, topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution.

Therapeutic/pharmaceutical compositions are prepared in accordance with acceptable pharmaceutical procedures, such as described in *Remington: The Science and Practice of Pharmacy*, 21st edition, ed. Paul Beringer et al., Lippincott, Williams & Wilkins, Baltimore, Md. Easton, Pa. (2005) (see, e.g., Chapters 37, 39, 41, 42 and 45 for examples of powder, liquid, parenteral, intravenous and oral solid formulations and methods of making such formulations).

In aspects, the compounds or compositions are co-administered with one or more additional therapeutic agents. In one aspect, the additional therapeutic agent is a Peroxisome Proliferator-Activated Receptor delta (PPARδ) agonist; that is, a drug that acts on PPARδ to modulate or increase, PPARδ activity. In one example, the PPARδ agonist is GW 501516 (2-[2-methyl-4-[[4-methyl-2-[4-(trifluoromethyl)phenyl]-1,3-thiazol-5-yl]methylsulfanyl]phenoxy]acetic acid), having the structure:

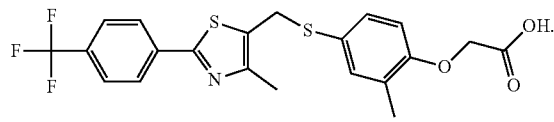 [SMILES: Cc1cc(SCc2sc(-c3ccc(C(F)(F)F)cc3)nc2C)ccc1OCC(=O)O]

Certain PPARδ agonists are available commercially from Mitobridge of Cambridge, Mass. Further, United States Patent Application Publication Nos. 20160023991, 20170226154, 20170304255, and 20170305894, incorporated herein by reference for their disclosure of PPARδ agonists, disclose a large number of PPARδ agonists, including, without limitation: 6-(2-((N-isopropyl-[1,1'-biphenyl]-4-carboxamido)methyl)phenoxy)hexanoic acid; ethyl 6-(2-(1-(4-bromo-N-cyclopropylbenzamido)-2-(tert-butylamino)-2-oxoethyl)phenoxy)hexanoate; ethyl 6-(2-(2-(tert-butylamino)-1-(N-cyclopropyl-[1,1'-biphenyl]-4-carboxamido)-2-oxoethyl)phenoxy)hexanoate; ethyl 6-(2-(2-amino-1-(N-cyclopropyl-[1,1'-biphenyl]-4-carboxamido)-2-oxoethyl)phenoxy)hexanoate; 6-(2-(2-amino-1-(N-cyclopropyl-[1,1'-biphenyl]-4-carboxamido)-2-oxoethyl)phenoxy)hexanoic acid; 6-(2-(2-(tert-butylamino)-1-(N-cyclopropyl-[1,1'-biphenyl]-4-carboxamido)-2-oxoethyl)phenoxy)hexanoic acid; 6-(2-((N-cyclopropyl-[1,1'-biphenyl]-4-carboxamido)methyl)phenoxy)hexanoic acid; N-(2-amino-1-(2-((6-(hydroxyamino)-6-oxohexyl)oxy)phenyl)-2-oxoethyl)-N-cyclopropyl-[1,1'-biphenyl]-4-carboxamide; 6-(2-((N-cyclopropyl-4-(pyridin-4-yl)benzamido)methyl)phenoxy)hexanoic acid; 6-(2-((N-cyclopropyl-4-(pyridin-3-yl)benzamido)methyl)phenoxy)hexanoic acid; 6-(2-((N-cyclopropyl-4-(1H-pyrazol-4-yl)benzamido)methyl)phenoxy)hexanoic acid; 6-(2-((N-cyclopropyl-4-(furan-2-yl)benzamido)methyl)phenoxy)hexanoic acid; 6-(2-((N-cyclopropyl-4-(furan-3-yl)benzamido)methyl)phenoxy)hexanoic acid; 6-(2-((N-cyclopropyl-4-(thiophen-2-yl)benzamido)methyl)phenoxy)hexanoic acid; 6-(2-((N-cyclopropyl-4-(thiophen-3-yl)benzamido)methyl)phenoxy)hexanoic acid; 6-(2-((N-benzyl-[1,1'-biphenyl]-4-carboxamido)methyl)phenoxy)hexanoic acid; 6-(2-((N-benzyl-4-(pyridin-3-yl)benzamido)methyl)phenoxy)hexanoic acid; 6-(2-((N-benzyl-4-(pyridin-4-yl)benzamido)methyl)phenoxy)hexanoic acid; 6-(2-((N-benzyl-4-(1H-pyrazol-4-yl)benzamido)methyl)phenoxy)hexanoic acid; 6-(2-((N-benzyl-4-(thiophen-2-yl)benzamido)methyl)phenoxy)hexanoic acid; 6-(2-((N-benzyl-4-(furan-3-yl)benzamido)methyl)phenoxy)hexanoic acid; 6-(2-((N-benzyl-4-(furan-2-yl)benzamido)methyl)phenoxy)hexanoic acid; 6-(2-((N-benzyl-4-(thiophen-3-yl)benzamido)methyl)phenoxy)hexanoic acid; N-benzyl-N-(2-((6-(hydroxyamino)-6-oxohexyl)oxy)benzyl)-4-(pyridin-4-yl)benzamide; N-benzyl-N-(2-((6-(hydroxyamino)-6-oxohexyl)oxy)benzyl)-[1,1'-biphenyl]-4-carboxamide; N-benzyl-N-(2-((6-(hydroxyamino)-6-oxohexyl)oxy)benzyl)-4-(pyridin-3-yl)benzamide; N-benzyl-N-(2-((6-(hydroxyamino)-6-oxohexyl)oxy)benzyl)-4-(1H-pyrazol-4-yl)benzamide; N-benzyl-N-(2-((6-(hydroxyamino)-6-oxohexyl)oxy)benzyl)-4-(thiophen-2-yl)benzamide; N-benzyl-4-(furan-2-yl)-N-(2-((6-(hydroxyamino)-6-oxohexyl)oxy)benzyl)benzamide; N-benzyl-4-(furan-3-yl)-N-(2-((6-(hydroxyamino)-6-oxohexyl)oxy)benzyl)benzamide; 6-(2-((N-(sec-butyl)-[1,1'-biphenyl]-4-carboxamido)methyl)phenoxy)hexanoic acid; N-benzyl-N-(2-((6-(hydroxyamino)-6-oxohexyl)oxy)benzyl)-4-(thiophen-3-yl)benzamide; 6-(2-((N-(sec-butyl)-4-(pyridin-3-yl)benzamido)methyl)phenoxy)hexanoic acid; 6-(2-((N-(sec-butyl)-4-(pyridin-4-yl)benzamido)methyl)phenoxy)

hexanoic acid; 6-(2-((N-(sec-butyl)-4-(1H-pyrazol-4-yl)benzamido)methyl)phenoxy)hexanoic acid; 6-(2-((N-(sec-butyl)-4-(furan-2-yl)benzamido)methyl)phenoxy)hexanoic acid; 6-(2-((N-(sec-butyl)-4-(furan-3-yl)benzamido)methyl)phenoxy)hexanoic acid; 6-(2-((N-(sec-butyl)-4-(thiophen-2-yl)benzamido)methyl)phenoxy)hexanoic acid; 6-(2-((N-(sec-butyl)-4-(thiophen-3-yl)benzamido)methyl)phenoxy)hexanoic acid; 6-(2-((4-bromo-N-(sec-butyl)benzamido)methyl)phenoxy)hexanoic acid; 6-(2-((N-(3-morpholinopropyl)-4-(pyridin-3-yl)benzamido)methyl)phenoxy)hexanoic acid; 6-(2-((N-(3-morpholinopropyl)-4-(pyridin-4-yl)benzamido)methyl)phenoxy)hexanoic acid; 6-(2-((N-(3-morpholinopropyl)-[1,1'-biphenyl]-4-carboxamido)methyl)phenoxy)hexanoic acid; 6-(2-((N-(3-morpholinopropyl)-4-(1H-pyrazol-4-yl)benzamido)methyl)phenoxy)hexanoic acid; 6-(2-((4-(furan-3-yl)-N-(3-morpholinopropyl)benzamido)methyl)phenoxy)hexanoic acid; 6-(2-((N-(3-morpholinopropyl)-4-(1H-pyrazol-4-yl)benzamido)methyl)phenoxy)hexanoic acid; 6-(2-((4-(furan-2-yl)-N-(3-morpholinopropyl)benzamido)methyl)phenoxy)hexanoic acid; 6-(2-((N-(2-(pyridin-2-yl)ethyl)-[1,1'-biphenyl]-4-carboxamido)methyl)phenoxy)hexanoic acid; 6-(2-((N-(3-morpholinopropyl)-4-(thiophen-3-yl)benzamido)methyl)phenoxy)hexanoic acid; 6-(2-((N-(3-morpholinopropyl)-4-(thiophen-2-yl)benzamido)methyl)phenoxy)hexanoic acid; 6-(2-((N-(2-(pyridin-2-yl)ethyl)-4-(pyridin-3-yl)benzamido)methyl)phenoxy)hexanoic acid; 6-(2-((N-(2-(pyridin-2-yl)ethyl)-4-(pyridin-4-yl)benzamido)methyl)phenoxy)hexanoic acid; 6-(2-((4-(1H-pyrazol-4-yl)-N-(2-(pyridin-2-yl)ethyl)benzamido)methyl)phenoxy)hexanoic acid; 6-(2-((4-(furan-3-yl)-N-(2-(pyridin-2-yl)ethyl)benzamido)methyl)phenoxy)hexanoic acid; 6-(2-((N-(2-(pyridin-2-yl)ethyl)-4-(thiophen-2-yl)benzamido)methyl)phenoxy)hexanoic acid; 6-(2-((4-(furan-2-yl)-N-(2-(pyridin-2-yl)ethyl)benzamido)methyl)phenoxy)hexanoic acid; 6-(2-((N-(2-(pyridin-2-yl)ethyl)-4-(thiophen-3-yl)benzamido)methyl)phenoxy)hexanoic acid; 6-(2-((N-isopropyl-4-(pyridin-4-yl)benzamido)methyl)phenoxy)hexanoic acid; 6-(2-((N-isopropyl-4-(1H-pyrazol-4-yl)benzamido)methyl)phenoxy)hexanoic acid; 6-(2-((4-(furan-2-yl)-N-isopropylbenzamido)methyl)phenoxy)hexanoic acid; 6-(2-((N-isopropyl-4-(pyridin-3-yl)benzamido)methyl)phenoxy)hexanoic acid; 6-(2-((N-isopropyl-4-(thiophen-3-yl)benzamido)methyl)phenoxy)hexanoic acid; 6-(2-((4-(furan-3-yl)-N-isopropylbenzamido)methyl)phenoxy)hexanoic acid; 6-(2-((N-cyclopentyl-4-(pyridin-3-yl)benzamido)methyl)phenoxy)hexanoic acid; 6-(2-((N-cyclopentyl-[1,1'-biphenyl]-4-carboxamido)methyl)phenoxy)hexanoic acid; 6-(2-((N-isopropyl-4-(thiophen-2-yl)benzamido)methyl)phenoxy)hexanoic acid; 6-(2-((N-cyclopentyl-4-(1H-pyrazol-4-yl)benzamido)methyl)phenoxy)hexanoic acid; 6-(2-((N-cyclopentyl-4-(pyridin-4-yl)benzamido)methyl)phenoxy)hexanoic acid; 6-(2-((N-cyclopentyl-4-(furan-3-yl)benzamido)methyl)phenoxy)hexanoic acid; 6-(2-((N-cyclopentyl-4-(thiophen-3-yl)benzamido)methyl)phenoxy)hexanoic acid; 6-(2-((N-cyclopentyl-4-(furan-2-yl)benzamido)methyl)phenoxy)hexanoic acid; 6-(2-((N-cyclopropyl-4-(naphthalen-2-yl)benzamido)methyl)phenoxy)hexanoic acid; 6-(2-((N-cyclopropyl-4-(naphthalen-1-yl)benzamido)methyl)phenoxy)hexanoic acid; 6-(2-((N-cyclopropyl-2'-methyl-[1,1'-biphenyl]-4-carboxamido)methyl)phenoxy)hexanoic acid; 6-(2-((N-cyclopropyl-3'-methyl-[1,1'-biphenyl]-4-carboxamido)methyl)phenoxy)hexanoic acid; 6-(2-((N-cyclopropyl-2'-methoxy-[1,1'-biphenyl]-4-carboxamido)methyl)phenoxy)hexanoic acid; 6-(2-((N-cyclopropyl-4'-methoxy-[1,1'-biphenyl]-4-carboxamido)methyl)phenoxy)hexanoic acid; 6-(2-((N-cyclopropyl-3'-methoxy-[1,1'-biphenyl]-4-carboxamido)methyl)phenoxy)hexanoic acid; 6-(2-((N-cyclopropyl-4'-methyl-[1,1'-biphenyl]-4-carboxamido)methyl)phenoxy)hexanoic acid; 6-(2-((N-cyclopropyl-2'-fluoro-[1,1'-biphenyl]-4-carboxamido)methyl)phenoxy)hexanoic acid; 6-(2-((N-cyclopropyl-3'-fluoro-[1,1'-biphenyl]-4-carboxamido)methyl)phenoxy)hexanoic acid; 6-(2-((N-cyclopropyl-4'-fluoro-[1,1'-biphenyl]-4-carboxamido)methyl)phenoxy)hexanoic acid; 6-(2-((N-cyclopropyl-4'-ethyl-[1,1'-biphenyl]-4-carboxamido)methyl)phenoxy)hexanoic acid; 6-(2-((N-cyclopropyl-2',3'-dimethyl-[1,1'-biphenyl]-4-carboxamido)methyl)phenoxy)hexanoic acid; 6-(2-((N-cyclopropyl-2'-ethyl-[1,1'-biphenyl]-4-carboxamido)methyl)phenoxy)hexanoic acid; 6-(2-((N-cyclopropyl-2',5'-dimethyl-[1,1'-biphenyl]-4-carboxamido)methyl)phenoxy)hexanoic acid; 6-(2-((N-cyclopropyl-2',6'-dimethyl-[1,1'-biphenyl]-4-carboxamido)methyl)phenoxy)hexanoic acid; 6-(2-((N-cyclopropyl-3',5'-dimethyl-[1,1'-biphenyl]-4-carboxamido)methyl)phenoxy)hexanoic acid; 6-(2-((N-cyclopropyl-3'-(trifluoromethyl)-[1,1'-biphenyl]-4-carboxamido)methyl)phenoxy)hexanoic acid; 6-(2-((N-cyclopropyl-2'-(trifluoromethyl)-[1,1'-biphenyl]-4-carboxamido)methyl)phenoxy)hexanoic acid; 6-(2-((N-cyclopropyl-4'-(trifluoromethyl)-[1,1'-biphenyl]-4-carboxamido)methyl)phenoxy)hexanoic acid; 6-(2-((N-cyclopropyl-[1,1':2',1''-terphenyl]-4-carboxamido)methyl)phenoxy)hexanoic acid; 6-(2-((N-cyclopropyl-4'-propyl-[1,1'-biphenyl]-4-carboxamido)methyl)phenoxy)hexanoic acid; 6-(2-((4'-butyl-N-cyclopropyl-[1,1'-biphenyl]-4-carboxamido)methyl)phenoxy)hexanoic acid; 6-(2-((N-sec-butyl-4-(furan-2-yl)benzamido)methyl)phenoxy)hexanoic acid; 6-(2-((N-isopropylbiphenyl-4-ylcarboxamido)methyl)phenoxy)hexanoic acid; 6-(2-(2-(4-(furan-2-yl)phenyl)thiazol-5-yl)phenoxy)hexanoic acid; 6-(2-(cyclopropyl(4-(furan-2-yl)benzyl)carbamoyl)phenoxy)hexanoic acid; 6-(2-((N-cyclopropyl-2-oxoindoline-5-carboxamido)methyl)phenoxy)hexanoic acid; 6-(2-((N-cyclopropyl-2-oxo-2,3-dihydrobenzofuran-5-carboxamido)methyl)phenoxy)hexanoic acid; 6-(2-((N-cyclopropylbenzo[c][1,2,5]oxadiazole-5-carboxamido)methyl)phenoxy)hexanoic acid; 6-(2-((N-cyclopropyl-5-(furan-2-yl)thiazole-2-carboxamido)methyl)phenoxy)hexanoic acid; 6-(2-((N-cyclopropyl-[2,3'-bifuran]-5'-carboxamido)methyl)phenoxy)hexanoic acid; 6-((4-((N-cyclopropyl-4-(furan-2-yl)benzamido)methyl)thiophen-3-yl)oxy)hexanoic acid; N-(2-((5-(1H-tetrazol-5-yl)pentyl)oxy)benzyl)-N-cyclopropyl-4-(furan-2-yl)benzamide; 6-(2-((N-cyclopropyl-4-(furan-2-yl)benzamido)methyl)phenoxy)hex-3-ynoic acid; 6-(2-((N-cyclopropyl-4-(furan-2-yl)benzamido)methyl)phenoxy)hex-4-ynoic acid; (Z)-6-(2-((N-cyclopropyl-4-(furan-2-yl)benzamido)methyl)phenoxy)hex-3-enoic acid; (E)-6-(2-((N-cyclopropyl-4-(furan-2-yl)benzamido)methyl)phenoxy)hex-4-enoic acid; (E)-6-(2-((N-cyclopropyl-4-(furan-2-yl)benzamido)methyl)phenoxy)hex-2-enoic acid; (Z)-6-(2-((N-cyclopropyl-4-(furan-2-yl)benzamido)methyl)phenoxy)hex-4-enoic acid; (Z)-6-(2-((N-cyclopropyl-4-(furan-2-yl)benzamido)methyl)phenoxy)hex-2-enoic acid; (E)-6-(2-((N-cyclopropyl-4-(furan-2-yl)benzamido)methyl)phenoxy)hex-3-enoic acid; 6-(2-((N-isopropyl-[1,1'-biphenyl]-4-carboxamido)methyl)phenoxy)hexanoic acid; ethyl 6-(2-(1-(4-bromo-N-cyclopropylbenzamido)-2-(tert-butylamino)-2-oxoethyl)phenoxy)hexanoate; ethyl 6-(2-(2-(tert-butylamino)-1-(N-cyclopropyl-[1,1'-biphenyl]-4-carboxamido)-2-oxoethyl)phenoxy)hexanoate; ethyl 6-(2-(2-amino-1-(N-cyclopropyl-[1,1'-biphenyl]-4-carboxamido)-2-oxoethyl)phenoxy)hexanoate; 6-(2-(2-amino-1-(N-cyclopropyl-[1,1'-biphenyl]-4-carboxamido)-2- oxoethyl)phenoxy)hexanoic acid; 6-(2-(2-(tert-butylamino)-1-(N-cyclopropyl-[1,1'-biphenyl]-4-carboxamido)-2-oxoethyl)phenoxy)hexanoic acid; 6-(2-((N-cyclopropyl-[1,1'-biphenyl]-4-carboxamido)methyl)phenoxy)hexanoic acid; N-(2-amino-1-(2-((6-(hydroxyamino)-6-oxohexyl)oxy)phenyl)-2-oxoethyl)-N-cyclopropyl-[1,1'-biphenyl]-4-carboxamide; 6-(2-((N-cyclopropyl-4-(pyridin-4-yl)benzamido)methyl)phenoxy)hexanoic acid; 6-(2-((N-cyclopropyl-4-(pyridin-3-yl)benzamido)methyl)phenoxy)hexanoic acid; 6-(2-((N-cyclopropyl-4-(1H-pyrazol-4-yl)benzamido)methyl)phenoxy)hexanoic acid; 6-(2-((N-cyclopropyl-4-(furan-2-yl)benzamido)methyl)phenoxy)hexanoic acid; 6-(2-((N-cyclopropyl-4-(furan-3-yl)benzamido)methyl)phenoxy)hexanoic acid; 6-(2-((N-cyclopropyl-4-(thiophen-2-yl)benzamido)methyl)phenoxy)hexanoic acid; 6-(2-((N-cyclopropyl-4-(thiophen-3-yl)benzamido)methyl)phenoxy)hexanoic acid; 6-(2-((N-benzyl-[1,1'-biphenyl]-4-carboxamido)methyl)phenoxy)hexanoic acid; 6-(2-((N-benzyl-4-(pyridin-3-yl)benzamido)methyl)phenoxy)hexanoic acid; 6-(2-((N-benzyl-4-(pyridin-4-yl)benzamido)methyl)phenoxy)hexanoic acid; 6-(2-((N-benzyl-4-(1H-pyrazol-4-yl)benzamido)methyl)phenoxy)hexanoic acid; 6-(2-((N-benzyl-4-(thiophen-2-yl)benzamido)methyl)phenoxy)hexanoic acid; 6-(2-((N-benzyl-4-(furan-3-yl)benzamido)methyl)phenoxy)hexanoic acid; 6-(2-((N-benzyl-4-(furan-2-yl)benzamido)methyl)phenoxy)hexanoic acid; 6-(2-((N-benzyl-4-(thiophen-3-yl)benzamido)methyl)phenoxy)hexanoic acid; N-benzyl-N-(2-((6-(hydroxyamino)-6-oxohexyl)oxy)benzyl)-4-(pyridin-4-yl)benzamide; N-benzyl-N-(2-((6-(hydroxyamino)-6-oxohexyl)oxy)benzyl)-[1,1'-biphenyl]-4-carboxamide; N-benzyl-N-(2-((6-(hydroxyamino)-6-oxohexyl)oxy)benzyl)-4-(pyridin-3-yl)benzamide; N-benzyl-N-(2-((6-(hydroxyamino)-6-oxohexyl)oxy)benzyl)-4-(1H-pyrazol-4-yl)benzamide; N-benzyl-N-(2-((6-(hydroxyamino)-6-oxohexyl)oxy)benzyl)-4-(thiophen-2-yl)benzamide; N-benzyl-4-(furan-2-yl)-N-(2-((6-(hydroxyamino)-6-oxohexyl)oxy)benzyl)benzamide; N-benzyl-4-(furan-3-yl)-N-(2-((6-(hydroxyamino)-6-oxohexyl)oxy)benzyl)benzamide; 6-(2-((N-(sec-butyl)-[1,1'-biphenyl]-4-carboxamido)methyl)phenoxy)hexanoic acid; N-benzyl-N-(2-((6-(hydroxyamino)-6-oxohexyl)oxy)benzyl)-4-(thiophen-3-yl)benzamide; 6-(2-((N-(sec-butyl)-4-(pyridin-3-yl)benzamido)methyl)phenoxy)hexanoic acid; 6-(2-((N-(sec-butyl)-4-(pyridin-4-yl)benzamido)methyl)phenoxy)hexanoic acid; 6-(2-((N-(sec-butyl)-4-(1H-pyrazol-4-yl)benzamido)methyl)phenoxy)hexanoic acid; 6-(2-((N-(sec-butyl)-4-(furan-2-yl)benzamido)methyl)phenoxy)hexanoic acid; 6-(2-((N-(sec-butyl)-4-(furan-3-yl)benzamido)methyl)phenoxy)hexanoic acid; 6-(2-((N-(sec-butyl)-4-(thiophen-2-yl)benzamido)methyl)phenoxy)hexanoic acid; 6-(2-((N-(sec-butyl)-4-(thiophen-3-yl)benzamido)methyl)phenoxy)hexanoic acid; 6-(2-((4-bromo-N-(sec-butyl)benzamido)methyl)phenoxy)hexanoic acid; 6-(2-((N-(3-morpholinopropyl)-4-(pyridin-3-yl)benzamido)methyl)phenoxy)hexanoic acid; 6-(2-((N-(3-morpholinopropyl)-4-(pyridin-4-yl)benzamido)methyl)phenoxy)hexanoic acid; 6-(2-((N-(3-morpholinopropyl)-[1,1'-biphenyl]-4-carboxamido)methyl)phenoxy)hexanoic acid; 6-(2-((N-(3-morpholinopropyl)-4-(1H-pyrazol-4-yl)benzamido)methyl)phenoxy)hexanoic acid; 6-(2-((4-(furan-3-yl)-N-(3-morpholinopropyl)benzamido)methyl)phenoxy)hexanoic acid; 6-(2-((N-(3-morpholinopropyl)-4-(1H-pyrazol-4-yl)benzamido)methyl)phenoxy)hexanoic acid; 6-(2-((4-(furan-2-yl)-N-(3-morpholinopropyl)benzamido)methyl)phenoxy)hexanoic acid; 6-(2-((N-(2-(pyridin-2-yl)ethyl)-[1,1'-biphenyl]-4-carboxamido)methyl)phenoxy)hexanoic acid; 6-(2-((N-(3-morpholinopropyl)-4-(thiophen-3-yl)benzamido)methyl)phenoxy)hexanoic acid; 6-(2-((N-(3-morpholinopropyl)-4-(thiophen-2-yl)benzamido)methyl)phenoxy)hexanoic acid; 6-(2-((N-(2-(pyridin-2-yl)ethyl)-4-(pyridin-3-yl)benzamido)methyl)phenoxy)hexanoic acid; 6-(2-((N-(2-(pyridin-2-yl)ethyl)-4-(pyridin-4-yl)benzamido)methyl)phenoxy)hexanoic acid; 6-(2-((4-(1H-pyrazol-4-yl)-N-(2-(pyridin-2-yl)ethyl)benzamido)methyl)phenoxy)hexanoic acid; 6-(2-((4-(furan-3-yl)-N-(2-(pyridin-2-yl)ethyl)benzamido)methyl)phenoxy)hexanoic acid; 6-(2-((N-(2-(pyridin-2-yl)ethyl)-4-(thiophen-2-yl)benzamido)methyl)phenoxy)hexanoic acid; 6-(2-((4-(furan-2-yl)-N-(2-(pyridin-2-yl)ethyl)benzamido)methyl)phenoxy)hexanoic acid; 6-(2-((N-(2-(pyridin-2-yl)ethyl)-4-(thiophen-3-yl)benzamido)methyl)phenoxy)hexanoic acid; 6-(2-((N-isopropyl-[1,1'-biphenyl]-4-carboxamido)methyl)phenoxy)hexanoic acid; 6-(2-((N-isopropyl-4-(pyridin-4-yl)benzamido)methyl)phenoxy)hexanoic acid; 6-(2-((N-isopropyl-4-(1H-pyrazol-4-yl)benzamido)methyl)phenoxy)hexanoic acid; 6-(2-((4-(furan-2-yl)-N-isopropylbenzamido)methyl)phenoxy)hexanoic acid; 6-(2-((N-isopropyl-4-(pyridin-3-yl)benzamido)methyl)phenoxy)hexanoic acid; 6-(2-((N-isopropyl-4-(thiophen-3-yl)benzamido)methyl)phenoxy)hexanoic acid; 6-(2-((4-(furan-3-yl)-N-isopropylbenzamido)methyl)phenoxy)hexanoic acid; 6-(2-((N-cyclopentyl-4-(pyridin-3-yl)benzamido)methyl)phenoxy)hexanoic acid; 6-(2-((N-cyclopentyl-[1,1'-biphenyl]-4-carboxamido)methyl)phenoxy)hexanoic acid; 6-(2-((N-isopropyl-4-(thiophen-2-yl)benzamido)methyl)phenoxy)hexanoic acid; 6-(2-((N-cyclopentyl-4-(1H-pyrazol-4-yl)benzamido)methyl)phenoxy)hexanoic acid; 6-(2-((N-cyclopentyl-4-(pyridin-4-yl)benzamido)methyl)phenoxy)hexanoic acid; 6-(2-((N-cyclopentyl-4-(furan-3-yl)benzamido)methyl)phenoxy)hexanoic acid; 6-(2-((N-cyclopentyl-4-(thiophen-3-yl)benzamido)methyl)phenoxy)hexanoic acid; 6-(2-((N-cyclopentyl-4-(furan-2-yl)benzamido)methyl)phenoxy)hexanoic acid; 6-(2-((N-cyclopropyl-4-(naphthalen-2-yl)benzamido)methyl)phenoxy)hexanoic acid; 6-(2-((N-cyclopropyl-4-(naphthalen-1-yl)benzamido)methyl)phenoxy)hexanoic acid; 6-(2-((N-cyclopropyl-2'-methyl-[1,1'-biphenyl]-4-carboxamido)methyl)phenoxy)hexanoic acid; 6-(2-((N-cyclopropyl-3'-methyl-[1,1'-biphenyl]-4-carboxamido)methyl)phenoxy)hexanoic acid; 6-(2-((N-cyclopropyl-2'-methoxy-[1,1'-biphenyl]-4-carboxamido)methyl)phenoxy)hexanoic acid; 6-(2-((N-cyclopropyl-4'-methoxy-[1,1'-biphenyl]-4-carboxamido)methyl)phenoxy)hexanoic acid; 6-(2-((N-cyclopropyl-3'-methoxy-[1,1'-biphenyl]-4-carboxamido)methyl)phenoxy)hexanoic acid; 6-(2-((N-cyclopropyl-4'-methyl-[1,1'-biphenyl]-4-carboxamido)methyl)phenoxy)hexanoic acid; 6-(2-((N-cyclopropyl-2'-fluoro-[1,1'-biphenyl]-4-carboxamido)methyl)phenoxy)hexanoic acid; 6-(2-((N-cyclopropyl-3'-fluoro-[1,1'-biphenyl]-4-carboxamido)methyl)phenoxy)hexanoic acid; 6-(2-((N-cyclopropyl-4'-fluoro-[1,1'-biphenyl]-4-carboxamido)methyl)phenoxy)hexanoic acid; 6-(2-((N-cyclopropyl-4'-ethyl-[1,1'-biphenyl]-4-carboxamido)methyl)phenoxy)hexanoic acid; 6-(2-((N-cyclopropyl-2',3'-dimethyl-[1,1'-biphenyl]-4-carboxamido)methyl)phenoxy)hexanoic acid; 6-(2-((N-cyclopropyl-2'-ethyl-[1,1'-biphenyl]-4-carboxamido)methyl)phenoxy)hexanoic acid; 6-(2-((N-cyclopropyl-2',5'-dimethyl-[1,1'-biphenyl]-4-carboxamido)methyl)phenoxy)hexanoic acid; 6-(2-((N-cyclopropyl-2',6'-dimethyl-[1,1'-biphenyl]-4-carboxamido)methyl)phenoxy)hexanoic acid; 6-(2-((N-cyclopropyl-3',5'-dimethyl-[1,1'-biphenyl]-4-carboxamido)methyl)phenoxy)hexanoic acid; 6-(2-((N-cyclopropyl-3'-(trifluoromethyl)-[1,1'-biphenyl]-4-carboxamido)methyl)

phenoxy)hexanoic acid; 6-(2-((N-cyclopropyl-2'-(trifluoromethyl)-[1,1'-biphenyl]-4-carboxamido)methyl)phenoxy)hexanoic acid; 6-(2-((N-cyclopropyl-4'-(trifluoromethyl)-[1,1'-biphenyl]-4-carboxamido)methyl)phenoxy)hexanoic acid; 6-(2-((N-cyclopropyl-[1,1':2',1''-terphenyl]-4-carboxamido)methyl)phenoxy)hexanoic acid; 6-(2-((N-cyclopropyl-4'-propyl-[1,1'-biphenyl]-4-carboxamido)methyl)phenoxy)hexanoic acid; 6-(2-((4'-butyl-N-cyclopropyl-[1,1'-biphenyl]-4-carboxamido)methyl)phenoxy)hexanoic acid; 6-(2-((N-sec-butyl-4-(furan-2-yl)benzamido)methyl)phenoxy)hexanoic acid; 6-(2-((N-isopropylbiphenyl-4-ylcarboxamido)methyl)phenoxy)hexanoic acid; 6-(2-(2-(4-(furan-2-yl)phenyl)thiazol-5-yl)phenoxy)hexanoic acid; 6-(2-(cyclopropyl(4-(furan-2-yl)benzyl)carbamoyl)phenoxy)hexanoic acid; 6-(2-((N-cyclopropyl-2-oxoindoline-5-carboxamido)methyl)phenoxy)hexanoic acid; 6-(2-((N-cyclopropylbenzo[c][1,2,5]oxadiazole-5-carboxamido)methyl)phenoxy)hexanoic acid; 6-((4-((N-cyclopropyl-4-(furan-2-yl)benzamido)methyl)thiophen-3-yl)oxy)hexanoic acid; N-(2-((5-(1H-tetrazol-5-yl)pentyl)oxy)benzyl)-N-cyclopropyl-4-(furan-2-yl)benzamide; 6-(2-((N-cyclopropyl-4-(furan-2-yl)benzamido)methyl)phenoxy)hex-3-ynoic acid; 6-(2-((N-cyclopropyl-4-(furan-2-yl)benzamido)methyl)phenoxy)hex-4-ynoic acid; (Z)-6-(2-((N-cyclopropyl-4-(furan-2-yl)benzamido)methyl)phenoxy)hex-3-enoic acid; (E)-6-(2-((N-cyclopropyl-4-(furan-2-yl)benzamido)methyl)phenoxy)hex-4-enoic acid; (E)-6-(2-((N-cyclopropyl-4-(furan-2-yl)benzamido)methyl)phenoxy)hex-2-enoic acid; (Z)-6-(2-((N-cyclopropyl-4-(furan-2-yl)benzamido)methyl)phenoxy)hex-4-enoic acid; (Z)-6-(2-((N-cyclopropyl-4-(furan-2-yl)benzamido)methyl)phenoxy)hex-2-enoic acid; (E)-6-(2-((N-cyclopropyl-4-(furan-2-yl)benzamido)methyl)phenoxy)hex-3-enoic acid; N-cyclopropyl-N-(2-((5-(2,4-dioxothiazolidin-5-yl)pentyl)oxy)benzyl)-4-(furan-2-yl)benzamide; N-cyclopropyl-N-(2-((5-(2,4-dioxooxazolidin-5-yl)pentyl)oxy)benzyl)-4-(furan-2-yl)benzamide; N-cyclopropyl-4-(furan-2-yl)-N-(2-((5-(3-hydroxy-1-methyl-1H-pyrazol-5-yl)pentyl)oxy)benzyl)benzamide; N-cyclopropyl-4-(furan-2-yl)-N-(2-((5-(3-hydroxyisothiazol-5-yl)pentyl)oxy)benzyl)benzamide; N-cyclopropyl-4-(furan-2-yl)-N-(2-((5-(3-hydroxyisoxazol-5-yl)pentyl)oxy)benzyl)benzamide; N-cyclopropyl-N-(2-((5-(2,5-dioxo-2,5-dihydro-1H-imidazol-4-yl)pentyl)oxy)benzyl)-4-(furan-2-yl)benzamide; N-cyclopropyl-N-(2-((5-(2,5-dioxo-2,5-dihydro-1H-pyrrol-3-yl)pentyl)oxy)benzyl)-4-(furan-2-yl)benzamide; N-cyclopropyl-4-(furan-2-yl)-N-(2-((5-(6-hydroxy-4-oxo-4H-1,3-dioxin-2-yl)pentyl)oxy)benzyl)benzamide; 6-(2-((4-cyclopropoxy-N-isopropylbenzamido)methyl)phenoxy)hexanoic acid; 6-(2-((N-isopropyl-4-methylbenzamido)methyl)phenoxy)hexanoic acid; 6-(2-((4-(cyclopentylethynyl)-N-isopropylbenzamido)methyl)phenoxy)hexanoic acid; 6-(2-((N-isopropyl-4-((1-methylazetidin-3-yl)ethynyl)benzamido)methyl)phenoxy)hexanoic acid; 6-(2-((4-chloro-N-isopropylbenzamido)methyl)phenoxy)hexanoic acid; 6-(2-((N-isopropyl-4-methoxybenzamido)methyl)phenoxy)hexanoic acid; 6-(2-((4-(dimethylamino)-N-isopropylbenzamido)methyl)phenoxy)hexanoic acid; 6-(2-((N-isopropyl-4-(trifluoromethoxy)benzamido)methyl)phenoxy)hexanoic acid; 6-(2-((4-acetyl-N-isopropylbenzamido)methyl)phenoxy)hexanoic acid; 6-(2-((N-isopropyl-4-(methylsulfonyl)benzamido)methyl)phenoxy)hexanoic acid; 6-(2-((3'-(furan-3-yl)-N-isopropyl-[1,1'-biphenyl]-4-carboxamido)methyl)phenoxy)hexanoic acid; 6-(2-((4-fluoro-N-isopropylbenzamido)methyl)phenoxy)hexanoic acid; 6-(2-((N-isopropyl-4-(4-methoxytetrahydro-2H-pyran-4-yl)benzamido)methyl)phenoxy)hexanoic acid; 6-(2-((N-isopropyl-4-(3,3,3-trifluoroprop-1-yn-1-yl)benzamido)methyl)phenoxy)hexanoic acid; 6-(2-((N-isopropyl-4-(oxetan-3-ylethynyl)benzamido)methyl)phenoxy)hexanoic acid; 6-(2-((4-(cyclobutylethynyl)-N-isopropylbenzamido)methyl)phenoxy)hexanoic acid; 6-(2-((N-isopropyl-4-(1-(trifluoromethyl)cyclopropyl)benzamido)methyl)phenoxy)hexanoic acid; 6-(2-((N-isopropyl-4-(1-methoxycyclopropyl)benzamido)methyl)phenoxy)hexanoic acid; 6-(2-((N-isopropyl-4-(tetrahydro-2H-pyran-2-yl)benzamido)methyl)phenoxy)hexanoic acid; 6-(2-((N-isopropyl-4-(4-methylbicyclo[2.2.2]octan-1-yl)benzamido)methyl)phenoxy)hexanoic acid; 6-(2-((N-isopropyl-4-(6-oxo-1,6-dihydropyridin-2-yl)benzamido)methyl)phenoxy)hexanoic acid; 6-(2-((N-isopropyl-4-(oxetan-2-ylethynyl)benzamido)methyl)phenoxy)hexanoic acid; 6-(2-((N-isopropyl-4-(4-(trifluoromethyl)bicyclo[2.2.2]octan-1-yl)benzamido)methyl)phenoxy)hexanoic acid; 6-(2-((N-isopropyl-4-(4-phenylbicyclo[2.2.2]octan-1-yl)benzamido)methyl)phenoxy)hexanoic acid; 6-(2-((4-cyano-N-isopropylbenzamido)methyl)phenoxy)hexanoic acid; 6-(2-((N-isopropyl-4-(oxetan-2-yl)benzamido)methyl)phenoxy)hexanoic acid; 6-(2-((N-isopropyl-4-(pyrrolidin-1-yl)benzamido)methyl)phenoxy)hexanoic acid; 6-(2-((5-(furan-2-yl)-N-isopropylpicolinamido)methyl)phenoxy)hexanoic acid; 6-(2-((2-(furan-2-yl)-N-isopropylthiazole-5-carboxamido)methyl)phenoxy)hexanoic acid; 6-(2-((4-(furan-2-yl)-N-isopropyl-2,5-dioxopiperazine-1-carboxamido)methyl)phenoxy)hexanoic acid; 6-(2-(((4-(furan-2-yl)-N-isopropylphenyl)sulfonamido)methyl)phenoxy)hexanoic acid; 6-(2-(2-((4-(furan-2-yl)phenyl)(isopropyl)amino)-2-oxoethyl)phenoxy)hexanoic acid; 6-(2-((6-(furan-2-yl)-N-isopropylnicotinamido)methyl)phenoxy)hexanoic acid; 6-(2-((4-(furan-2-yl)benzyl)(isopropyl)carbamoyl)phenoxy)hexanoic acid; 6-(2-((2-(furan-2-yl)-N-isopropyloxazole-5-carboxamido)methyl)phenoxy)hexanoic acid; 6-(2-(3-((4-(furan-2-yl)phenyl)(isopropyl)amino)-3-oxopropyl)phenoxy)hexanoic acid; 6-(2-((2-fluoro-4-(furan-2-yl)-N-isopropylbenzamido)methyl)phenoxy)hexanoic acid; 6-(2-((3-fluoro-4-(furan-2-yl)-N-isopropylbenzamido)methyl)phenoxy)hexanoic acid; 6-(2-((1-(furan-2-yl)-N-isopropylpiperidine-4-carboxamido)methyl)phenoxy)hexanoic acid; 6-(2-((5-(furan-2-yl)-N-isopropylisoxazole-3-carboxamido)methyl)phenoxy)hexanoic acid; 6-(2-((4-(furan-2-yl)-N-isopropylcyclohexane-1-carboxamido)methyl)phenoxy)hexanoic acid; 6-(2-(((6-(furan-2-yl)-1H-indazol-3-yl)(isopropyl)amino)methyl)phenoxy)hexanoic acid; 6-(2-((5-(furan-2-yl)-N-isopropylthiazole-2-carboxamido)methyl)phenoxy)hexanoic acid; 6-(2-((N-isopropyl-2-methylbenzofuran-6-carboxamido)methyl)phenoxy)hexanoic acid; 6-(2-((N-isopropyl-2-methylbenzofuran-5-carboxamido)methyl)phenoxy)hexanoic acid; 6-(2-((7-(furan-2-yl)-4-oxoquinazolin-3(4H)-yl)methyl)phenoxy)hexanoic acid; 6-(2-((1-(furan-2-yl)-N-isopropyl-2-oxopiperidine-4-carboxamido)methyl)phenoxy)hexanoic acid; 6-(2-((5-(furan-2-yl)-N-isopropyl-1H-pyrazole-3-carboxamido)methyl)phenoxy)hexanoic acid; 6-(2-((5-(furan-2-yl)-N-isopropyl-1-methyl-1H-pyrazole-3-carboxamido)methyl)phenoxy)hexanoic acid; 6-(2-((5-(furan-2-yl)-N-isopropyl-3,6-dioxopiperazine-2-carboxamido)methyl)phenoxy)hexanoic acid; 6-(2-((4-(furan-2-yl)-N-isopropylpiperidine-1-carboxamido)methyl)phenoxy)hexanoic acid; 6-(2-((4-(furan-2-yl)-N-methylbenzamido)methyl)phenoxy)hexanoic acid; 6-(2-((4-(furan-2-yl)-N-(2,2,2-trifluoroethyl)benzamido)methyl)phenoxy)hexanoic acid; 6-(2-((4-(furan-2-yl)-N-(2-methoxyethyl)benzamido)methyl)phenoxy)hexanoic acid; 6-(2-((4-(furan-2-yl)benzamido)methyl)phenoxy)hexanoic acid; 6-(2-((4-(furan-2- yl)-N-(oxetan-3-yl)benzamido)methyl)phenoxy)hexanoic acid; 6-(2-((2-(4-(furan-2-yl)phenyl)-5-methyl-1H-imidazol-1-yl)methyl)phenoxy)hexanoic acid; 6-(2-((N-(2-cyanopropan-2-yl)-4-(furan-2-yl)benzamido)methyl)phenoxy)hexanoic acid; 6-(2-((2-(4-(furan-2-yl)phenyl)-4-methyl-1H-imidazol-1-yl)methyl)phenoxy)hexanoic acid; 6-(2-(2-(4-(furan-2-yl)phenyl)-1-methyl-1H-imidazol-5-yl)phenoxy)hexanoic acid; 6-(2-((6-(furan-2-yl)-3-methyl-1-oxo-3,4-dihydroisoquinolin-2(1H)-yl)methyl)phenoxy)hexanoic acid; 6-(2-((4-(furan-2-yl)-N-hydroxybenzamido)methyl)phenoxy)hexanoic acid; 6-(2-((3-(4-(furan-2-yl)phenyl)-5-methylisoxazol-4-yl)methyl)phenoxy)hexanoic acid; 6-(2-((4-(furan-2-yl)-N-methoxybenzamido)methyl)phenoxy)hexanoic acid; 6-(2-((N-(cyclopropylmethyl)-4-(furan-2-yl)benzamido)methyl)phenoxy)hexanoic acid; 6-(2-((N-(1-cyclopropylethyl)-4-(furan-2-yl)benzamido)methyl)phenoxy)hexanoic acid; 6-(2-(1-(4-(furan-2-yl)benzoyl)pyrrolidin-2-yl)phenoxy)hexanoic acid; 6-(2-(1-(4-(furan-2-yl)benzoyl)azetidin-2-yl)phenoxy)hexanoic acid; 6-(2-(1-(4-(furan-2-yl)benzoyl)piperidin-2-yl)phenoxy)hexanoic acid; 6-(4-bromo-2-((4-(furan-2-yl)-N-isopropylbenzamido)methyl)phenoxy)hexanoic acid; 6-(2-((4-(furan-2-yl)-N-isopropylbenzamido)methyl)-4-methylphenoxy)hexanoic acid; 6-(4-fluoro-2-((4-(furan-2-yl)-N-isopropylbenzamido)methyl)phenoxy)hexanoic acid; 6-(4-cyano-2-((4-(furan-2-yl)-N-isopropylbenzamido)methyl)phenoxy)hexanoic acid; 6-(2-((4-(furan-2-yl)-N-isopropylbenzamido)methyl)-4-methoxyphenoxy)hexanoic acid; 6-((3-((4-(furan-2-yl)-N-isopropylbenzamido)methyl)pyridin-2-yl)oxy)hexanoic acid; 6-((2-((4-(furan-2-yl)-N-isopropylbenzamido)methyl)pyridin-3-yl)oxy)hexanoic acid; 6-((3-((4-(furan-2-yl)-N-isopropylbenzamido)methyl)pyridin-4-yl)oxy)hexanoic acid; 6-((4-((4-(furan-2-yl)-N-isopropylbenzamido)methyl)-1-methyl-1H-pyrazol-3-yl)oxy)hexanoic acid; 6-((4-((4-(furan-2-yl)-N-isopropylbenzamido)methyl)pyridin-3-yl)oxy)hexanoic acid; 6-((2-(4-(furan-2-yl)benzoyl)-1,2,3,4-tetrahydroisoquinolin-8-yl)oxy)hexanoic acid; 6-((4-((4-(furan-2-yl)-N-isopropylbenzamido)methyl)isothiazol-3-yl)oxy)hexanoic acid; 6-((2-((4-(furan-2-yl)-N-isopropylbenzamido)methyl)cyclopentyl)oxy)hexanoic acid; 6-(4-cyclopropyl-2-((4-(furan-2-yl)-N-isopropylbenzamido)methyl)phenoxy)hexanoic acid; 6-((2-((4-(furan-2-yl)-N-isopropylbenzamido)methyl)cyclohexyl)oxy)hexanoic acid; 6-(4-(azetidin-1-yl)-2-((4-(furan-2-yl)-N-isopropylbenzamido)methyl)phenoxy)hexanoic acid; 6-(2-((4-(furan-2-yl)-N-isopropylbenzamido)methyl)-4-(trifluoromethyl)phenoxy)hexanoic acid; N-(2-(4-(2H-tetrazol-5-yl)butoxy)benzyl)-4-(furan-2-yl)-N-isopropylbenzamide; 7-(2-((4-(furan-2-yl)-N-isopropylbenzamido)methyl)phenoxy)heptanoic acid; 2-(3-(2-((4-(furan-2-yl)-N-isopropylbenzamido)methyl)phenoxy)propoxy)acetic acid; 5-(2-(2-((4-(furan-2-yl)-N-isopropylbenzamido)methyl)phenoxy)ethyl)isoxazole-3-carboxylic acid; 2-(5-((2-((4-(furan-2-yl)-N-isopropylbenzamido)methyl)phenoxy)methyl)isoxazol-3-yl)acetic acid; 2-(4-(2-((4-(furan-2-yl)-N-isopropylbenzamido)methyl)phenoxy)cyclohexyl)acetic acid; 5-(2-((4-(furan-2-yl)-N-isopropylbenzamido)methyl)phenoxy)pentanoic acid; 3-(2-(2-((4-(furan-2-yl)-N-isopropylbenzamido)methyl)phenoxy)ethoxy)propanoic acid; 3-(2-(2-((4-(furan-2-yl)-N-isopropylbenzamido)methyl)phenoxy)acetamido)propanoic acid; 3-(4-((2-((4-(furan-2-yl)-N-isopropylbenzamido)methyl)phenoxy)methyl)thiazol-2-yl)propanoic acid; 3-(2-(2-((4-(furan-2-yl)-N-isopropylbenzamido)methyl)phenoxy)ethyl)cyclobutane-1-carboxylic acid; 3-((2-(2-((4-(furan-2-yl)-N-isopropylbenzamido)methyl)phenoxy)ethyl)amino)-3-oxopropanoic acid; 3-(3-(2-((4-(furan-2-yl)-N-isopropylbenzamido)methyl)phenoxy)azetidin-1-yl)propanoic acid; 6-(2-((4-(furan-2-yl)-N-isopropylbenzamido)methyl)phenoxy)heptanoic acid; 2-(3-((2-((4-(furan-2-yl)-N-isopropylbenzamido)methyl)phenoxy)methyl)azetidin-1-yl)acetic acid; 2-(4-((2-((4-(furan-2-yl)-N-isopropylbenzamido)methyl)phenoxy)methyl)thiazol-2-yl)acetic acid; 2-((3-(2-((4-(furan-2-yl)-N-isopropylbenzamido)methyl)phenoxy)propyl)thio)acetic acid; 2-((3-(2-((4-(furan-2-yl)-N-isopropylbenzamido)methyl)phenoxy)cyclopentyl)oxy)acetic acid; 1-(2-(2-((4-(furan-2-yl)-N-isopropylbenzamido)methyl)phenoxy)acetyl)pyrrolidine-3-carboxylic acid; 1-(2-(2-((4-(furan-2-yl)-N-isopropylbenzamido)methyl)phenoxy)ethyl)pyrrolidine-3-carboxylic acid; (E)-6-(2-((4-(furan-2-yl)-N-isopropylbenzamido)methyl)phenoxy)-4-methylhex-4-enoic acid; (S)-4-((2-((4-(furan-2-yl)-N-isopropylbenzamido)methyl)phenyl)sulfonyl)-2,3-dihydro-1H-indene-2-carboxylic acid; 4-(furan-2-yl)-N-(2-(4-(5-hydroxy-1,3,4-oxadiazol-2-yl)butoxy)benzyl)-N-isopropylbenzamide; 1-(2-(2-((4-(furan-2-yl)-N-isopropylbenzamido)methyl)phenoxy)ethyl)azetidine-3-carboxylic acid; 2-(4-((2-((4-(furan-2-yl)-N-isopropylbenzamido)methyl)phenoxy)methyl)-1H-1,2,3-triazol-1-yl)acetic acid; 3-(2-((4-(furan-2-yl)-N-isopropylbenzamido)methyl)phenoxy)piperidin-1-yl)propanoic acid; 6-(2-((4-(cyclopropylethynyl)-N-isopropylbenzamido)methyl)phenoxy)hexanoic acid; 6-(2-(1-(4-(furan-2-yl)benzyl)-5-methyl-1H-imidazol-2-yl)phenoxy)hexanoic acid; 6-(2-((4-(4-(furan-2-yl)phenyl)-5-methylisoxazol-3-yl)methyl)phenoxy)hexanoic acid; 6-(2-((N-benzyl-4-(furan-2-yl)benzamido)methyl)phenoxy)hexanoic acid; 6-(2-((4-(cyclopropylethynyl)-N-methylbenzamido)methyl)phenoxy)hexanoic acid; 6-(2-((N-methyl-4-(3,3,3-trifluoroprop-1-yn-1-yl)benzamido)methyl)phenoxy)hexanoic acid; 6-(2-((4-cyclopropoxy-N-methylbenzamido)methyl)phenoxy)hexanoic acid; 6-(2-((5-(furan-2-yl)-N-methylpicolinamido)methyl)phenoxy)hexanoic acid; 6-(2-((5-(furan-2-yl)-N-methylthiazole-2-carboxamido)methyl)phenoxy)hexanoic acid; 3-(2-(2-((4-(furan-2-yl)-N-methylbenzamido)methyl)phenoxy)ethoxy)propanoic acid; N-(2-(4-(2H-tetrazol-5-yl)butoxy)benzyl)-4-(furan-2-yl)-N-methylbenzamide; 6-(2-((4-(furan-2-yl)-N-methylbenzamido)methyl)phenoxy)heptanoic acid; 6-((3-((4-(furan-2-yl)-N-methylbenzamido)methyl)pyridin-2-yl)oxy)hexanoic acid; 6-((3-((6-(furan-2-yl)-N-methylnicotinamido)methyl)pyridin-2-yl)oxy)hexanoic acid; 6-(4-fluoro-2-((4-(furan-2-yl)-N-methylbenzamido)methyl)phenoxy)hexanoic acid; 6-(2-((4-(furan-2-yl)-N-methylbenzamido)methyl)-4-methoxyphenoxy)hexanoic acid; 6-(2-((4-(furan-2-yl)-N-methylbenzamido)methyl)-4-methylphenoxy)hexanoic acid; 6-(2-((6-(cyclopropylethynyl)-N-isopropylnicotinamido)methyl)phenoxy)hexanoic acid; 6-(2-((6-(cyclopropylethynyl)-N-methylnicotinamido)methyl)phenoxy)hexanoic acid; 6-(2-((N-(but-2-yn-1-yl)-6-(furan-2-yl)nicotinamido)methyl)phenoxy)hexanoic acid; 6-(2-((6-fluoro-N-isopropylnicotinamido)methyl)phenoxy)hexanoic acid; 6-(2-((6-fluoro-N-(furan-2-ylmethyl)nicotinamido)methyl)phenoxy)hexanoic acid; 6-(2-((N-benzyl-6-fluoronicotinamido)methyl)phenoxy)hexanoic acid; 6-(2-(2-(4-(furan-2-yl)phenyl)pyrrolidine-1-carbonyl)phenoxy)hexanoic acid; 6-(2-((N-isopropyl-[1,1'-biphenyl]-4-carboxamido)methyl)phenoxy)hexanoic acid; 6-(2-((N-(sec-butyl)-4-(furan-2-yl)benzamido)methyl)phenoxy)hexanoic acid; 6-(2-((N-isopropyl-4-(thiophen-2-yl)benzamido)methyl)phenoxy)hexanoic acid; sodium 6-(2-((N-cyclopropyl-4-(furan-2-yl)benzamido)methyl)phenoxy)

hexanoate; 2-(2-methyl-4-(((4-methyl-2-(4-(trifluoromethyl)phenyl)thiazol-5-yl)methyl)thio)phenoxy) acetic acid; (E)-6-(2-((4-(furan-2-yl)-N'-hydroxy-N-isopropylbenzimidamido)methyl)phenoxy)hexanoic acid; 6-(2-((4-((fluoromethyl)thio)-N-isopropylbenzamido) methyl)phenoxy)hexanoic acid; 6-(2-((4-((difluoromethyl) thio)-N-isopropylbenzamido)methyl)phenoxy)hexanoic acid; 6-(2-((4-fluoro-5-(furan-2-yl)-N-isopropyl-1H-pyrazole-3-carboxamido)methyl)phenoxy)hexanoic acid; 6-(2-((5-(cyclopropylethynyl)-N-isopropyl-1H-pyrazole-3-carboxamido)methyl)phenoxy)hexanoic acid; (R)-6-(2-((5-(furan-2-yl)-N-isopropyl-1H-pyrazole-3-carboxamido) methyl)phenoxy)heptanoic acid; 6-(2-((3-(4-(furan-2-yl) phenyl)-5-methyl-4H-1,2,4-triazol-4-yl)methyl)phenoxy) hexanoic acid; 6-(2-((5-(4-(furan-2-yl)phenyl)-3-methyl-1H-1,2,4-triazol-1-yl)methyl)phenoxy)hexanoic acid; 6-(2-((2-(5-(furan-2-yl)pyridin-2-yl)-4-methyl-1H-imidazol-1-yl)methyl)phenoxy)hexanoic acid; 6-(2-((2-(5-(furan-2-yl) pyridin-2-yl)-5-methyl-1H-imidazol-1-yl)methyl)phenoxy) hexanoic acid; 6-(2-((2-(4-(furan-2-yl)phenyl)-5-methyl-1H-imidazol-1-yl)methyl)phenoxy)hexanoic acid; 6-(2-((2-(4-(furan-2-yl)phenyl)-4-methyl-1H-imidazol-1-yl)methyl) phenoxy)hexanoic acid; 6-(2-(5-(4-(furan-2-yl)phenyl)-1-methyl-1H-imidazol-2-yl)phenoxy)hexanoic acid; 6-(2-((4-(furan-2-yl)benzyl)(isopropyl)carbamoyl)phenoxy) hexanoic acid; 6-(2-(2-((4-(furan-2-yl)phenyl)(isopropyl) amino)-2-oxoethyl)phenoxy)hexanoic acid; 6-(2-(2-(4-(furan-2-yl)phenyl)piperidine-1-carbonyl)phenoxy) hexanoic acid; 6-(2-(2-(4-(furan-2-yl)phenyl)azetidine-1-carbonyl)phenoxy)hexanoic acid; 6-(2-((3-(4-(furan-2-yl) benzoyl)isoxazol-4-yl)methyl)phenoxy)hexanoic acid; 6-((4-((4-(furan-2-yl)-N-isopropylbenzamido)methyl)pyrrolidin-3-yl)oxy)hexanoic acid; 6-((4-((4-(furan-2-yl)-N-isopropylbenzamido)methyl)morpholin-3-yl)oxy)hexanoic acid; and 6-(2-(1-(4-(furan-2-yl)benzyl)-4-methyl-1H-imidazol-2-yl)phenoxy)hexanoic acid (see, U.S. Patent Application Publication No. 20160023991).

Without wishing to be bound by the theory, it is believed that while the PPARδ agonist increases the expression of the genes coding for mitochondrial β-oxidation pathway mutant proteins that are unstable but partially active, trimetazidine or its derivatives, act to indirectly stabilize the PPARδ agonist-enhanced produced mutant protein(s). The combination treatment is thus superior to treating patients with either drug individually.

As shown below, PPARδ agonists act synergistically with TMZ compounds in increasing activity of β-oxidation pathway enzymes, such as VLCAD and MCAD. Therefore provided is a method of treating a patient having a disorder caused by a mutation, e.g. a missense mutation, in an enzyme of the β-oxidation pathway and/or fatty acid mitochondrial transport, in a patient comprising inhibiting activity of an enzyme of the β-oxidation pathway downstream in the β-oxidation pathway to the enzyme having the missense mutation, thereby increasing activity of the an enzyme of the β-oxidation pathway and/or fatty acid mitochondrial transport having the missense mutation and administering to the patient a PPARδ agonist when the enzyme activity is inhibited, e.g., with TMZ. In aspects, a combination dosage form is provided comprising an effective amount of a PPARδ agonist to increase β-oxidation activity in a patient, and trimetazidine, a derivative thereof, an analog thereof, an isostere thereof, a pharmaceutically-acceptable salt thereof, or a pharmaceutically-acceptable ester thereof.

EXAMPLE

In vitro experimental results presented herein provide evidence for the potential efficacy of TMZ in treating patients with fatty acid β-oxidation disorders. VLCAD, MCAD, TFP deficiencies, caused by missense mutations in the ACADVL, ACADM, HADHA and/or HADHB genes, coding for the two ACAD enzymes and the TFP, respectively. The evidence presented includes: (1) Significant increase in VLCAD and MCAD enzyme activity in patient's cell extracts with all being proportional with the increasing amounts of TMZ in the cell culture medium. (2) Increase in in situ VLCAD, MCAD, and TFP protein components signal presence proportional to the increase in the presence TMZ in culture. (3) Key acylcarnitine metabolites measured in the culture media of VLCAD deficient cells have shown profiles consistent with improvements that were best at 0.25 μM TMZ in one patient cell line tested. The preliminary results for TMZ effect warrant filing a patent while expanding the in vitro and in vivo investigation with other TMZ derivatives mentioned above. Since TMZ is already an FDA-approved drug, clinical trials on critical cases can be started with the necessary special approvals.

Materials and Methods

Cell Lines and Culture

Cells from patients with VLCAD deficiency FB834 was purchased from Coriell Institute (Cat #GM11408). Others tested including FB671 and FB833, were obtained from patients. The patient had recurrent rhabdomyolysis episodes every 4 weeks and is treated with IV fluids during these episodes. The patient skin biopsies for fibroblast culture were performed on a clinical basis with written informed consent from patients and/or parents. Fibroblasts were cultured in Dulbecco's Modified Eagle Medium (DMEM) supplemented with 15% fetal bovine serum and 100 μg/ml penicillin/streptomycin, 4.5 g/l glucose, 4 mM glutamine and 2 mM pyruvate. Molecular analysis of fibroblast cells FB671 revealed the patient is heterozygote for a VLCAD L540P variant on one allele and has a 9 bases insertion resulting in the additional Asp-Gly-Ala three amino acid insertion at aa 530 (precursor numbering). Molecular analysis of fibroblast cells FB833 revealed heterozygote for two missense mutations causing V174M and E609K replacements. Other fibroblasts used are FB831 homozygous for the MCAD K304E common (>90% of MCAD case) variant, which was also obtained from Coriell Institute (Cat #GM13275), and FB830 homozygous for the HADHA homozygous for the c.1528G>C (p.E510Q, or E474Q with respect to the mature HADHA protein) mutation, Coriell Institute (Cat #GM20266). FB842 is a fibroblast cell line obtained from a patient with LCKAT deficiency, with an S70P amino acid residue replacement on HADHB allele of TFP and a splicing abnormality in the other allele.

Trimetazidine, 1-(2,3,4-trimethoxybenzyl)piperazine, was obtained from Sigma-Aldrich Co., St. Louis, Mo. The powder was dissolved in phosphate buffer saline, PBS, as a 200 mM stock solution. Amounts were added appropriately directly to cell culture media in T175 flasks when the cultures were about 85-90 confluent. The cultures were allowed to grow for 48 h at 3° C., and then harvested. Harvested cell pellets were stored at −80° C. until immune and enzymatic assays analyses. One to 1.5 ml media samples were also stored at −80° C. for acylcarnitines.

Confocal Imaging and Immunofluorescence Intensity Quantification of Fibroblasts

Fibroblasts from VLCAD deficient patient that were untreated and treated with varying concentrations of TMZ were seeded at a concentration of $5\times10^4$ cells/ml on tissue culture-treated glass cover slips and allowed to grow overnight with various TMZ concentrations included at 37° C. in a 5% $CO_2$, 95% humidity incubator. Cells were then fixed in 4% paraformaldehyde for 10 min followed by 0.1% Triton X100 cell permeabilization and further blocked after brief washings in 5% donkey serum (Jackson ImmunoResearch, West Grove, Pa.) for 1 hour on ice. This was followed by double primary antibody incubation with anti-VLCAD antibody, anti-TFP, or anti MCAD generated by Cocalico Biologicals, or obtained from Abcam, Cambridge, Mass., or Santa Cruz, Calif., at 4° C. overnight. After brief washing, cells were further incubated with donkey anti-rabbit secondary antibody Alexa Fluor 488 (Invitrogen, Grand Island, N.Y.) for VLCAD. Nuclei were counterstained with DAPI. The cover slips were then mounted using mounting media before imaging. All the images were taken using a Olympus Confocal FluoView FV1000 microscope at a magnification of 40 and 60×. Immunofluorescence intensity was quantified using NIH ImageJ software.

ETF Fluorescence Reduction ACAD Activity Assay

This is the standard enzyme assay we use to measure ACAD enzyme activity at the picomoles level in tissues and in cell culture. Assay protocol with the key ingredient being ETF (electron transfer flavoprotein) that is isolated from pig liver has been published (Vockley et al., 2000).

Level of Expression of VLCAD

The effect of increasing amounts of TMZ on ACADVL gene expression in FB834 cells was monitored using standard qRT-PCR protocol. Messenger RNA transcription levels of ACADVL (MIM: 609575) for the patient's fibroblasts cell lines with VLCAD deficiency untreated and treated with TMZ were quantified via qRT-PCR with an Applied Biosystems StepOnePlus instrument using TaqMan® Gene Expression Master Mix (from ThermoFisher Scientific). The reference sample was fibroblasts with no VLCAD deficiency. Human GAPDH was used as an endogenous control. Commercial primers for ACADVL and GAPDH were used using and TaqMan™ Gene Expression Assay (ThermoFisher Scientific), which consists of a pair of unlabeled PCR primers and a TaqMan probe with a FAM™ or VIC® dye label on the 5"-end and minor groove binder (MGB) and non-fluorescent quencher (NFQ) on the 3"-end. The relative quantity RQ of the samples was compared between the reference sample, treated VLCAD deficiency cell lines untreated and treated with TMZ.

Acylcarnitine Levels Determination

Acylcarnitines level determination was performed at CHOPS, Philadelphia, Pa.

Mitochondrial Superoxide Production

Cell suspension containing $1\times10^5$ cells per mL were incubated for 25 min at 37° C. with 150 nM Mitotracker Green (Invitrogen, Grand Island, N.Y.) for mitochondrial mass evaluation or for 15 min at 37° C. with 5 µM Mitosox Red, from Invitrogen, for superoxide production measurement. After incubation, 10,000 cells samples were analyzed in a Becton Dickinson FACSAria II flow cytometer.

Experimental Evidence

Figure 3:
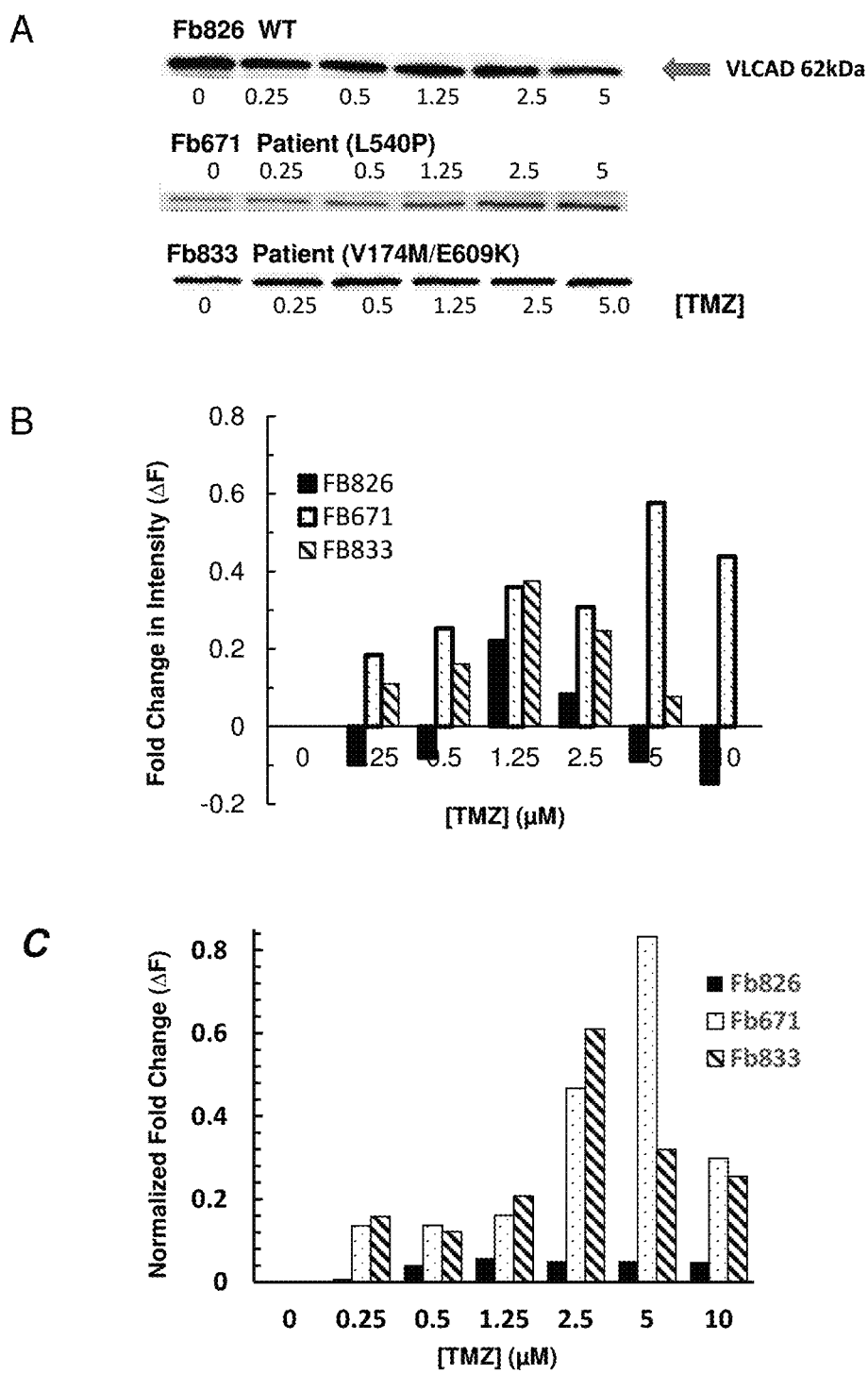
FIG. 3. Effect of the presence of increasing amounts of TMZ for 48 hrs on VLCAD antigens' presence in FB833 and FB671 fibroblast cells as detected by western blot, A. Graph B, shows the observed changes normalized to GAPDH in the western blot, A, quantified using imageJ software. Graph B shows of the observed changes in the presence of VLCAD antigen normalized to DAPI detected in situ by immunostaining.
Figure 4:
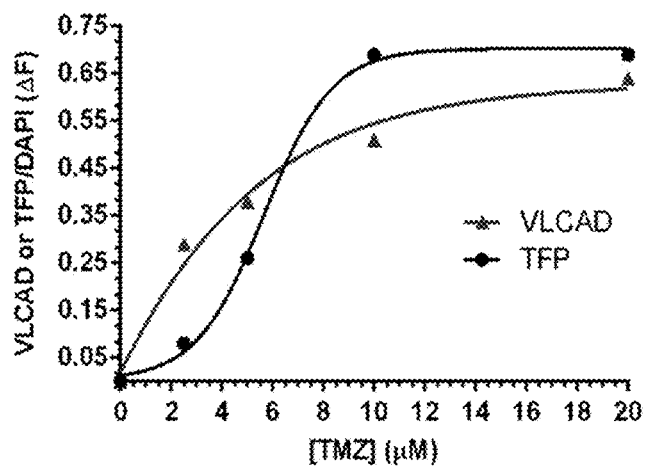
FIG. 4. Effect of the presence of increasing amounts of TMZ for 72 hrs on VLCAD and presence of TFP (combined α- and β-subunit) antigens' presence in FB834 fibroblast cells. Y axis represents fold change (ΔF) in relative VLCAD antigen present normalized to DAPI (for nuclear presence.)
Figure 5:
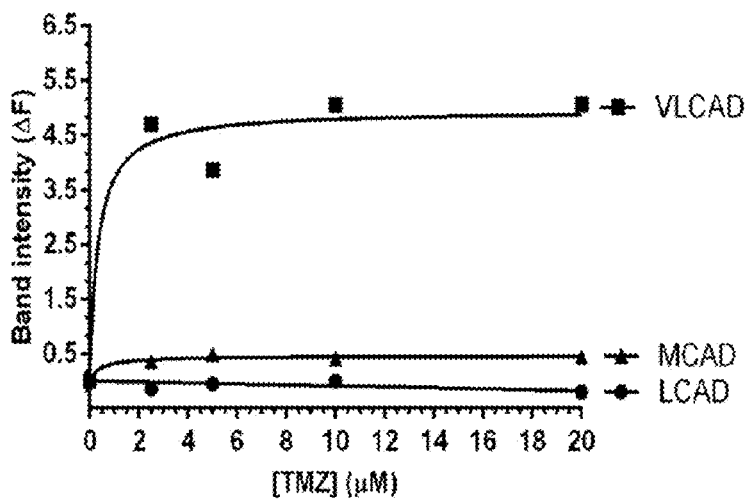
FIG. 5. Effect of the presence of increasing amounts of TMZ for 48 hrs on VLCAD, MCAD, and LCAD antigens presence in FB834 fibroblast cells as detected by western blots. Y axis represents the fold change (ΔF) in protein presence.

Protein Presence Changes Detected by Western Blots and Cell Immunostaining Assays Monitoring the VLCAD presence detected by western bloting in the VLCAD deficient cell line FB833 and FB671 shows proportional increase in VLCAD signal in patients' cells when treated with increased amount of TMZ incubated for 48 hrs, FIGS. 3A and B. Monitoring of VLCAD presence detected by immunostaining in the same VLCAD deficient cell lines shows proportional increase in VLCAD signal in patients' cells when treated with increased amount of TMZ incubated for 72 hrs as well, FIG. 3C. In situ monitoring of VLCAD presence detected by immunostaining in the VLCAD deficient cell line FB834 and similarly it shows proportional increase in VLCAD signal in patients' cells when treated with increased amount of TMZ incubated for 72 hrs, FIG. 4. FIG. 4 shows the fold increase in the total VLCAD and TFP detected using fluorescence (green) normalized to total nuclear DAPI fluorescence (blue). FIG. 5 shows the VLCAD, MCAD, and LCAD signal detected by western blotting. While VLCAD shows more significant response compared to MCAD, this is consistent with published reports on the inhibition of LCKAT, the long chain enzyme, more significantly compared to the medium chain 3-ketoacyl-CoA thiolase. LCAD was unafftected in this cell line, but this may be expected.

Figure 6:
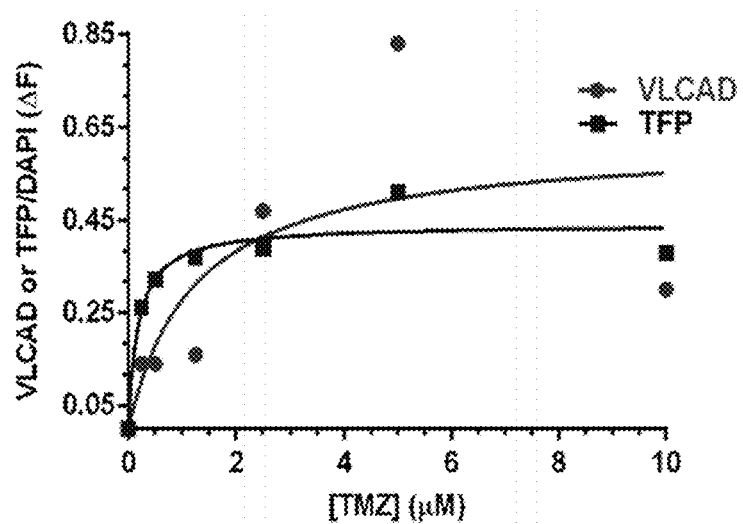
FIG. 6. Effect of the presence of increasing amounts of TMZ for 72 hrs on VLCAD and TFP (combined α- and β-subunit) antigens' presence in FB671 fibroblast cells as detected by Immunostaining and quantification by ImageJ. Y axis represents the fold change (ΔF) in protein presence.

In situ detection of VLCAD presence, detected by immunostaining in the VLCAD deficient cell line FB671 shows proportional increase in VLCAD signal in patients' cells when treated with increased amount of TMZ incubated for 72 hrs, FIG. 6. FIG. 6 shows the fold increase in the total VLCAD green fluorescence normalized to total nuclear DAPI blue fluorescence.

Figure 7:
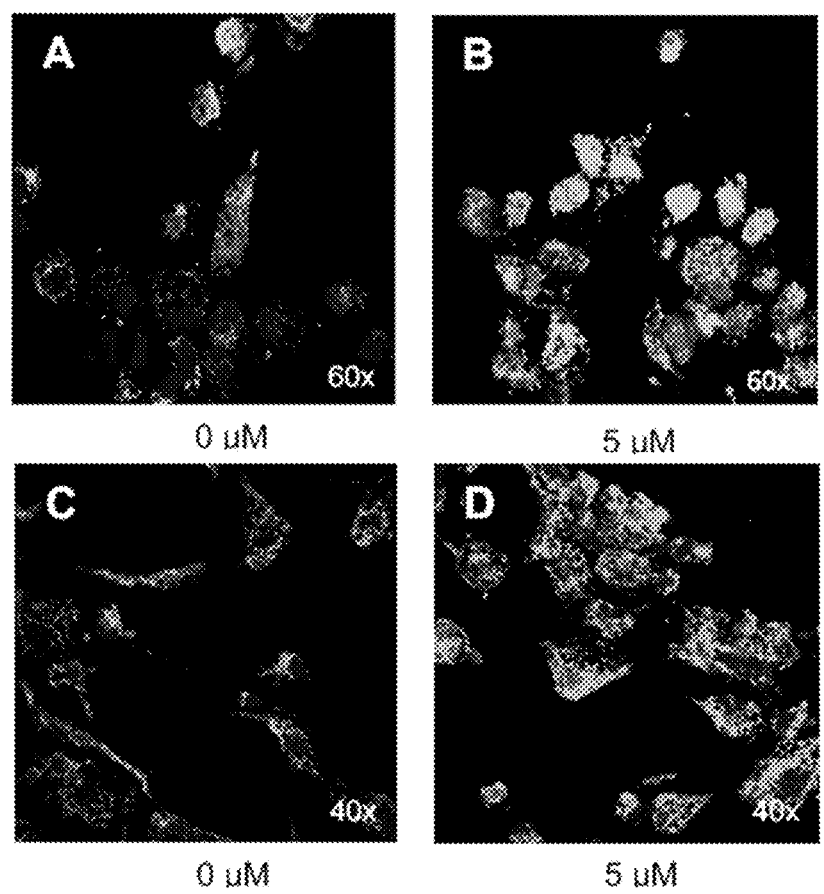
FIG. 7. Immunofluorescence staining for anti-MCAD (upper panel A & B) and anti-TFP (lower panel C & D) in MCAD deficient patient fibroblast FB831 in response to indicated TMZ treatment.
Figure 8:
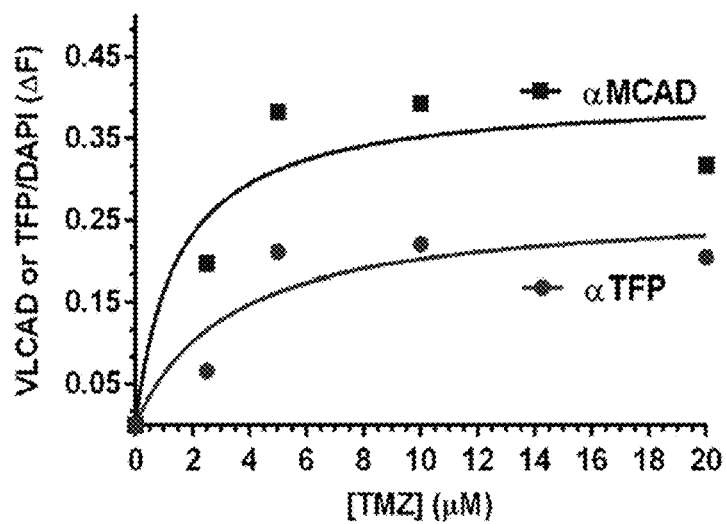
FIG. 8. Effect of the presence of increasing amounts, 2.5, 5, 10, and 20 µM, of TMZ in culture media for 72 hrs on MCAD (squares) and TFP antigen (circles) presence in FB831 MCAD deficient fibroblast cells. Y axis represents fold change (ΔF) in relative MCAD and TFP antigen present normalized to DAPI (for nuclear presence).

An increase in MCAD antigen signal was observed in the MCAD deficient cell line FB831, increasing from barely detectable to detectable with TMZ concentration of 5 µM. FB831 was also immunostained for TFP presence and increase of antigen was detected peaking at 5 µM of TMZ, (FIGS. 7 and 8).

Figure 9:
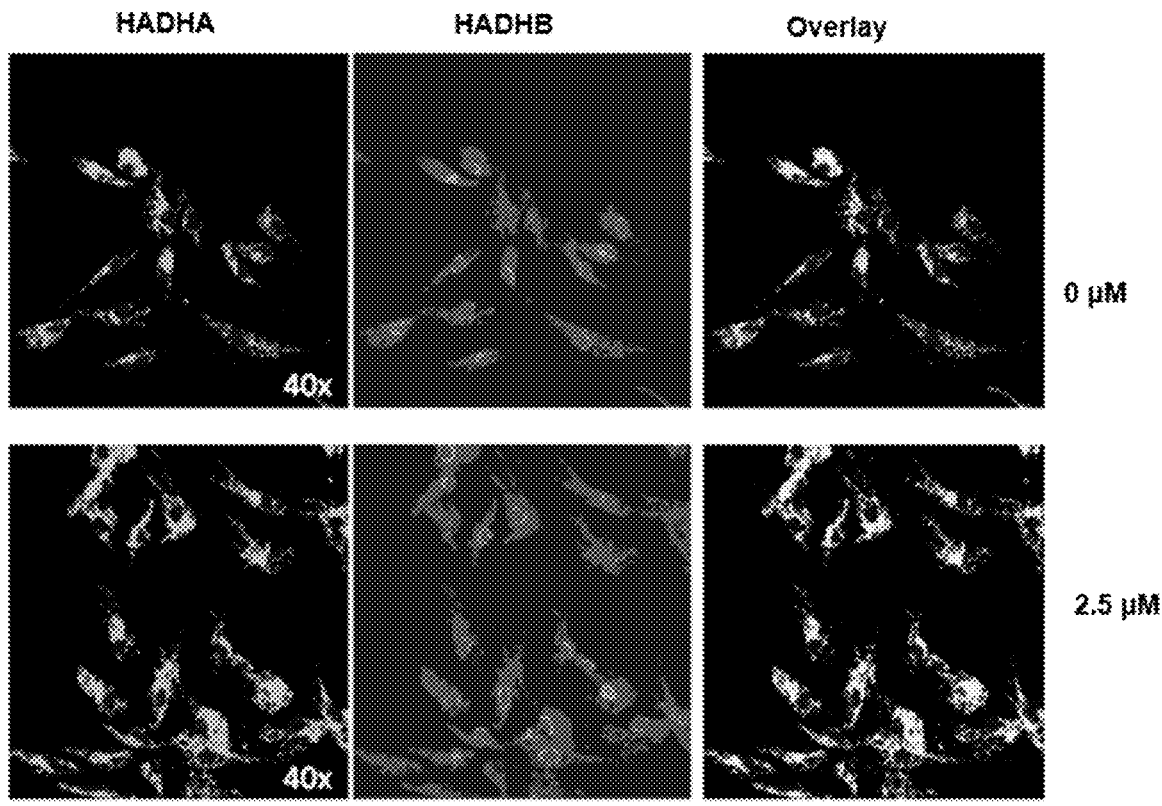
FIG. 9. Immunofluorescence staining for anti-HADHA, specific for the α-subunit or anti-HADHB, specific for the β-subunit, or anti-TFP, which detects both the α-subunit and β-subunit. in LCHAD deficient patient fibroblast Fb830 in response to indicated TMZ treatment.
Figure 10:
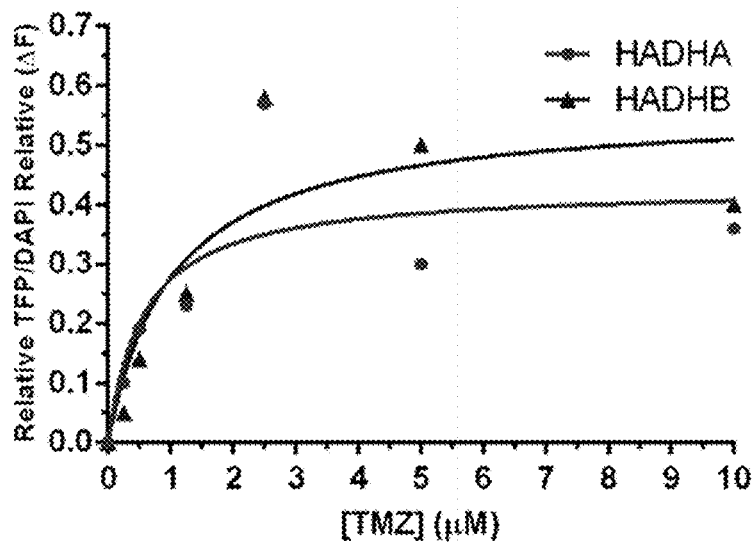
FIG. 10. Effect of the presence of increasing amounts, 0.25, 0.5, 1.25, 2.5, 5.0 and 10 µM, of TMZ in culture media for 72 hrs on HADHA (circles) and HADHB antigen (triangles) presence in FB830 LCHAD deficient fibroblast cells. Y axis represents fold change (ΔF) in relative HADHA or HADHB antigen present normalized to DAPI (for nuclear presence).
Figure 11:
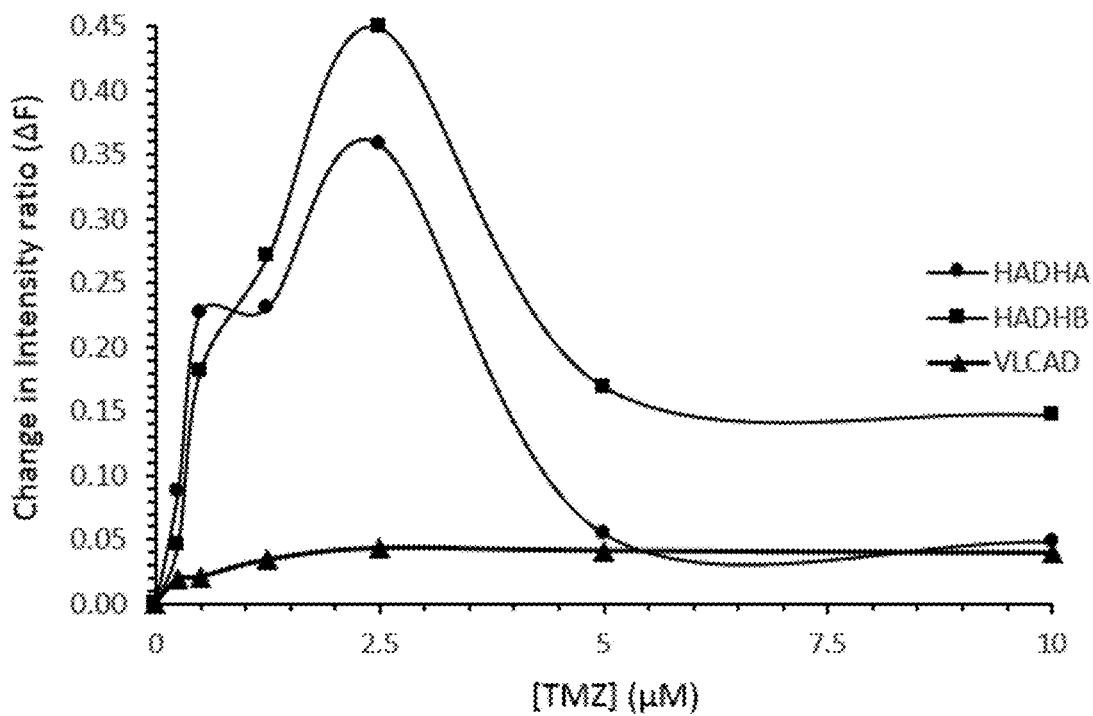
FIG. 11. Effect of the presence of increasing amounts, 0.25, 0.5, 1.25, 2.5, 5.0 and 10 µM, of TMZ in culture media for 72 hrs on HADHA (circles), HADHB antigen (squares), and VLCAD (triangles) presence in FB842 LCKAT-deficient fibroblast cells with an HADHB S70P amino acid replacement. Y axis represents fold change (ΔF) in relative HADHA or HADHB antigen present normalized to DAPI (for nuclear presence).

An increase in HADHA and HADHB antigen signal was observed in the LCHAD (part of HADHA subunit of TFP) deficient cell line FB830, increasing maximum at TMZ concentration of 2.5 µM. FB830 was also immunostained, (FIGS. 9 and 10). FIG. 11 shows the effect of the presence of increasing amounts, 0.25, 0.5, 1.25, 2.5, 5.0 and 10 µM, of TMZ in FB842 LCKAT deficient fibroblast cells on HADHA, HADHB, and VLCAD presence.

VLCAD Enzyme Activity

In this current study, the ETF fluorescence reduction assay was used, which is a superior and more sensitive and reliable assay for measuring ACAD enzyme activity. In two patients' cell lines, FB834 and FB671, VLCAD activity significantly increased proportionally with increasing concentrations of TMZ in the cell culture media incubated for 48 hrs. The fold increase in VLCAD enzyme activity is essentially matching the fold increase in antigen presence as observed by in situ immunostaining, FIG. 4.

Figure 12:
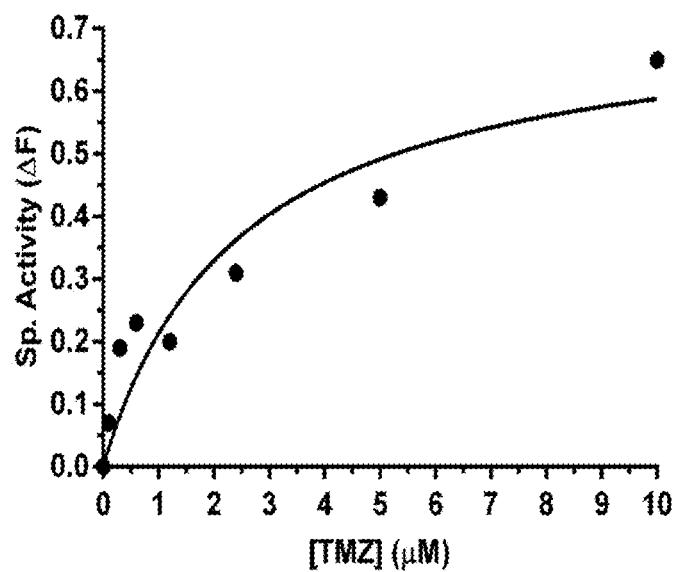
FIG. 12. Effect of the presence of increasing amounts of TMZ for 48 hrs on VLCAD activity using C16-CoA as substrate, measured by the ETF fluorescence reduction assay in FB834 fibroblast cells. Y axis (ΔF) represents fold change in specific activity.
Figure 13:
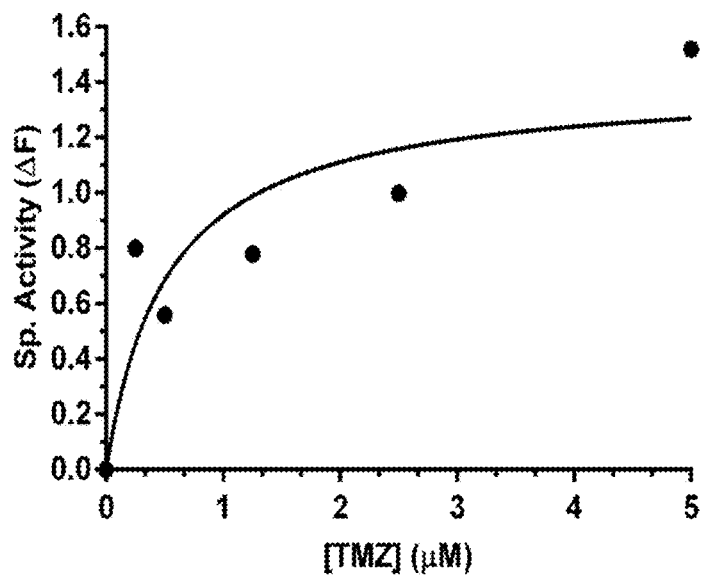
FIG. 13. Effect of the presence of increasing amounts of TMZ for 48 hrs on VLCAD activity using C16-CoA as substrate, measured by the ETF fluorescence reduction assay in FB671 fibroblast cells. Y axis (ΔF) represents fold change in specific activity.

FIGS. 12 and 13 show the relative increase in VLCAD activity at various concentrations of TMZ, in two cell lines from patients with VLCAD deficiency, FB834 and FB671, respectively. In both cases VLCAD enzyme activity increased with increasing amounts of TMZ. The increase varied in magnitude by ~0.6 and ~1.3 fold, respectively.

Level of Expression of VLCAD

Figure 14:
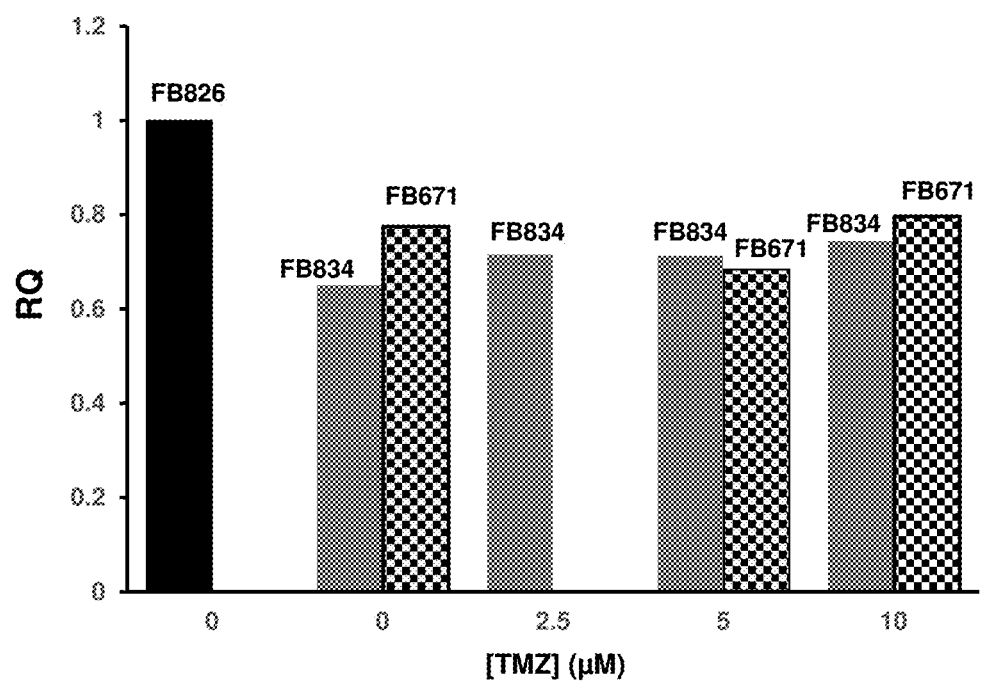
FIG. 14. Effect of the presence of increasing amounts of TMZ, 0, 2.5, 5, and 10 µM on ACADVL expression in FB834 and TMZ at 0, 5, and 10 µM in FB671 compared to control (FB826) when incubated for 48 hr measured in terms of VLCAD RNA signal presence.

No significant effect was observed on ACADVL expression in FB834 with increasing amounts of TMZ (FIG. 14).

Acylcarnitine Levels

Figure 15:
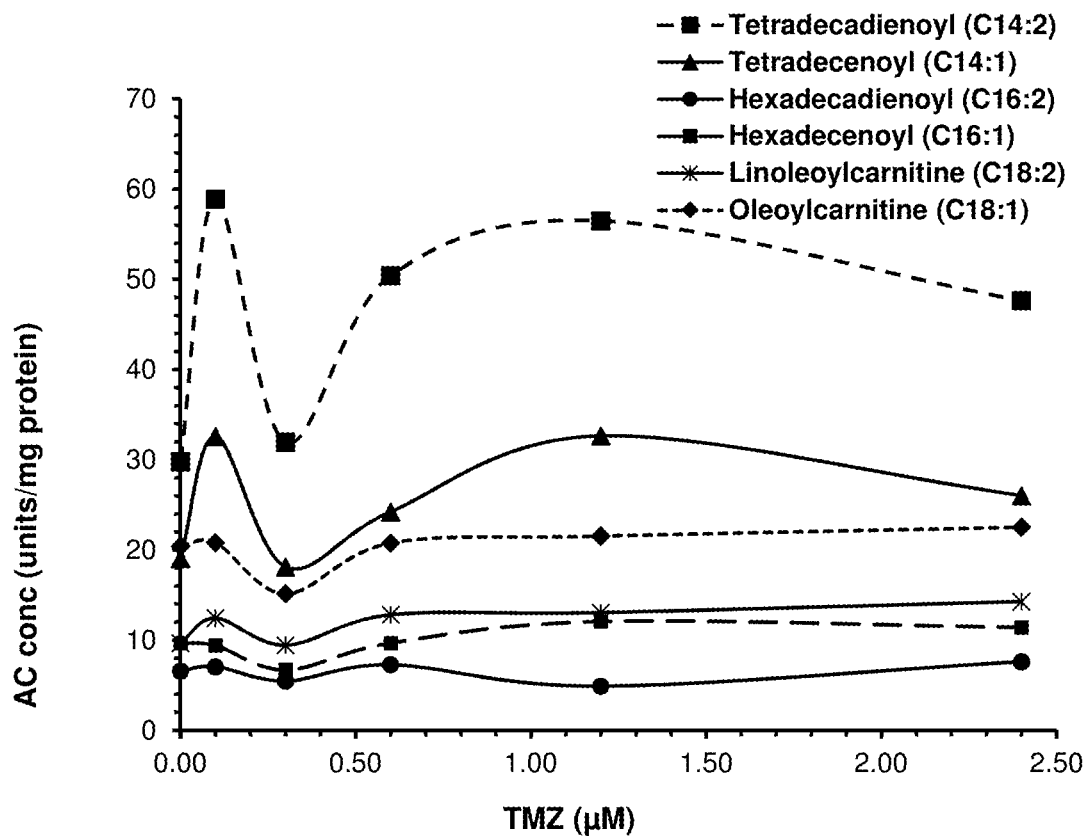
FIG. 15. Changes in the concentrations of acylcarnitine induced by the presence of TMZ at various concentrations for patient cell line FB834. Values shown for C16-carnitine are divided by 10.
Figure 16:
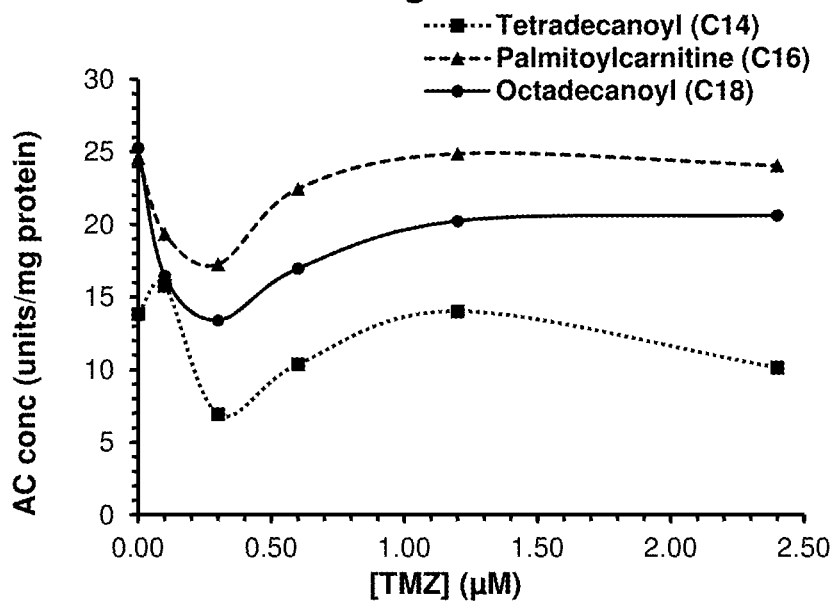
FIG. 16. Changes in the concentrations of saturated long chain acylcarnitines induced by the presence of TMZ at various concentrations for patient cell line FB834. Values shown for C16-carnitine are divided by 10.
Figure 17:
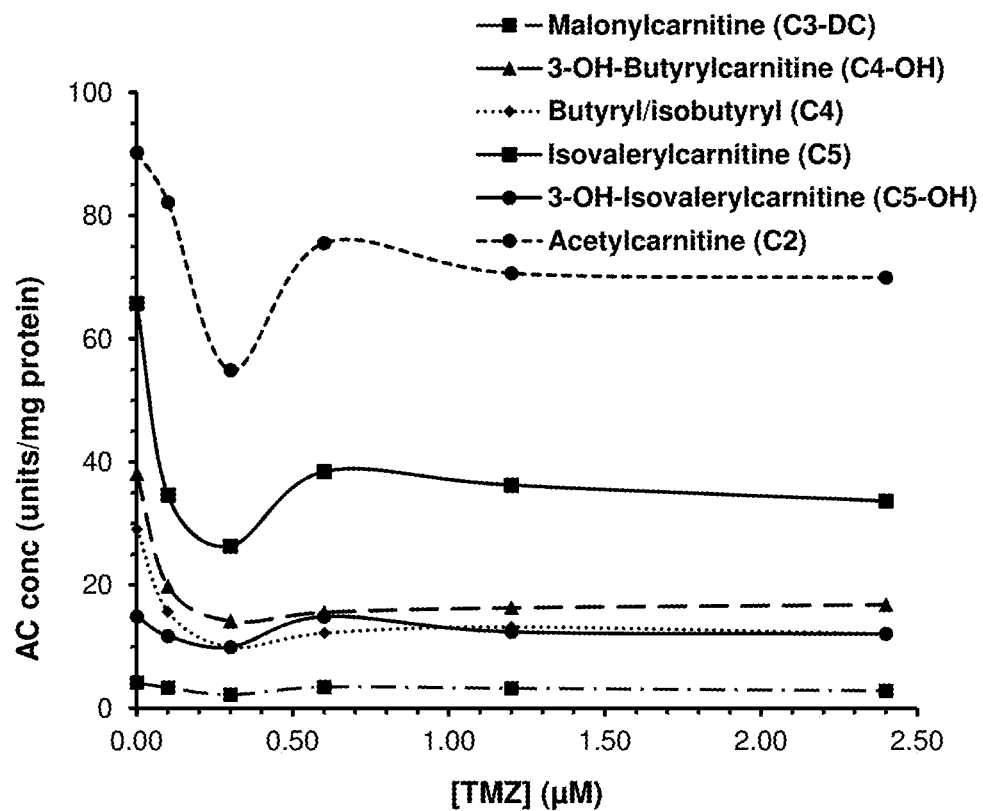
FIG. 17. Changes in the concentrations of short chain acylcarnitine induced by the presence of TMZ at various concentrations for patient cell line FB834 (mutation unpublished). Values shown for acetylcarnitine and Ca-carnitine are divided by 100 and 10, respectively.

Most of the acylcarnitines, as shown in FIGS. 15-17, were reduced with maximum reduction at ~0.25 µM level. The percentage drop in each acylcarnitine ranges ~30-40%. Such a drop would be clinically significant.

Mitochondrial Superoxide Production

Figure 18:
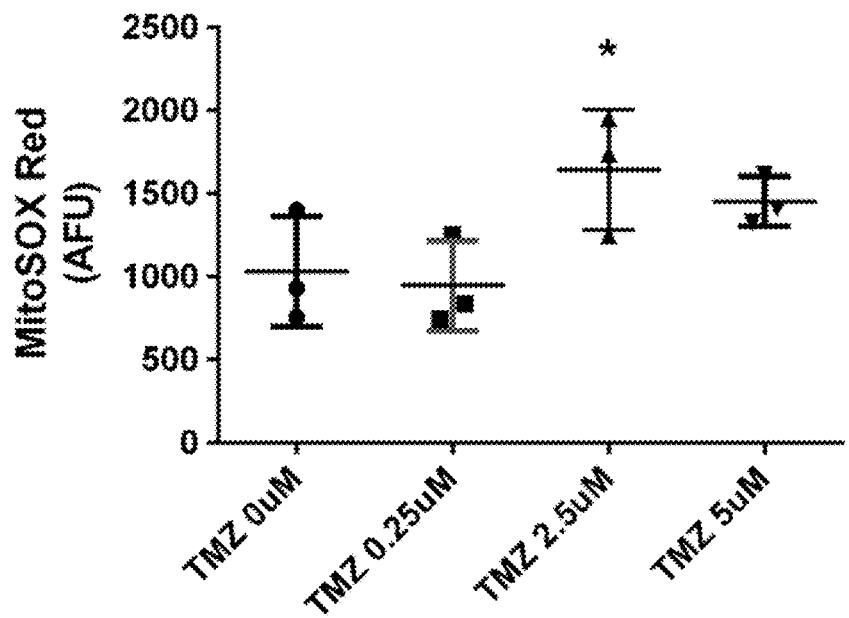
FIG. 18. Effect of various concentrations of TMZ on the presence of ROS as measured by MitoSOX Red in the VLCAD deficient cell line FB834.
Figure 19:
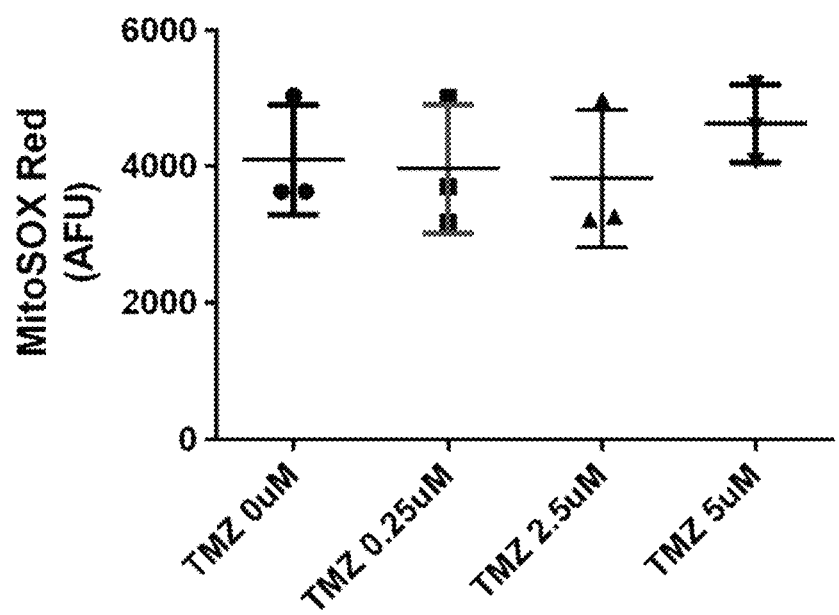
FIG. 19. Effect of various concentrations of TMZ on the presence of ROS as measured by MitoSOX Red in the VLCAD deficient cell line FB671.

The reactive oxygen species (ROS) has been observed to be higher in fibroblast cells from patients with VLCAD deficiency compared to control cell lines. The mechanism is unknown and the contribution of higher ROS on the pathological phenotype has not been determined. ROS was measured in FB834 and FB671 at various concentrations of TMZ, FIGS. 18 and 19, respectively.

CONCLUSION

The efficacy of this drug to improve the parameters of VLCAD viability at the molecular level in deficient cell lines is evident from the above in vitro experimental results. Key end points of validated experimental tests were met, including increase in VLCAD enzyme activity, increase in VLCAD protein presence observed in situ, and in case of VLCAD deficiency lower C16 present in the media at lower amount of TMZ, ~2.5 μM. The concentration-dependent increase in detected in situ antigen and in enzyme activity measured in vitro was not a function of increased ACADVL gene expression as shown by RT-qPCR data, but rather decreased turnover.

While the unexplained increase in ROS was observed in FB671 and in FB834 VLCAD deficient cell line, the increase in ROS is still not understood, and secondary unknown indirect effects unrelated to the VLCAD deficiency cannot be ruled out. Clinically, the patient, where FB671 was collected, has shown increase in inflammation parameters that could be related to such higher ROS and so other therapeutic interventions could be considered.

The increase in VLCAD enzyme activity was variable among the two patient cell lines tested FB834 and FB671. This is also consistent with VLCAD mutants expected to vary in their stability and consistent with mechanism of action of the drug proposed above. While some missense mutations will lead to completely crippled VLCAD, others that have milder effect on protein stability may respond well to TMZ treatment, and hence patients would be expected to respond differently and it may become necessary to adjust/customize TMZ doses according to the patient. While TMZ is one among others that act as inhibitors of fatty acid β-oxidation, other inhibitors of fatty acid β-oxidation with potentially can induce similar improvements in protein presence.

Figure 20:
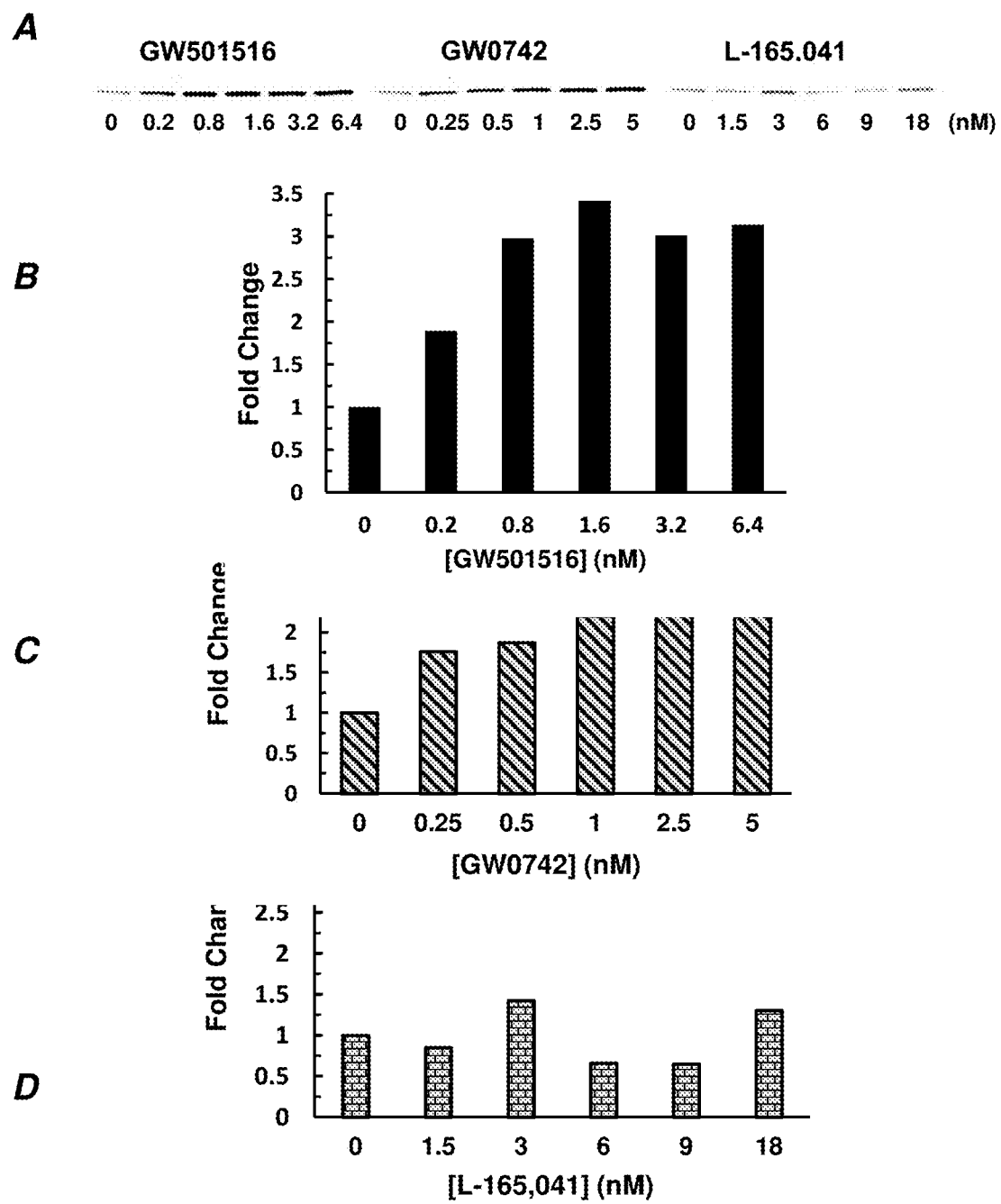
FIG. 20. Effect of various concentrations of GW501516, GW0742, and L-165,041 PAPRd agonists on VLCAD presence as observed on western blots (VLCAD (62 kDa)). Quantitation of the bands were performed using ImageJ software.
Figure 21:
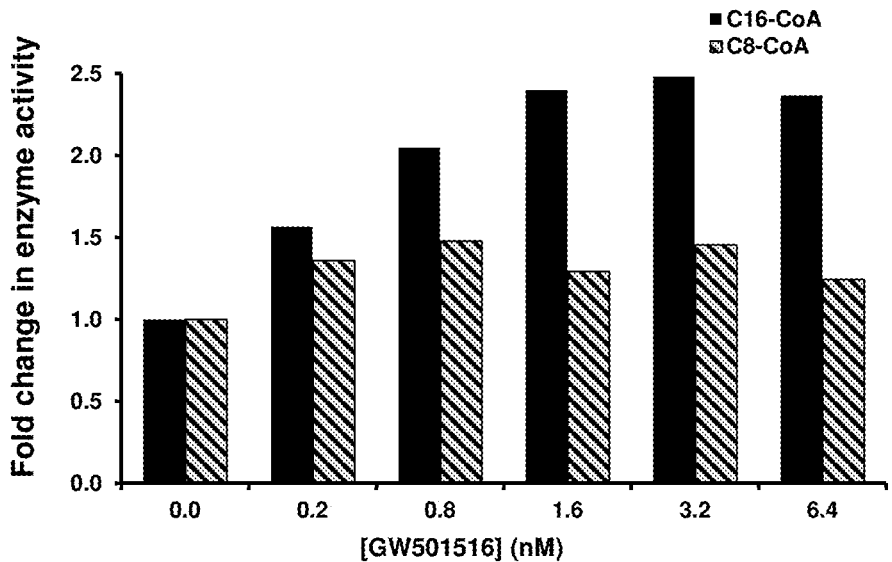
FIG. 21. Effect of various concentrations of GW501516 (GW16) on VLCAD enzyme activity in deficient cell line FB833 treated for 48 hrs using the ETF fluorescence reduction assay and C16-CoA as substrate at 30 μM. MCAD activity was measured using C8-CoA as substrate at 30 μM.
Figure 22:
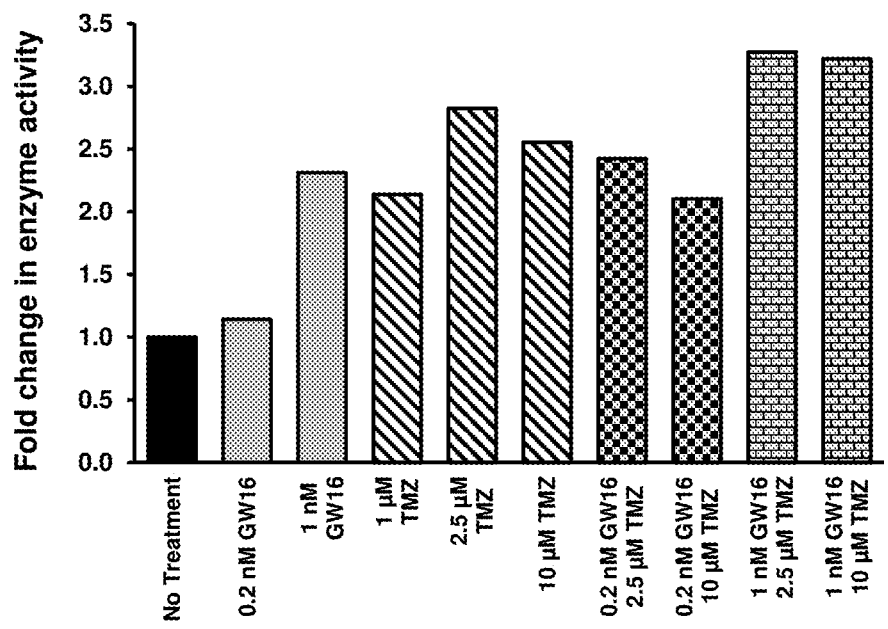
FIG. 22. Synergistic effect of trimetazidine and GW501516 (GW16) combination treatment of VLCAD deficient cell line FB833 for 48 hrs. Effect of treating with 1, 2.5, and 10 μM trimetazidine, 0.2 and 1 nM GW501516, and the combinations of TMZ and indicated on VLCAD enzyme activity in deficient cell line FB833. Enzyme activity was measured using the ETF fluorescence reduction assay and C16-CoA as substrate at 30 μM. All values are in fold change compared to no treatment normalized as 1 (100%).
Figure 23:
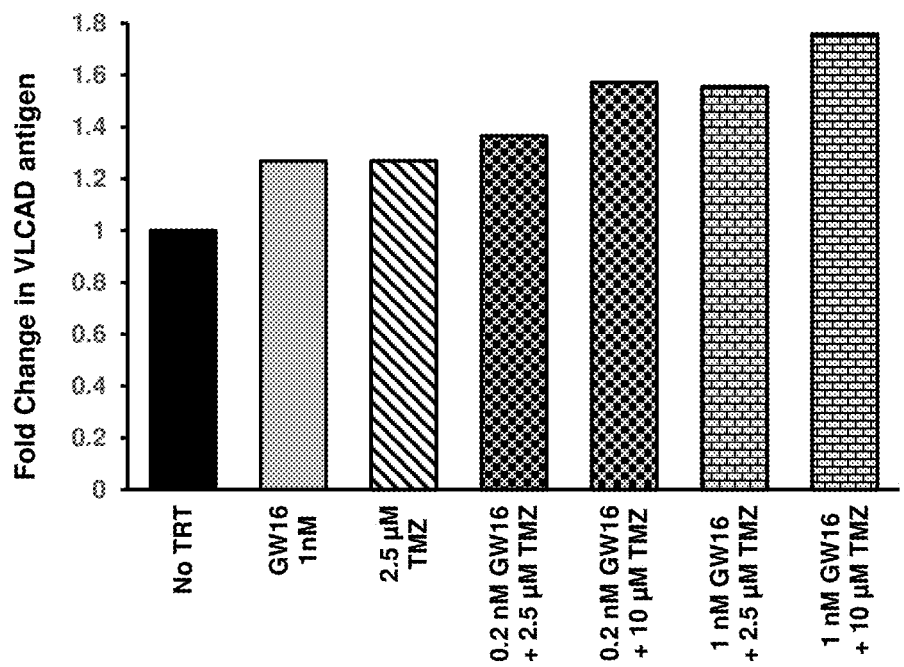
FIG. 23. Effect of trimetazidine and GW501516 (GW16) combination treatment of VLCAD deficient cell line FB833 for 72 hrs on VLCAD presence detected by immunostaining microscopy. Shown is the effect of treating with 2.5 μM trimetazidine or 1 nM GW501516 (GW16), and the combinations of TMZ and indicated in figure. VLCAD antigen presence in situ was observed using cell immunostaining microscopy and quantitated using ImageJ software. All values are in fold change compared to no treatment normalized as 1 (100%).

Three PPARδ were tested for efficacy to enhance expression of the ACADVL and ACADM genes. These were GW501516, GW0742 (a.k.a. GW610742), and L-165,0411. While the former two have shown increase in VLCAD antigen signal in FB833, the latter one did not show as much (FIG. 20). Hypothesizing that the mechanism of the PPARδ will work well to complement the effect of trimetazidine, trimmetazidine and GW501516 were tried in combination. Enhancement with both of them present was highest at 10 μM and 1 nM, respectively, see FIGS. 21-23.

The following clauses are illustrative of various aspects of the invention:

Clause 1: A method of treating a disorder caused by a mutation, for example a missense mutation, in any of the enzymes and/or proteins of the β-oxidation pathway and/or fatty acid mitochondrial transport in a patient in need thereof, comprising administering to the patient an effective amount of an inhibitor of activity of an enzyme of the β-oxidation pathway downstream in the β-oxidation pathway of the enzyme having the mutation, thereby increasing activity of the enzyme of the β-oxidation pathway of fatty acid mitochondrial transport having the mutation, wherein the product of the enzyme having the mutation stabilizes that unstable enzyme, or one or more substrates or products of the downstream enzyme binds, for example allosterically, to the mutant enzyme and stabilize that unstable enzyme.

Clause 2: A method of increasing activity of a protein and/or enzyme of the β-oxidation pathway and/or fatty acid mitochondrial transporter protein/enzyme, the protein and/or enzyme having a mutation, for example a missense mutation, resulting in loss of its activity or stability, in a patient in need thereof, comprising administering to the patient an effective amount of an inhibitor of activity of an enzyme of the β-oxidation pathway downstream in the β-oxidation pathway of the enzyme having the mutation, thereby increasing activity of the upstream enzyme of the β-oxidation pathway and/or a fatty acid mitochondrial transporter protein/enzyme having a mutation, wherein the product of the enzyme having the mutation binds back and stabilizes that protein/enzyme.

Clause 3: The method of clause 1 or clause 2, wherein the mutation is a missense mutation, optionally a missense mutation that does not result in a complete loss of enzyme activity, e.g., the mutant enzyme still has some partial activity that is stabilized by the method.

Clause 4: The method of any of clauses 1-3, wherein the mutated enzyme is MCAD.

Clause 5: The method of any of clauses 1-4, wherein the mutation is K304E.

Clause 6: The method of any of clauses 1-5 wherein the mutated enzyme is VLCAD.

Clause 7: The method of any of clauses 1-3 and 6, wherein the mutation is L540P.

Clause 8: The method of any of clauses 1-7, wherein the mutated enzyme is an HADHA or HADHB subunit of TFP.

Clause 9: The method of any of clauses 1-3 and 8, wherein the mutation is E510Q of HADHA.

Clause 10: The method of any of clauses 1-3 and 8, wherein the mutation is R247C of HADHB.

Clause 11: The method of any of clauses 1-10, wherein the enzyme of the β-oxidation pathway downstream in the β-oxidation pathway to the enzyme having the missense mutation is long-chain 3-ketoacyl-CoA thiolase (LCKAT).

Clause 12: The method of any of clauses 1-11, wherein activity of an enzyme of the β-oxidation pathway downstream in the β-oxidation pathway to the enzyme having the missense mutation is inhibited by trimetazidine or a derivative thereof, or a pharmaceutically-acceptable salt or ester thereof.

Clause 13: The method of any of clauses 1-12, wherein the activity of an enzyme of the β-oxidation pathway downstream in the β-oxidation pathway to the enzyme having the missense mutation is inhibited by a trimetazidine derivative, or a pharmaceutically-acceptable salt or ester thereof.

Clause 14: The method of clause 13, wherein the trimetazine derivative has the structure:

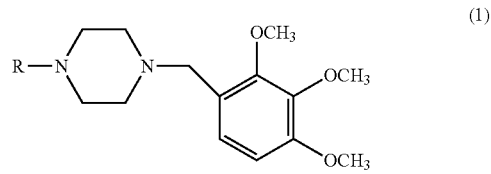

(1)

where R is a 5 to 7 member hydrocarbon or heterocyclic group substituted with one or more $C_1$-$C_6$ hydrocarbon groups.

Clause 15: The method of clause 14, wherein R is 2,2,5,5-tetramethylpyrrolinyl that is optionally substituted at its 4 position with a $C_1$-$C_6$ hydrocarbon group, such as a phenyl group.

Clause 16: The method of clause 14, wherein R is 2,2,5,5-tetramethyl-4-phenylpyrrolinyl.

Clause 17: The method of any of clauses 1-16, wherein the enzyme having the missense mutation is in a mitochondrial membrane fatty acid transport protein.

Clause 18: The method of clause 17, wherein the mitochondrial membrane fatty acid transport protein is carnitine palmitoyltransferase I (CPT I) or carnitine palmitoyltransferase 2 (CPT II).

Clause 19: The method of any of clauses 1-18, further comprising administering to the patient an amount of a Peroxisome Proliferator-Activated Receptor delta (PPARδ) agonist effective to increase activity of the β-oxidation pathway in a patient.

Clause 20: The method of clause 19, wherein the PPARδ agonist is chosen from GW501516, GW0742, or any PPARδ agonist that enhances production of an enzyme of the β-oxidation pathway and/or fatty acid mitochondrial transport having a misense mutation.

Having described this invention, it will be understood to those of ordinary skill in the art that the same can be performed within a wide and equivalent range of conditions, formulations and other parameters without affecting the scope of the invention or any embodiment thereof.

REFERENCES

Aliefendioglu et al. (2007). A newborn with VLCAD deficiency. Clinical, biochemical, and histopathological findings. Eur J Pediatr 166, 1077-1080.

Ancerewicz et al. (1998). Structure-property relationships of trimetazidine derivatives and model compounds as potential antioxidants. Free Rad. Biol Med 25(1):113-120.

Andresen et al. (1999). Clear correlation of genotype with disease phenotype in very-long-chain acyl-CoA dehydrogenase deficiency. Am. J. Hum. Genet. 64, 479-494.

Arnold et al. (2009) A Delphi clinical practice protocol for the management of very long chain acyl-CoA dehydrogenase deficiency. Mol Genet Metab 96:85-90.

Boneh et al. (2006). VLCAD deficiency: pitfalls in newborn screening and confirmation of diagnosis by mutation analysis. Mol Genet Metab 88, 166-170.

Goetzman et al. (2007). Expression and characterization of mutations in human very long-chain acyl-CoA dehydrogenase using a prokaryotic system. Mol Genet Metab 91, 138-147.

Goetzman et al. (2014). Long-chain acyl-CoA dehydrogenase deficiency as a cause of pulmonary surfactant dysfunction. J Biol Chem 289, 10668-10679.

Gregersen et al. (2008). Mitochondrial fatty acid oxidation defects—remaining challenges. J Inherit Metab Dis 31, 643-657.

Kalai et al. (2006) Structure-activity studies on the protection of Trimetazidine derivatives modified with nitroxides and their precursors from myocardial ischemia-reperfusion injury. Bioorg Medicinal Chem 14:5510-5516.

Kamijo et al. (1994) Mitochondrial trifunctional protein deficiency-catalytic heterogeneity of the mutant enzyme in two patients. J Clin Invest 93, 1740-1747.

Kantor et al. (2000). The antianginal drug trimetazidine shifts cardiac energy metabolism from fatty acid oxidation to glucose oxidation by inhibiting mitochondrial long-chain 3-ketoacyl coenzyme A thiolase. Circ Res 86, 580-588.

Kutala et al. (2006) Attenuation of myocardial ischemia-reperfusion injury by trimetazidine derivatives functionalized with antioxidant properties. J Pharmacol Exper Therapeut 317(3):921-928.

Laforet et al. (2009). Diagnostic assessment and long-term follow-up of 13 patients with Very Long-Chain Acyl-Coenzyme A dehydrogenase (VLCAD) deficiency. Neuromuscul Disord 19, 324-329.

Lehman et al. (1990). An acyl-coenzyme A dehydrogenase assay utilizing the ferricenium ion. Analytic. Biochem. 186, 280-284.

Mathur, et al. (1999). Molecular heterogeneity in very-long-chain acyl-CoA dehydrogenase deficiency causing pediatric cardiomyopathy and sudden death. Circulation 99, 1337-1343.

Mohsen et al. (1995). Ligand-induced conformational changes of thymidylate synthase detected by limited proteolysis. Biochemistry, 34:1669-77.

Nasser et al. (2004). Thermal unfolding of medium-chain acyl-CoA dehydrogenase and iso(3)valeryl-CoA dehydrogenase: study of the effect of genetic defects on enzyme stability. Biochim Biophys Acta 1690, 22-32.

Pena et al. (2016). Outcomes and genotype-phenotype correlations in 52 individuals with VLCAD deficiency diagnosed by NBS and enrolled in the IBEM-IS database. Mol Genet Metab.

Pons et al. (2000). Clinical and molecular heterogeneity in very-long-chain acyl-coenzyme A dehydrogenase deficiency. Pediatr Neurol 22, 98-105.

Spiekerkoetter et al. (2009) Management and outcome in 75 individuals with long-chain fatty acid oxidation defects: results from a workshop. J Inherit Metab Dis 32:488-497.

Spiekerkoetter et al. (2004) The early-onset phenotype of mitochondrial trifunctional protein deficiency: A lethal disorder with multiple tissue involvement. Journal of Inherited Metabolic Disease 27, 294-296.

Spiekerkoetter et al. (2003) Molecular and phenotypic heterogeneity in mitochondrial trifunctional protein deficiency due to beta-subunit mutations. Hum Mutat 21, 598-607.

Stanley et al. (2003). Metabolic therapy in the treatment of ischaemic heart disease: the pharmacology of trimetazidine. Fundam Clin Pharmacol 17, 133-145.

Tang (2006). Metabolic approach in heart failure: rethinking how we translate from theory to clinical practice. J Am Coll Cardiol 48, 999-1000.

Vockley et al. (2000). Mammalian branched-chain acyl-CoA dehydrogenases: molecular cloning and characterization of recombinant enzymes. Methods Enzymol 324, 241-258.

Watanabe et al. (2000). Molecular basis of very long chain acyl-CoA dehydrogenase deficiency in three Israeli patients: identification of a complex mutant allele with P65L and K247Q mutations, the former being an exonic mutation causing exon 3 skipping. Hum Mutat 15, 430-438.

Zhang et al. (2014). Clinical features and mutations in seven Chinese patients with very long chain acyl-CoA dehydrogenase deficiency. World J Pediatr 10, 119-125.

We claim:

1. A method of treating a disorder caused by a mis sense mutation in an enzyme of a fatty acid mitochondrial β-oxidation pathway or fatty acid mitochondrial transport protein/enzyme in a patient in need thereof, comprising administering to the patient an effective amount of trimetazidine or a derivative thereof, or a pharmaceutically acceptable salt or ester thereof acting as an inhibitor of activity of an enzyme of the β-oxidation pathway downstream of the enzyme of the fatty acid mitochondrial β-oxidation pathway or fatty acid mitochondrial transport protein/enzyme having the mis sense mutation, thereby increasing activity of the enzyme of the β-oxidation pathway or fatty acid mitochondrial transport protein/enzyme having the mis sense mutation,
   wherein a product of the enzyme of the fatty acid mitochondrial β-oxidation pathway or fatty acid mitochondrial transport protein/enzyme having the missense mutation stabilizes the enzyme of the β-oxidation pathway or fatty acid mitochondrial transport, or wherein one or more substrates or products of the enzyme of the β-oxidation pathway downstream in the β-oxidation pathway binds to, allosterically, and stabilizes the enzyme of the β-oxidation pathway or fatty acid mitochondrial transport protein/enzyme having the mis sense mutation, and
   wherein the enzyme of the fatty acid mitochondrial β-oxidation pathway or fatty acid mitochondrial transporter protein/enzyme is selected from the group consisting of very long chain acyl-CoA dehydrogenase (VLCAD), medium chain acyl-CoA dehydrogenase (MCAD), mitochondrial trifunctional protein (TFP), long-chain 3-ketoacyl-CoA thiolase (LCKAT), and mitochondrial membrane fatty acid transport protein.

2. The method of claim 1, wherein the missense mutation does not result in a complete loss of enzyme presence or activity.

3. The method of claim 1, wherein the missense mutation is K304E of MCAD, or any other MCAD harboring a homozygous or heterozygous missense mutation.

4. The method of claim 1, wherein the missense mutation is L540P, V174M, E609K, or any other VLCAD or VLCAD isoforms, harboring any destabilizing missense mutation(s).

5. The method of claim 1, wherein the TFP is the α-subunit or the β-subunit encoded by HADHA or HADHB genes, respectively.

6. The method of claim 5, wherein the missense mutation is E510Q of HADHA or R247C of HADHB, or any destabilizing missense mutations thereof.

7. The method of claim 1, wherein the enzyme of the β-oxidation pathway downstream in the β-oxidation pathway to the enzyme having the mis sense mutation is long-chain 3-ketoacyl-CoA thiolase (LCKAT) subunit.

8. The method claim 1, wherein the trimetazidine derivative has the structure:

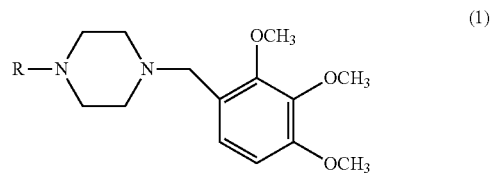

where R is a 5 to 7 member hydrocarbon or heterocyclic group substituted with one or more $C_1$-$C_6$ hydrocarbon groups.

9. The method of claim 8, wherein R is 2,2,5,5-tetramethylpyrrolinyl that is optionally substituted at its 4 position with a $C_1$-$C_6$ hydrocarbon group.

10. The method of claim 9, wherein R is 2,2,5,5-tetramethyl-4-phenylpyrrolinyl.

11. The method of claim 1, wherein the mitochondrial membrane fatty acid transport protein is carnitine palmitoyltransferase I (CPT I) or carnitine palmitoyltransferase 2 (CPT II).

12. The method of claim 1, further comprising administering to the patient an amount of a Peroxisome Proliferator-Activated Receptor delta (PPARδ) agonist effective to increase activity of the enzyme of the β-oxidation pathway or fatty acid mitochondrial transport protein/enzyme having the mis sense mutation in the patient.

13. The method of claim 12, wherein the PPARδ agonist is chosen from GW501516, GW0742, or any PPARδ agonist that enhances activity or presence of the enzyme of the β-oxidation pathway or fatty acid mitochondrial transport protein/enzyme having the missense mutation.

14. The method of claim 1, wherein the product of the enzyme of the β-oxidation pathway or fatty acid mitochondrial transport protein/enzyme having the mis sense mutation is a reverse reaction substrate.

15. The method of claim 9, wherein the $C_1$-$C_6$ hydrocarbon group is a phenyl group.

* * * * *

UNITED STATES PATENT AND TRADEMARK OFFICE
CERTIFICATE OF CORRECTION

| | |
|---|---|
| PATENT NO. | : 11,813,258 B2 |
| APPLICATION NO. | : 17/344084 |
| DATED | : November 14, 2023 |
| INVENTOR(S) | : Al-Walid A. Mohsen et al. |

Page 1 of 1

It is certified that error appears in the above-identified patent and that said Letters Patent is hereby corrected as shown below:

In the Claims

Column 49, Line 18, Claim 1, delete "mis sense" and insert -- missense --

Column 49, Lines 26-27, Claim 1, delete "mis sense" and insert -- missense --

Column 49, Line 29, Claim 1, delete "mis sense" and insert -- missense --

Column 49, Lines 39-40, Claim 1, delete "mis sense" and insert -- missense --

Column 50, Line 19, Claim 7, delete "mis sense" and insert -- missense --

Column 50, Line 21, Claim 8, delete "method" and insert -- method of --

Column 50, Line 44, Claim 11, delete "2" and insert -- II --

Column 50, Line 51, Claim 12, delete "mis sense" and insert -- missense --

Column 50, Line 59, Claim 14, delete "mis sense" and insert -- missense --

Signed and Sealed this
Thirteenth Day of February, 2024

Katherine Kelly Vidal
*Director of the United States Patent and Trademark Office*

SEQUENCE LISTING

<160> NUMBER OF SEQ ID NOS: 6

<210> SEQ ID NO 1
<211> LENGTH: 655
<212> TYPE: PRT
<213> ORGANISM: Homo sapiens

<400> SEQUENCE: 1

Met Gln Ala Ala Arg Met Ala Ala Ser Leu Gly Arg Gln Leu Leu Arg
1               5                   10                  15

Leu Gly Gly Gly Ser Ser Arg Leu Thr Ala Leu Leu Gly Gln Pro Arg
            20                  25                  30

Pro Gly Pro Ala Arg Arg Pro Tyr Ala Gly Gly Ala Ala Gln Leu Ala
        35                  40                  45

Leu Asp Lys Ser Asp Ser His Pro Ser Asp Ala Leu Thr Arg Lys Lys
50                  55                  60

Pro Ala Lys Ala Glu Ser Lys Ser Phe Ala Val Gly Met Phe Lys Gly
65                  70                  75                  80

Gln Leu Thr Thr Asp Gln Val Phe Pro Tyr Pro Ser Val Leu Asn Glu
                85                  90                  95

Glu Gln Thr Gln Phe Leu Lys Glu Leu Val Glu Pro Val Ser Arg Phe
            100                 105                 110

Phe Glu Glu Val Asn Asp Pro Ala Lys Asn Asp Ala Leu Glu Met Val
        115                 120                 125

Glu Glu Thr Thr Trp Gln Gly Leu Lys Glu Leu Gly Ala Phe Gly Leu
130                 135                 140

Gln Val Pro Ser Glu Leu Gly Gly Val Gly Leu Cys Asn Thr Gln Tyr
145                 150                 155                 160

Ala Arg Leu Val Glu Ile Val Gly Met His Asp Leu Gly Val Gly Ile
                165                 170                 175

Thr Leu Gly Ala His Gln Ser Ile Gly Phe Lys Gly Ile Leu Leu Phe
            180                 185                 190

Gly Thr Lys Ala Gln Lys Glu Lys Tyr Leu Pro Lys Leu Ala Ser Gly
        195                 200                 205

Glu Thr Val Ala Ala Phe Cys Leu Thr Glu Pro Ser Ser Gly Ser Asp
210                 215                 220

Ala Ala Ser Ile Arg Thr Ser Ala Val Pro Ser Pro Cys Gly Lys Tyr
225                 230                 235                 240

Tyr Thr Leu Asn Gly Ser Lys Leu Trp Ile Ser Asn Gly Gly Leu Ala
                245                 250                 255

Asp Ile Phe Thr Val Phe Ala Lys Thr Pro Val Thr Asp Pro Ala Thr
            260                 265                 270

Gly Ala Val Lys Glu Lys Ile Thr Ala Phe Val Val Glu Arg Gly Phe
        275                 280                 285

Gly Gly Ile Thr His Gly Pro Pro Glu Lys Lys Met Gly Ile Lys Ala
290                 295                 300

Ser Asn Thr Ala Glu Val Phe Phe Asp Gly Val Arg Val Pro Ser Glu
305                 310                 315                 320

Asn Val Leu Gly Glu Val Gly Ser Gly Phe Lys Val Ala Met His Ile
                325                 330                 335

Leu Asn Asn Gly Arg Phe Gly Met Ala Ala Leu Ala Gly Thr Met
            340                 345                 350

Arg Gly Ile Ile Ala Lys Ala Val Asp His Ala Thr Asn Arg Thr Gln
        355                 360                 365

-continued

```
Phe Gly Glu Lys Ile His Asn Phe Gly Leu Ile Gln Glu Lys Leu Ala
    370                 375                 380
Arg Met Val Met Leu Gln Tyr Val Thr Glu Ser Met Ala Tyr Met Val
385                 390                 395                 400
Ser Ala Asn Met Asp Gln Gly Ala Thr Asp Phe Gln Ile Glu Ala Ala
                405                 410                 415
Ile Ser Lys Ile Phe Gly Ser Glu Ala Ala Trp Lys Val Thr Asp Glu
            420                 425                 430
Cys Ile Gln Ile Met Gly Gly Met Gly Phe Met Lys Glu Pro Gly Val
        435                 440                 445
Glu Arg Val Leu Arg Asp Leu Arg Ile Phe Arg Ile Phe Glu Gly Thr
450                 455                 460
Asn Asp Ile Leu Arg Leu Phe Val Ala Leu Gln Gly Cys Met Asp Lys
465                 470                 475                 480
Gly Lys Glu Leu Ser Gly Leu Gly Ser Ala Leu Lys Asn Pro Phe Gly
                485                 490                 495
Asn Ala Gly Leu Leu Gly Glu Ala Gly Lys Gln Leu Arg Arg Arg
            500                 505                 510
Ala Gly Leu Gly Ser Gly Leu Ser Leu Ser Gly Leu Val His Pro Glu
        515                 520                 525
Leu Ser Arg Ser Gly Glu Leu Ala Val Arg Ala Leu Glu Gln Phe Ala
530                 535                 540
Thr Val Val Glu Ala Lys Leu Ile Lys His Lys Lys Gly Ile Val Asn
545                 550                 555                 560
Glu Gln Phe Leu Leu Gln Arg Leu Ala Asp Gly Ala Ile Asp Leu Tyr
                565                 570                 575
Ala Met Val Val Val Leu Ser Arg Ala Ser Arg Ser Leu Ser Glu Gly
            580                 585                 590
His Pro Thr Ala Gln His Glu Lys Met Leu Cys Asp Thr Trp Cys Ile
        595                 600                 605
Glu Ala Ala Ala Arg Ile Arg Glu Gly Met Ala Ala Leu Gln Ser Asp
610                 615                 620
Pro Trp Gln Gln Glu Leu Tyr Arg Asn Phe Lys Ser Ile Ser Lys Ala
625                 630                 635                 640
Leu Val Glu Arg Gly Gly Val Val Thr Ser Asn Pro Leu Gly Phe
                645                 650                 655

<210> SEQ ID NO 2
<211> LENGTH: 430
<212> TYPE: PRT
<213> ORGANISM: Homo sapiens

<400> SEQUENCE: 2

Met Ala Ala Arg Leu Leu Arg Gly Ser Leu Arg Val Leu Gly Gly His
1               5                   10                  15
Arg Ala Pro Arg Gln Leu Pro Ala Ala Arg Cys Ser His Ser Gly Gly
            20                  25                  30
Glu Glu Arg Leu Glu Thr Pro Ser Ala Lys Lys Leu Thr Asp Ile Gly
        35                  40                  45
Ile Arg Arg Ile Phe Ser Pro Glu His Asp Ile Phe Arg Lys Ser Val
    50                  55                  60
Arg Lys Phe Phe Gln Glu Glu Val Ile Pro His His Ser Glu Trp Glu
65              70                  75                  80
Lys Ala Gly Glu Val Ser Arg Glu Val Trp Glu Lys Ala Gly Lys Gln
                85                  90                  95
```

```
Gly Leu Leu Gly Val Asn Ile Ala Glu His Leu Gly Ile Gly Gly
            100                 105                 110

Asp Leu Tyr Ser Ala Ala Ile Val Trp Glu Gln Ala Tyr Ser Asn
            115                 120                 125

Cys Ser Gly Pro Gly Phe Ser Ile His Ser Gly Ile Val Met Ser Tyr
            130                 135                 140

Ile Thr Asn His Gly Ser Glu Glu Gln Ile Lys His Phe Ile Pro Gln
145                 150                 155                 160

Met Thr Ala Gly Lys Cys Ile Gly Ala Ile Ala Met Thr Glu Pro Gly
                165                 170                 175

Ala Gly Ser Asp Leu Gln Gly Ile Lys Thr Asn Ala Lys Lys Asp Gly
            180                 185                 190

Ser Asp Trp Ile Leu Asn Gly Ser Lys Val Phe Ile Ser Asn Gly Ser
            195                 200                 205

Leu Ser Asp Val Val Ile Val Val Ala Val Thr Asn His Glu Ala Pro
210                 215                 220

Ser Pro Ala His Gly Ile Ser Leu Phe Leu Val Glu Asn Gly Met Lys
225                 230                 235                 240

Gly Phe Ile Lys Gly Arg Lys Leu His Lys Met Gly Leu Lys Ala Gln
                245                 250                 255

Asp Thr Ala Glu Leu Phe Phe Glu Asp Ile Arg Leu Pro Ala Ser Ala
            260                 265                 270

Leu Leu Gly Glu Glu Asn Lys Gly Phe Tyr Tyr Ile Met Lys Glu Leu
            275                 280                 285

Pro Gln Glu Arg Leu Leu Ile Ala Asp Val Ala Ile Ser Ala Ser Glu
290                 295                 300

Phe Met Phe Glu Glu Thr Arg Asn Tyr Val Lys Gln Arg Lys Ala Phe
305                 310                 315                 320

Gly Lys Thr Val Ala His Leu Gln Thr Val Gln His Lys Leu Ala Glu
                325                 330                 335

Leu Lys Thr His Ile Cys Val Thr Arg Ala Phe Val Asp Asn Cys Leu
            340                 345                 350

Gln Leu His Glu Ala Lys Arg Leu Asp Ser Ala Thr Ala Cys Met Ala
            355                 360                 365

Lys Tyr Trp Ala Ser Glu Leu Gln Asn Ser Val Ala Tyr Asp Cys Val
370                 375                 380

Gln Leu His Gly Gly Trp Gly Tyr Met Trp Glu Tyr Pro Ile Ala Lys
385                 390                 395                 400

Ala Tyr Val Asp Ala Arg Val Gln Pro Ile Tyr Gly Gly Thr Asn Glu
                405                 410                 415

Ile Met Lys Glu Leu Ile Ala Arg Glu Ile Val Phe Asp Lys
            420                 425                 430

<210> SEQ ID NO 3
<211> LENGTH: 421
<212> TYPE: PRT
<213> ORGANISM: Homo sapiens

<400> SEQUENCE: 3

Met Ala Ala Gly Phe Gly Arg Cys Cys Arg Val Leu Arg Ser Ile Ser
1               5                   10                  15

Arg Phe His Trp Arg Ser Gln His Thr Lys Ala Asn Arg Gln Arg Glu
                20                  25                  30

Pro Gly Leu Gly Phe Ser Phe Glu Phe Thr Glu Gln Gln Lys Glu Phe
```

```
                35                  40                  45
Gln Ala Thr Ala Arg Lys Phe Ala Arg Glu Glu Ile Ile Pro Val Ala
 50                  55                  60

Ala Glu Tyr Asp Lys Thr Gly Glu Tyr Pro Val Pro Leu Ile Arg Arg
 65                  70                  75                  80

Ala Trp Glu Leu Gly Leu Met Asn Thr His Ile Pro Glu Asn Cys Gly
                 85                  90                  95

Gly Leu Gly Leu Gly Thr Phe Asp Ala Cys Leu Ile Ser Glu Glu Leu
                100                 105                 110

Ala Tyr Gly Cys Thr Gly Val Gln Thr Ala Ile Glu Gly Asn Ser Leu
            115                 120                 125

Gly Gln Met Pro Ile Ile Ile Ala Gly Asn Asp Gln Gln Lys Lys Lys
        130                 135                 140

Tyr Leu Gly Arg Met Thr Glu Glu Pro Leu Met Cys Ala Tyr Cys Val
145                 150                 155                 160

Thr Glu Pro Gly Ala Gly Ser Asp Val Ala Gly Ile Lys Thr Lys Ala
                165                 170                 175

Glu Lys Lys Gly Asp Glu Tyr Ile Ile Asn Gly Gln Lys Met Trp Ile
            180                 185                 190

Thr Asn Gly Gly Lys Ala Asn Trp Tyr Phe Leu Leu Ala Arg Ser Asp
        195                 200                 205

Pro Asp Pro Lys Ala Pro Ala Asn Lys Ala Phe Thr Gly Phe Ile Val
210                 215                 220

Glu Ala Asp Thr Pro Gly Ile Gln Ile Gly Arg Lys Glu Leu Asn Met
225                 230                 235                 240

Gly Gln Arg Cys Ser Asp Thr Arg Gly Ile Val Phe Glu Asp Val Lys
                245                 250                 255

Val Pro Lys Glu Asn Val Leu Ile Gly Asp Gly Ala Gly Phe Lys Val
            260                 265                 270

Ala Met Gly Ala Phe Asp Lys Thr Arg Pro Val Val Ala Ala Gly Ala
        275                 280                 285

Val Gly Leu Ala Gln Arg Ala Leu Asp Glu Ala Thr Lys Tyr Ala Leu
290                 295                 300

Glu Arg Lys Thr Phe Gly Lys Leu Leu Val Glu His Gln Ala Ile Ser
305                 310                 315                 320

Phe Met Leu Ala Glu Met Ala Met Lys Val Glu Leu Ala Arg Met Ser
                325                 330                 335

Tyr Gln Arg Ala Ala Trp Glu Val Asp Ser Gly Arg Arg Asn Thr Tyr
            340                 345                 350

Tyr Ala Ser Ile Ala Lys Ala Phe Ala Gly Asp Ile Ala Asn Gln Leu
        355                 360                 365

Ala Thr Asp Ala Val Gln Ile Leu Gly Gly Asn Gly Phe Asn Thr Glu
    370                 375                 380

Tyr Pro Val Glu Lys Leu Met Arg Asp Ala Lys Ile Tyr Gln Ile Tyr
385                 390                 395                 400

Glu Gly Thr Ser Gln Ile Gln Arg Leu Ile Val Ala Arg Glu His Ile
                405                 410                 415

Asp Lys Tyr Lys Asn
            420

<210> SEQ ID NO 4
<211> LENGTH: 412
<212> TYPE: PRT
<213> ORGANISM: Homo sapiens
```

<400> SEQUENCE: 4

```
Met Ala Ala Ala Leu Leu Ala Arg Ala Ser Gly Pro Ala Arg Arg Ala
1               5                   10                  15

Leu Cys Pro Arg Ala Trp Arg Gln Leu His Thr Ile Tyr Gln Ser Val
            20                  25                  30

Glu Leu Pro Glu Thr His Gln Met Leu Leu Gln Thr Cys Arg Asp Phe
        35                  40                  45

Ala Glu Lys Glu Leu Phe Pro Ile Ala Ala Gln Val Asp Lys Glu His
    50                  55                  60

Leu Phe Pro Ala Ala Gln Val Lys Lys Met Gly Gly Leu Gly Leu Leu
65                  70                  75                  80

Ala Met Asp Val Pro Glu Glu Leu Gly Gly Ala Gly Leu Asp Tyr Leu
                85                  90                  95

Ala Tyr Ala Ile Ala Met Glu Glu Ile Ser Arg Gly Cys Ala Ser Thr
                100                 105                 110

Gly Val Ile Met Ser Val Asn Asn Ser Leu Tyr Leu Gly Pro Ile Leu
            115                 120                 125

Lys Phe Gly Ser Lys Glu Gln Lys Gln Ala Trp Val Thr Pro Phe Thr
            130                 135                 140

Ser Gly Asp Lys Ile Gly Cys Phe Ala Leu Ser Glu Pro Gly Asn Gly
145                 150                 155                 160

Ser Asp Ala Gly Ala Ala Ser Thr Thr Ala Arg Ala Glu Gly Asp Ser
                165                 170                 175

Trp Val Leu Asn Gly Thr Lys Ala Trp Ile Thr Asn Ala Trp Glu Ala
                180                 185                 190

Ser Ala Ala Val Val Phe Ala Ser Thr Asp Arg Ala Leu Gln Asn Lys
            195                 200                 205

Gly Ile Ser Ala Phe Leu Val Pro Met Pro Thr Pro Gly Leu Thr Leu
            210                 215                 220

Gly Lys Lys Glu Asp Lys Leu Gly Ile Arg Gly Ser Ser Thr Ala Asn
225                 230                 235                 240

Leu Ile Phe Glu Asp Cys Arg Ile Pro Lys Asp Ser Ile Leu Gly Glu
                245                 250                 255

Pro Gly Met Gly Phe Lys Ile Ala Met Gln Thr Leu Asp Met Gly Arg
            260                 265                 270

Ile Gly Ile Ala Ser Gln Ala Leu Gly Ile Ala Gln Thr Ala Leu Asp
            275                 280                 285

Cys Ala Val Asn Tyr Ala Glu Asn Arg Met Ala Phe Gly Ala Pro Leu
290                 295                 300

Thr Lys Leu Gln Val Ile Gln Phe Lys Leu Ala Asp Met Ala Leu Ala
305                 310                 315                 320

Leu Glu Ser Ala Arg Leu Leu Thr Trp Arg Ala Ala Met Leu Lys Asp
                325                 330                 335

Asn Lys Lys Pro Phe Ile Lys Glu Ala Ala Met Ala Lys Leu Ala Ala
            340                 345                 350

Ser Glu Ala Ala Thr Ala Ile Ser His Gln Ala Ile Gln Ile Leu Gly
            355                 360                 365

Gly Met Gly Tyr Val Thr Glu Met Pro Ala Glu Arg His Tyr Arg Asp
            370                 375                 380

Ala Arg Ile Thr Glu Ile Tyr Glu Gly Thr Ser Glu Ile Gln Arg Leu
385                 390                 395                 400

Val Ile Ala Gly His Leu Leu Arg Ser Tyr Arg Ser
```

<210> SEQ ID NO 5
<211> LENGTH: 763
<212> TYPE: PRT
<213> ORGANISM: Homo sapiens

<400> SEQUENCE: 5

| | | | | | | | | | | | | | | |
|---|---|---|---|---|---|---|---|---|---|---|---|---|---|---|
| Met | Val | Ala | Cys | Arg | Ala | Ile | Gly | Ile | Leu | Ser | Arg | Phe | Ser | Ala | Phe |
| 1 | | | | 5 | | | | | 10 | | | | | 15 | |
| Arg | Ile | Leu | Arg | Ser | Arg | Gly | Tyr | Ile | Cys | Arg | Asn | Phe | Thr | Gly | Ser |
| | | | 20 | | | | | 25 | | | | | 30 | | |
| Ser | Ala | Leu | Leu | Thr | Arg | Thr | His | Ile | Asn | Tyr | Gly | Val | Lys | Gly | Asp |
| | | | 35 | | | | 40 | | | | | 45 | | | |
| Val | Ala | Val | Val | Arg | Ile | Asn | Ser | Pro | Asn | Ser | Lys | Val | Asn | Thr | Leu |
| | 50 | | | | | 55 | | | | | 60 | | | | |
| Ser | Lys | Glu | Leu | His | Ser | Glu | Phe | Ser | Glu | Val | Met | Asn | Glu | Ile | Trp |
| 65 | | | | | 70 | | | | | 75 | | | | | 80 |
| Ala | Ser | Asp | Gln | Ile | Arg | Ser | Ala | Val | Leu | Ile | Ser | Ser | Lys | Pro | Gly |
| | | | | 85 | | | | | 90 | | | | | 95 | |
| Cys | Phe | Ile | Ala | Gly | Ala | Asp | Ile | Asn | Met | Leu | Ala | Ala | Cys | Lys | Thr |
| | | | 100 | | | | | 105 | | | | | 110 | | |
| Leu | Gln | Glu | Val | Thr | Gln | Leu | Ser | Gln | Glu | Ala | Gln | Arg | Ile | Val | Glu |
| | | | 115 | | | | 120 | | | | | 125 | | | |
| Lys | Leu | Glu | Lys | Ser | Thr | Lys | Pro | Ile | Val | Ala | Ala | Ile | Asn | Gly | Ser |
| | 130 | | | | | 135 | | | | | 140 | | | | |
| Cys | Leu | Gly | Gly | Gly | Leu | Glu | Val | Ala | Ile | Ser | Cys | Gln | Tyr | Arg | Ile |
| 145 | | | | | 150 | | | | | 155 | | | | | 160 |
| Ala | Thr | Lys | Asp | Arg | Lys | Thr | Val | Leu | Gly | Thr | Pro | Glu | Val | Leu | Leu |
| | | | | 165 | | | | | 170 | | | | | 175 | |
| Gly | Ala | Leu | Pro | Gly | Ala | Gly | Gly | Thr | Gln | Arg | Leu | Pro | Lys | Met | Val |
| | | | 180 | | | | | 185 | | | | | 190 | | |
| Gly | Val | Pro | Ala | Ala | Leu | Asp | Met | Met | Leu | Thr | Gly | Arg | Ser | Ile | Arg |
| | | | 195 | | | | | 200 | | | | | 205 | | |
| Ala | Asp | Arg | Ala | Lys | Lys | Met | Gly | Leu | Val | Asp | Gln | Leu | Val | Glu | Pro |
| | 210 | | | | | 215 | | | | | 220 | | | | |
| Leu | Gly | Pro | Gly | Leu | Lys | Pro | Pro | Glu | Glu | Arg | Thr | Ile | Glu | Tyr | Leu |
| 225 | | | | | 230 | | | | | 235 | | | | | 240 |
| Glu | Glu | Val | Ala | Ile | Thr | Phe | Ala | Lys | Gly | Leu | Ala | Asp | Lys | Lys | Ile |
| | | | | 245 | | | | | 250 | | | | | 255 | |
| Ser | Pro | Lys | Arg | Asp | Lys | Gly | Leu | Val | Glu | Lys | Leu | Thr | Ala | Tyr | Ala |
| | | | 260 | | | | | 265 | | | | | 270 | | |
| Met | Thr | Ile | Pro | Phe | Val | Arg | Gln | Gln | Val | Tyr | Lys | Lys | Val | Glu | Glu |
| | | | 275 | | | | | 280 | | | | | 285 | | |
| Lys | Val | Arg | Lys | Gln | Thr | Lys | Gly | Leu | Tyr | Pro | Ala | Pro | Leu | Lys | Ile |
| | 290 | | | | | 295 | | | | | 300 | | | | |
| Ile | Asp | Val | Val | Lys | Thr | Gly | Ile | Glu | Gln | Gly | Ser | Asp | Ala | Gly | Tyr |
| 305 | | | | | 310 | | | | | 315 | | | | | 320 |
| Leu | Cys | Glu | Ser | Gln | Lys | Phe | Gly | Glu | Leu | Val | Met | Thr | Lys | Glu | Ser |
| | | | | 325 | | | | | 330 | | | | | 335 | |
| Lys | Ala | Leu | Met | Gly | Leu | Tyr | His | Gly | Gln | Val | Leu | Cys | Lys | Lys | Asn |
| | | | 340 | | | | | 345 | | | | | 350 | | |
| Lys | Phe | Gly | Ala | Pro | Gln | Lys | Asp | Val | Lys | His | Leu | Ala | Ile | Leu | Gly |
| | | | 355 | | | | | 360 | | | | | 365 | | |

Ala Gly Leu Met Gly Ala Gly Ile Ala Gln Val Ser Val Asp Lys Gly
        370                 375                 380

Leu Lys Thr Ile Leu Lys Asp Ala Thr Leu Thr Ala Leu Asp Arg Gly
385                 390                 395                 400

Gln Gln Gln Val Phe Lys Gly Leu Asn Asp Lys Val Lys Lys Ala
                    405                 410                 415

Leu Thr Ser Phe Glu Arg Asp Ser Ile Phe Ser Asn Leu Thr Gly Gln
                420                 425                 430

Leu Asp Tyr Gln Gly Phe Glu Lys Ala Asp Met Val Ile Glu Ala Val
            435                 440                 445

Phe Glu Asp Leu Ser Leu Lys His Arg Val Leu Lys Glu Val Glu Ala
450                 455                 460

Val Ile Pro Asp His Cys Ile Phe Ala Ser Asn Thr Ser Ala Leu Pro
465                 470                 475                 480

Ile Ser Glu Ile Ala Ala Val Ser Lys Arg Pro Glu Lys Val Ile Gly
                485                 490                 495

Met His Tyr Phe Ser Pro Val Asp Lys Met Gln Leu Leu Glu Ile Ile
                500                 505                 510

Thr Thr Glu Lys Thr Ser Lys Asp Thr Ser Ala Ser Ala Val Ala Val
            515                 520                 525

Gly Leu Lys Gln Gly Lys Val Ile Val Val Lys Asp Gly Pro Gly
530                 535                 540

Phe Tyr Thr Thr Arg Cys Leu Ala Pro Met Met Ser Glu Val Ile Arg
545                 550                 555                 560

Ile Leu Gln Glu Gly Val Asp Pro Lys Lys Leu Asp Ser Leu Thr Thr
                565                 570                 575

Ser Phe Gly Phe Pro Val Gly Ala Ala Thr Leu Val Asp Glu Val Gly
                580                 585                 590

Val Asp Val Ala Lys His Val Ala Glu Asp Leu Gly Lys Val Phe Gly
            595                 600                 605

Glu Arg Phe Gly Gly Gly Asn Pro Glu Leu Leu Thr Gln Met Val Ser
            610                 615                 620

Lys Gly Phe Leu Gly Arg Lys Ser Gly Lys Gly Phe Tyr Ile Tyr Gln
625                 630                 635                 640

Glu Gly Val Lys Arg Lys Asp Leu Asn Ser Asp Met Asp Ser Ile Leu
                645                 650                 655

Ala Ser Leu Lys Leu Pro Pro Lys Ser Glu Val Ser Ser Asp Glu Asp
                660                 665                 670

Ile Gln Phe Arg Leu Val Thr Arg Phe Val Asn Glu Ala Val Met Cys
            675                 680                 685

Leu Gln Glu Gly Ile Leu Ala Thr Pro Ala Glu Gly Asp Ile Gly Ala
690                 695                 700

Val Phe Gly Leu Gly Phe Pro Pro Cys Leu Gly Gly Pro Phe Arg Phe
705                 710                 715                 720

Val Asp Leu Tyr Gly Ala Gln Lys Ile Val Asp Arg Leu Lys Lys Tyr
                725                 730                 735

Glu Ala Ala Tyr Gly Lys Gln Phe Thr Pro Cys Gln Leu Leu Ala Asp
                740                 745                 750

His Ala Asn Ser Pro Asn Lys Lys Phe Tyr Gln
            755                 760

<210> SEQ ID NO 6
<211> LENGTH: 474
<212> TYPE: PRT

<213> ORGANISM: Homo sapiens

<400> SEQUENCE: 6

```
Met Thr Ile Leu Thr Tyr Pro Phe Lys Asn Leu Pro Thr Ala Ser Lys
1               5                   10                  15
Trp Ala Leu Arg Phe Ser Ile Arg Pro Leu Ser Cys Ser Ser Gln Leu
            20                  25                  30
Arg Ala Ala Pro Ala Val Gln Thr Lys Thr Lys Lys Thr Leu Ala Lys
        35                  40                  45
Pro Asn Ile Arg Asn Val Val Val Asp Gly Val Arg Thr Pro Phe
50                  55                  60
Leu Leu Ser Gly Thr Ser Tyr Lys Asp Leu Met Pro His Asp Leu Ala
65                  70                  75                  80
Arg Ala Ala Leu Thr Gly Leu Leu His Arg Thr Ser Val Pro Lys Glu
                85                  90                  95
Val Val Asp Tyr Ile Ile Phe Gly Thr Val Ile Gln Glu Val Lys Thr
            100                 105                 110
Ser Asn Val Ala Arg Glu Ala Ala Leu Gly Ala Gly Phe Ser Asp Lys
        115                 120                 125
Thr Pro Ala His Thr Val Thr Met Ala Cys Ile Ser Ala Asn Gln Ala
130                 135                 140
Met Thr Thr Gly Val Gly Leu Ile Ala Ser Gly Gln Cys Asp Val Ile
145                 150                 155                 160
Val Ala Gly Gly Val Glu Leu Met Ser Asp Val Pro Ile Arg His Ser
                165                 170                 175
Arg Lys Met Arg Lys Leu Met Leu Asp Leu Asn Lys Ala Lys Ser Met
            180                 185                 190
Gly Gln Arg Leu Ser Leu Ile Ser Lys Phe Arg Phe Asn Phe Leu Ala
        195                 200                 205
Pro Glu Leu Pro Ala Val Ser Glu Phe Ser Thr Ser Glu Thr Met Gly
210                 215                 220
His Ser Ala Asp Arg Leu Ala Ala Phe Ala Val Ser Arg Leu Glu
225                 230                 235                 240
Gln Asp Glu Tyr Ala Leu Arg Ser His Ser Leu Ala Lys Lys Ala Gln
                245                 250                 255
Asp Glu Gly Leu Leu Ser Asp Val Val Pro Phe Lys Val Pro Gly Lys
            260                 265                 270
Asp Thr Val Thr Lys Asp Asn Gly Ile Arg Pro Ser Ser Leu Glu Gln
        275                 280                 285
Met Ala Lys Leu Lys Pro Ala Phe Ile Lys Pro Tyr Gly Thr Val Thr
290                 295                 300
Ala Ala Asn Ser Ser Phe Leu Thr Asp Gly Ala Ser Ala Met Leu Ile
305                 310                 315                 320
Met Ala Glu Glu Lys Ala Leu Ala Met Gly Tyr Lys Pro Lys Ala Tyr
                325                 330                 335
Leu Arg Asp Phe Met Tyr Val Ser Gln Asp Pro Lys Asp Gln Leu Leu
            340                 345                 350
Leu Gly Pro Thr Tyr Ala Thr Pro Lys Val Leu Glu Lys Ala Gly Leu
        355                 360                 365
Thr Met Asn Asp Ile Asp Ala Phe Glu Phe His Glu Ala Phe Ser Gly
370                 375                 380
Gln Ile Leu Ala Asn Phe Lys Ala Met Asp Ser Asp Trp Phe Ala Glu
385                 390                 395                 400
```

```
Asn Tyr Met Gly Arg Lys Thr Lys Val Gly Leu Pro Pro Leu Glu Lys
                405             410                 415

Phe Asn Asn Trp Gly Gly Ser Leu Ser Leu Gly His Pro Phe Gly Ala
            420             425                 430

Thr Gly Cys Arg Leu Val Met Ala Ala Ala Asn Arg Leu Arg Lys Glu
        435             440                 445

Gly Gly Gln Tyr Gly Leu Val Ala Ala Cys Ala Ala Gly Gly Gln Gly
    450             455                 460

His Ala Met Ile Val Glu Ala Tyr Pro Lys
465             470
```